United States Patent
Tiran et al.

(10) Patent No.: US 8,969,359 B2
(45) Date of Patent: *Mar. 3, 2015

(54) GYRASE AND TOPOISOMERASE IV INHIBITORS

(71) Applicant: Vertex Pharmaceuticals Incorporated, Cambridge, MA (US)

(72) Inventors: Arnaud Le Tiran, Croissy sur Seine (FR); Anne-Laure Grillot, Milton, MA (US); Paul S. Charifson, Framingham, MA (US); Youssef Laafiret Bennani, Lorraine (CA); Hardwin O'Dowd, Boston, MA (US); Emanuele Perola, Brookline, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/908,593

(22) Filed: Jun. 3, 2013

(65) Prior Publication Data

US 2013/0289002 A1    Oct. 31, 2013

Related U.S. Application Data

(63) Continuation of application No. 13/349,789, filed on Jan. 13, 2012, now Pat. No. 8,481,551.

(60) Provisional application No. 61/515,174, filed on Aug. 4, 2011, provisional application No. 61/515,249, filed on Aug. 4, 2011, provisional application No. 61/432,965, filed on Jan. 14, 2011, provisional application No. 61/499,134, filed on Jun. 20, 2011.

(51) Int. Cl.
| | |
|---|---|
| *A01N 43/54* | (2006.01) |
| *C07D 239/42* | (2006.01) |
| *C07D 401/04* | (2006.01) |
| *C07D 405/14* | (2006.01) |
| *C07F 9/6558* | (2006.01) |

(52) U.S. Cl.
CPC .......... *C07D 405/14* (2013.01); *C07F 9/65586* (2013.01)
USPC .............. 514/256; 544/243; 544/295; 514/80

(58) Field of Classification Search
CPC .... C07D 5/14; C07F 9/65586; A61K 31/506; A61K 31/575
USPC .............................. 544/243, 295; 514/80, 256
See application file for complete search history.

(56) References Cited

U.S. PATENT DOCUMENTS

| | | | |
|---|---|---|---|
| 3,856,957 A | 12/1974 | Seng et al. | |
| 4,174,400 A | 11/1979 | Mrozik | |
| 4,512,998 A | 4/1985 | Nafissi-Varchei | |
| 5,529,998 A | 6/1996 | Habich et al. | |
| 5,643,935 A | 7/1997 | Dykstra et al. | |
| 6,069,160 A | 5/2000 | Stolle et al. | |
| 6,632,809 B2 | 10/2003 | Grillot et al. | |
| RE40,245 E | 4/2008 | Grillot et al. | |

(Continued)

FOREIGN PATENT DOCUMENTS

| | | |
|---|---|---|
| EP | 0433648 | 6/1991 |
| EP | 0738726 | 10/1996 |

(Continued)

OTHER PUBLICATIONS

Beers, M. H., and Berkow, R., "The Merck Manual of Diagnosis and Therapy", 7th Edition, Chapter 156—Bacteremia and Septic Shock, Merck Research Laboratories, Whitehouse Station, NJ pp. 1143-1147 (1999).
Champoux, J.J., Annu. Rev. Biochem., 2001, 70, pp. 369-413.
Charifson et al., J. Med. Chem., 2008, 51, pp. 5243-5263.
Charles W. Stratton, MD. "In Vitro Susceptibility Testing Versus in Vivo-Effectiveness" The Medical Clinics of North America 2006, 90, 1077-1088.
Drlica and Zhao, Microbiology and Molecular Biology Reviews, 1997, 61, pp. 377-392.

(Continued)

*Primary Examiner* — Alexander R Pagano
(74) *Attorney, Agent, or Firm* — Brinks Gilson & Lione

(57) ABSTRACT

The present invention relates to a compound of formula (I)

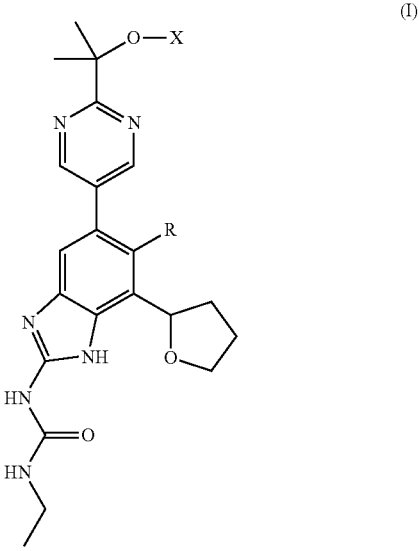

or a pharmaceutically acceptable salt thereof wherein X and R are as defined herein. The compounds of formula (I) are useful as gyrase and/or topoisomerase IV inhibitors for treating bacterial infections. The compounds of formula (I) either possess a broad range of anti-bacterial activity and advantageous toxicological properties or are prodrugs of compounds having said activity.

25 Claims, 2 Drawing Sheets

(56) References Cited

U.S. PATENT DOCUMENTS

| | | | |
|---|---|---|---|
| 7,414,046 B2* | 8/2008 | Grillot et al. | 514/215 |
| 7,495,014 B2 | 2/2009 | Charifson et al. | |
| 7,569,591 B2 | 8/2009 | Charifson et al. | |
| 7,582,641 B2 | 9/2009 | Charifson et al. | |
| 7,618,974 B2 | 11/2009 | Charifson et al. | |
| 7,674,801 B2 | 3/2010 | Basarab et al. | |
| 7,727,992 B2 | 6/2010 | Charifson et al. | |
| 7,977,340 B2 | 7/2011 | Haydon et al. | |
| 8,034,832 B2 | 10/2011 | Charifson et al. | |
| 8,067,606 B2 | 11/2011 | Charifson et al. | |
| 8,188,095 B2 | 5/2012 | Charifson et al. | |
| 8,193,352 B2 | 6/2012 | Charifson et al. | |
| 8,404,852 B2 | 3/2013 | Charifson et al. | |
| 8,426,426 B2 | 4/2013 | Charifson et al. | |
| 8,471,014 B2 | 6/2013 | Shannon et al. | |
| 8,476,281 B2* | 7/2013 | Shannon et al. | 514/256 |
| 8,481,551 B2* | 7/2013 | Le Tiran et al. | 514/256 |
| 8,481,552 B2* | 7/2013 | Shannon et al. | 514/256 |
| 2003/0119868 A1 | 6/2003 | Grillot et al. | |
| 2004/0043989 A1 | 3/2004 | Grillot et al. | |
| 2004/0235886 A1 | 11/2004 | Charifson et al. | |
| 2005/0038247 A1 | 2/2005 | Charifson et al. | |
| 2005/0256136 A1 | 11/2005 | Charifson et al. | |
| 2006/0025424 A1 | 2/2006 | Charifson et al. | |
| 2006/0122196 A9 | 6/2006 | Charifson et al. | |
| 2008/0132546 A1 | 6/2008 | Basarab et al. | |
| 2009/0176771 A1 | 7/2009 | Charifson et al. | |
| 2009/0197877 A1 | 8/2009 | Haydon et al. | |
| 2009/0325935 A1 | 12/2009 | Charifson et al. | |
| 2009/0325955 A1 | 12/2009 | Charifson et al. | |
| 2010/0063069 A1 | 3/2010 | Charifson et al. | |
| 2010/0105701 A1 | 4/2010 | Charifson et al. | |
| 2010/0311766 A1 | 12/2010 | Haydon et al. | |
| 2011/0104207 A1 | 5/2011 | Charifson et al. | |
| 2011/0166088 A1 | 7/2011 | Sattigeri et al. | |
| 2011/0263590 A1 | 10/2011 | Haydon et al. | |
| 2012/0004221 A1 | 1/2012 | Haydon et al. | |
| 2012/0010222 A1 | 1/2012 | Charifson et al. | |
| 2012/0184512 A1 | 7/2012 | Le Tiran et al. | |
| 2012/0184564 A1* | 7/2012 | Shannon et al. | 514/256 |
| 2012/0184741 A1* | 7/2012 | Shannon et al. | 544/333 |
| 2012/0184742 A1* | 7/2012 | Shannon et al. | 544/333 |
| 2013/0157979 A1* | 6/2013 | Bennani et al. | 514/80 |
| 2013/0261305 A1 | 10/2013 | Shannon et al. | |
| 2013/0267540 A1* | 10/2013 | Shannon et al. | 514/256 |
| 2013/0317222 A1* | 11/2013 | Shannon et al. | 544/333 |
| 2014/0031318 A1* | 1/2014 | O'Dowd et al. | 514/80 |
| 2014/0045791 A1* | 2/2014 | Locher et al. | 514/80 |

FOREIGN PATENT DOCUMENTS

| | | |
|---|---|---|
| EP | 1055668 | 11/2000 |
| WO | WO 99/35155 | 7/1999 |
| WO | WO 00/49015 | 8/2000 |
| WO | WO 00/71522 | 11/2000 |
| WO | WO 02/060879 | 8/2002 |
| WO | WO 03/105846 | 12/2003 |
| WO | WO 2005/012292 | 10/2005 |
| WO | WO 2006/022773 | 3/2006 |
| WO | WO 2007/056330 | 5/2007 |
| WO | WO 2007/148093 | 12/2007 |
| WO | WO 2008/068470 | 6/2008 |
| WO | WO 2009/074810 | 6/2009 |
| WO | WO 2009/074812 | 6/2009 |
| WO | WO 2009/156966 | 12/2009 |
| WO | WO 2011/032050 | 3/2011 |
| WO | WO 2011/047323 | 4/2011 |
| WO | WO 2012/045124 | 4/2012 |
| WO | WO 2012/097269 | 7/2012 |
| WO | WO 2012/097270 | 7/2012 |
| WO | WO 2012/097273 | 7/2012 |
| WO | WO 2012/177707 | 12/2012 |
| WO | WO 2013/138860 | 9/2013 |

OTHER PUBLICATIONS

Joseph E. Drumm et al., "Facile preparation of fused ring azolylureas," 48 Tetrahedron Lett. 5535-5538 (2007).
Stephen P. East et al., "DNA gyrase (GyrB)/topoisomerase IV (ParE) inhibitors," 19 Bioorg. Med. Chem. Lett. 894-899 (2009).
Eckert et al., "The antifungal activity of . . . " CA 93:39290 (1980).
Gershman in The Medical Reporter, 1997.
Guven et al. "Synthesis and Antimicrobial Activity of Some Novel Furyl and Benzimidazole Substituted Benzyl Ethers" Journal of Heterocyclic Chemistry 2007, 44, 731.
He et al. "Synthesis and biological evaluation of novel benzimidazoles as potential antibacterial agents." Bioorganic & Medicinal Chemistry Letters 2004, 14, 1217-1220.
Hubschwerlen et al., "Pyrimido[1,6-1]benzimidazoles: A New Class of DNA Gyrase Inhibitors" J. Med. Chem, vol. 35, No. 8, pp. 1385-1392, 1992.
International Search Report and Written Opinion of the International Searching Authority, International Patent Application No. PCT/US2012/021270 (Mar. 16, 2012).
International Search Report and Written Opinion of the International Searching Authority, International Patent Application No. PCT/US2012/021281 (May 3, 2012).
International Search Report and Written Opinion of the International Searching Authority, International Patent Application No. PCT/US2012/021280 (Mar. 23, 2012).
International Search Report and Written Opinion of the International Searching Authority, International Patent Application No. PCT/US2012/021275 (Mar. 23, 2012).
Kornberg and Baker, DNA Replication, 2d Ed., Chapter 12, 1992, W. H. Freeman and Co.
Kus, C., "Synthesis and Antimicrobial Activities of 5-fluoro-1, 2, 6-trisubstituted benzimidazole carboxamide and acetamide derivatives," Arch. Pharm. Pharm. Med. Chem. 334(11):361-365 (2001).
Levy, "The Challenge of Antibiotic Resistance", Scientific American, Mar. 1998).
Lewis, "The Rise of Antibiotic-Resistant Infections", FDA Consumer magazine, Sep. 1995.
Maxwell, Mol. Microbiol., 1993, 9, 681.
Maxwell, Trends in Microbiology, 1997, 5, 102.
MayoClinic "Antibiotic associated diarrhea" Mayoclinic.com. (2007).
Nicolaus B.J.R., "Symbiotic Approach to Drug Design," Decision Making in Drug Research, pp. 173-186 (1983).
Pea et al., PubMed Abstract (Clin Pharmacokinet. 44(10):1009-34) 2005.
Singh, S.K., et al., "Studies in antiparastic agents: Part 13—Synthtesis of 4-aryl-2-substitutedamino-thiazoles as potential anthelmintics," Indian J. Chem., 28B (9):786-789 (1989).
Skopenka, V.V., et al., "Organotin Carbamoyldicyanomethanide, nitrosocarbamoylcyanomethanide, and Carbamoylcyanides," retrieved from STN Database accession No. 101:230674, XP002254350 abstract and Dopovidi Akademii Nauk Ukrains'Koi RSR, Seriya B: Geologichni, Khimichni Ta Biologichni Nauki, 7:44-46 (1984).
Snyder et al., PubMed Abstract (J. Med Liban. 48(4):208-14), Jul.-Aug. 2000.
Sun et al., "Synthesis and Evaluation of Terbenzimidazoles as Topoisomerase I Inhibitors" J. Med. Chem., vol. 38, No. 18, pp. 3638-3644, 1995.
Tanitame et al. "Design, synthesis and structure-activity relationship studies of novel indazole analogues as DNA gyrase inhibitors with Gram-positive antibacterial activity" Bioorganic & Medicinal Chemistry Letters 2004, 14, 2857-2862.
Drlica, Molecular Microbiology, 1992, 6, 425.
Wassenaar "Bacteria; more than pathogens" Am. Ins. Biol. Sci. Internet p. 1-7 (2002).
Webster's Dictionary (1984) p. 933.
WHO Report, "Use of Quinolones in Food Animals and Potential Impact on Human Health", 1998.

(56) References Cited

OTHER PUBLICATIONS

International Search Report and Written Opinion of the International Searching Authority, International Patent Application No. PCT/US2012/043266 (Aug. 28, 2012).
International Search Report and Written Opinion of the International Searching Authority, International Patent Application No. PCT/US2012/051008 (Oct. 14, 2013).
International Search Report and Written Opinion of the International Searching Authority, International Patent Application No. PCT/US2012/050564 (Oct. 8, 2013).
Silke Alt, Lesley A. Mitchenall, Anthony Maxwell, and Lutz Heide, "Inhibition of DNA gyrase and DNA topoisomerase IV of *Staphylococcus aureaus* and *Escherichia coli* by aminocoumarin antibiotics," *Journal of Antimicrobial Chemotherapy* 66; pp. 2061-2069; (2011).
Barton J. Bradbury and Michael J. Pucci, "Recent advances in bacterial topoisomerase inhibitors," *Current Opinion in Pharmacology* 8, pp. 574-581; (2008).
Chabner, Bruce A. et al., "Antineoplastic Agents," *The Pharmacological Basics of Therapeutics* 11th edition, Chapter 51; pp. 1315-1403; (2006).
Poupaert, Jacques H., "Drug Design: Basic Principles and Application," *Encyclopedia of Pharmaceutical Technology*; pp. 1362-1369; (2007).
Akihiko Tanitame et al., "Synthesis and Antibacterial Activity of Novel Series of Potent DNA Gyrase Inhibitors. Pyrazole Derivatives," *J. Med. Chem.* 47; pp. 3693-3696; (2004).

\* cited by examiner

GYRASE AND TOPOISOMERASE IV INHIBITORS

CROSS REFERENCE TO RELATED APPLICATIONS

This application is a continuation of U.S. application Ser. No. 13/349,789, filed on filed on Jan. 13, 2012, U.S. Pat. No. 8,481,551, which claims the benefit under 35 U.S.C. §119 of U.S. Provisional Patent Application Ser. No. 61/432,965 filed Jan. 14, 2011; of U.S. Provisional Patent Application Ser. No. 61/515,174 filed Aug. 4, 2011; of U.S. Provisional Patent Application Ser. No. 61/515,249 filed Aug. 4, 2011; and of U.S. Provisional Patent application Ser. No. 61/449,134 filed Jun. 20, 2011; the contents of each application hereby incorporated by reference.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis*, and *Enterococcus*. The appearance of Vancomycin resistant *enterococcus* was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., Current Opinion in Anti-infective Investigational Drugs, 1999, 1, 1; Levy, "The Challenge of Antibiotic Resistance", Scientific American, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in The Medical Reporter, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", FDA Consumer magazine, September 1995).

As a result of the need to combat drug-resistant bacteria and the increasing failure of the available drugs, there has been a resurgent interest in discovering new antibiotics. One attractive strategy for developing new antibiotics is to inhibit DNA gyrase and/or topoisomerase IV, bacterial enzymes necessary for DNA replication, and therefore, necessary for bacterial cell growth and division. Gyrase and/or topoisomerase IV activity are also associated with events in DNA transcription, repair and recombination.

Gyrase is one of the topoisomerases, a group of enzymes which catalyze the interconversion of topological isomers of DNA (see generally, Kornberg and Baker, DNA Replication, 2d Ed., Chapter 12, 1992, W.H. Freeman and Co.; Drlica, Molecular Microbiology, 1992, 6, 425; Drlica and Zhao, Microbiology and Molecular Biology Reviews, 1997, 61, pp. 377-392). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase and/or topoisomerase IV would be selective for these enzymes and be relatively inactive against the eukaryotic type II topoisomerases.

Topoisomerase IV primarily resolves linked chromosome dimers at the conclusion of DNA replication.

The widely-used quinolone antibiotics inhibit bacterial DNA gyrase (GyrA) and/or Topoisomerase IV (ParC). Examples of the quinolones include the early compounds such as nalidixic acid and oxolinic acid, as well as the later, more potent fluoroquinolones such as norfloxacin, ciprofloxacin, and trovafloxacin. These compounds bind to GyrA and/or ParC and stabilize the cleaved complex, thus inhibiting overall gyrase function, leading to cell death. The fluoroquinolones inhibit the catalytic subunits of gyrase (GyrA) and/or Topoisomerase IV (Par C) (see Drlica and Zhao, Microbiology and Molecular Biology Reviews, 1997, 61, 377-392). However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

The associated subunits responsible for supplying the energy necessary for catalytic turnover/resetting of the enzymes via ATP hydrolysis are GyrB (gyrase) and ParE (topoisomerase IV), respectively (see, Champoux, J. J., Annu. Rev. Biochem., 2001, 70, pp. 369-413). Compounds that target these same ATP binding sites in the GyrB and ParE subunits would be useful for treating various bacterial infections (see, Charifson et al., J. Med. Chem., 2008, 51, pp. 5243-5263).

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, Trends in Microbiology, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, Mol. Microbiol., 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, Trends in Microbiology, 1997, 5, 102). It would be desirable to have a new, effective GyrB and ParE inhibitor that overcomes these drawbacks and, preferably does not rely on binding to Arg136 for activity. Such an inhibitor would be an attractive antibiotic candidate, without a history of resistance problems that plague other classes of antibiotics.

As bacterial resistance to antibiotics has become an important public health problem, there is a continuing need to develop newer and more potent antibiotics. More particularly, there is a need for antibiotics that represent a new class of compounds not previously used to treat bacterial infection. Compounds that target the ATP binding sites in both the GyrB (gyrase) and ParE (topoisomerase IV) subunits would be useful for treating various bacterial infections. Such compounds would be particularly useful in treating nosocomial infections in hospitals where the formation and transmission of resistant bacteria are becoming increasingly prevalent. Furthermore, there is a need for new antibiotics having a broad spectrum of activity with advantageous toxicological properties.

SUMMARY OF THE INVENTION

The present invention is directed to compounds and pharmaceutically acceptable salts thereof, useful as gyrase and/or topoisomerase IV inhibitors. The gyrase and/or topoisomerase IV inhibitors of the present invention may be represented by formula (I) or salts thereof:

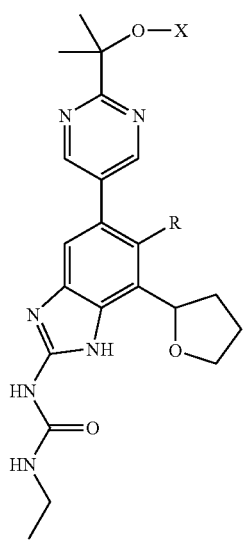

(I)

wherein R is hydrogen or fluorine; X is hydrogen, —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation. The compounds of formula (I) either possess a broad range of anti-bacterial activity and advantageous toxicological properties or are prodrugs of compounds having said activity.

The present invention also relates to compounds of formula (IA), or pharmaceutically acceptable salts thereof, useful as gyrase and/or topoisomerase IV inhibitors. The compounds of formula (IA) are encompassed by formula (I). The compounds of formula (IA) may be represented as:

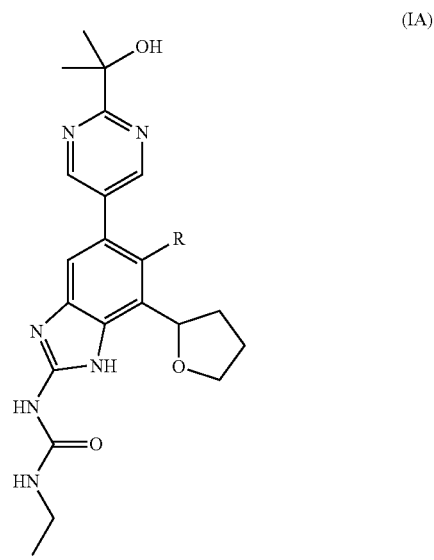

(IA)

wherein R is hydrogen or fluorine. The compounds of formula (IA) possess a broad range of anti-bacterial activity and advantageous toxicological properties.

The present invention also relates to compounds of formula (IB), or pharmaceutically acceptable salts thereof, useful as prodrugs for gyrase and/or topoisomerase IV inhibitors. The compounds of formula (IB) are encompassed by formula (I). The compounds of formula (IB) may be represented as:

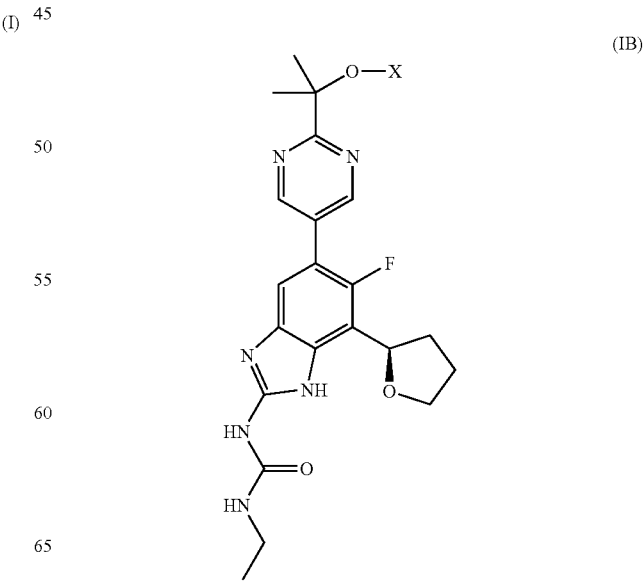

(IB)

wherein X is —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation. The compounds of formula (IB) are phosphate ester prodrugs of the compound (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, which possesses a broad range of anti-bacterial activity and advantageous toxicological properties. In addition to the compounds provided herein, the present invention further provides a pharmaceutical composition comprising a compound of formula (I) (which includes other formulae encompassed by formula (I) such as formulae (IA), (IB), (IC) and (ID)) or a pharmaceutically acceptable salt thereof and a pharmaceutically acceptable carrier.

In another embodiment, the present invention relates to a pharmaceutical composition comprising a compound of formula (I) or a pharmaceutically acceptable salt thereof, a pharmaceutically acceptable carrier, and an additional therapeutic agent selected from an antibiotic, an anti-inflammatory agent, a matrix metalloproteinase inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

In another embodiment, the present invention relates to a method of treating a bacterial infection in a mammal in need thereof, comprising administering to said mammal a therapeutically effective amount of a compound of formula (I) or a pharmaceutically acceptable salt thereof.

In a further embodiment, the present invention relates to a method of treating a bacterial infection in a mammal in need thereof, comprising administering to said mammal a therapeutically effective amount of a compound of formula (I) or a pharmaceutically acceptable salt thereof and an antibiotic, an anti-inflammatory agent, a matrix metalloproteinase inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound, either as part of a multiple dosage form together with said compound or as a separate dosage form.

DETAILED DESCRIPTION

Figure 1:
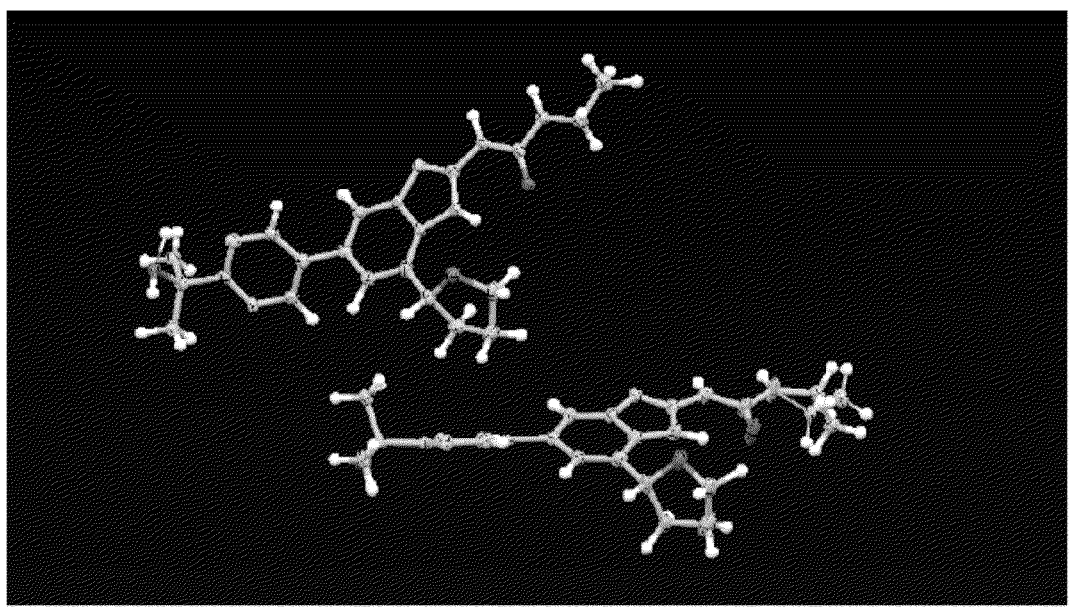
FIG. 1 is a thermal ellipsoid plot of two symmetry independent molecules of compound 12.

As used herein, the term "halogen" means F, Cl, Br, or I.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Isotopically-labeled forms of compounds of formula (I) wherein one or more atoms are replaced by an atom having an atomic mass or mass number different from the atomic mass or mass number usually found in nature are also included herein. Examples of isotopes that can be incorporated into compounds of the invention include isotopes of hydrogen, carbon, nitrogen, oxygen, and fluorine, such as $^2$H, $^3$H, $^{13}$C, $^{14}$C, $^{15}$N, $^{18}$O, and $^{17}$O. Such radio-labeled and stable-isotopically labeled compounds are useful, for example, as research or diagnostic tools or gyrase and/or topoisomerase IV inhibitors with improved therapeutic profile. The structures also encompass zwitterionic forms of the compounds or salts, where appropriate.

In one embodiment, compounds of formula (I) include compounds of formula (IC)

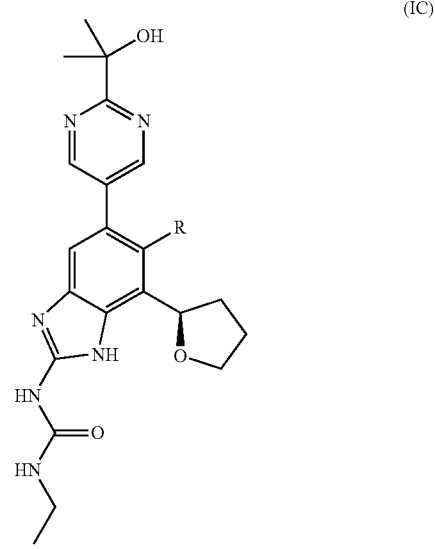

(IC)

wherein R is as defined above.

In another embodiment, compounds of formula (I) include compounds of formulae (ID) and (IE) as set forth below:

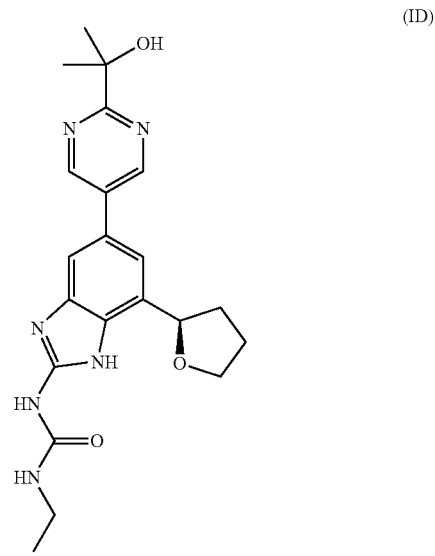 [SMILES: CCNC(=O)Nc1nc2cc(-c3cnc(C(C)(C)O)nc3)cc([C@H]3CCCO3)c2[nH]1]

(ID)

(R)-1-ethyl-3-(5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof; and (IE)

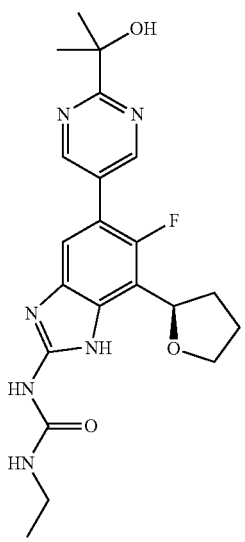

(R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof. Unless otherwise stated, the phrase "compounds of formula (I)" is intended to include other formulae set forth herein that are encompassed by formula (I) including formulae (IA), (IB), (IC), (ID), and (IE).

The compounds of formula (IB) are prodrugs of their parent compound, 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea. Thus, the activity exhibited upon administration of the prodrug is principally due to the presence of the parent compound that results from cleavage of the prodrug.

The term "prodrug" refers to compounds which are drug precursors which, following administration and absorption, release the drug in vivo via some metabolic process. In general, a prodrug possesses less biological activity than its parent drug. A prodrug may also improve the physical properties of the parent drug and/or it may also improve overall drug efficacy, for example through the reduction of toxicity and unwanted effects of a drug by controlling its absorption, blood levels, metabolic distribution and cellular uptake.

The term "parent compound" or "parent drug" refers to the biologically active entity that is released via enzymatic action of a metabolic or a catabolic process, or via a chemical process following administration of the prodrug. The parent compound may also be the starting material for the preparation of its corresponding prodrug.

The monovalent cations defined by $M^+$ include ammonium, alkali metal ions such as sodium, lithium and potassium ions, dicyclohexylamine ion, and N-methyl-D-glucamine ion. The divalent cations defined by $D^{2+}$ include, alkaline earth metal ions such as aluminum, calcium and magnesium ions. Also included are amino acid cations such as ions of arginine, lysine, ornithine, and so forth. If $M^+$ is a monovalent cation, it is recognized that if the definition $2M^+$ is present, each of $M^+$ may be the same or different. In addition, it is similarly recognized that if the definition $2M^+$ is present, a divalent cation $D^{2+}$ may instead be present. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others.

Various embodiments of the invention, include compounds or salts of formula (IB) as set forth below:
(1) compounds wherein X is
  (a) —PO(OH)O$^-$M$^+$;
  (b) —PO(O$^-$)$_2$.2M$^+$; or
  (c) —PO(O$^-$)$_2$.D$^{2+}$;
(2) compounds wherein $M^+$ is
  (a) Li$^+$, Na$^+$, K$^+$, N-methyl-D-glucamine, or N(R$^9$)$_4^+$; or
  (b) Na$^+$;
  (c) each R$^9$ is independently hydrogen or a $C_1$-$C_4$ alkyl group;
(3) compounds wherein $D^{2+}$ is
  (a) Mg$^{2+}$, Ca$^{2+}$, and Ba$^{2+}$; or
  (b) Ca$^{2+}$;
(4) the compound (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate; and
(5) the compound disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate.

It is understood that various alternative embodiments of the compounds or salts of formula (OB) can be selected by requiring one or more of the alternate embodiments listed in (1) through (3) above. For example, further embodiments of the invention can be obtained by combining (1)(a) and (2)(a); (1)(a) and (2)(b); (1)(c) and (3)(a); (1)(c) and (3)(b); (1)(b) and (2)(a); (1)(b) and (2)(b); and the like.

The prodrugs of the present invention are characterized by unexpectedly high aqueous solubility. This solubility facilitates administration of higher doses of the prodrug, resulting in a greater drug load per unit dosage.

One embodiment of this invention relates to a method of treating a bacterial infection in a mammal in need thereof, comprising administering to said mammal a therapeutically effective amount of a compound having the formula (I) or a pharmaceutically acceptable salt thereof.

According to another embodiment, the invention provides a method of decreasing or inhibiting bacterial quantity in a biological sample. This method comprises contacting said biological sample with a compound of formula (I) or a pharmaceutically acceptable salt thereof.

The term "biological sample", as used herein, includes cell cultures or extracts thereof; biopsied material obtained from a mammal or extracts thereof; and blood, saliva, urine, feces, semen, tears, or other body fluids or extracts thereof. The term "biological sample" also includes living organisms, in which case "contacting a compound of this invention with a biological sample" is synonymous with the term "administering said compound or composition comprising said compound) to a mammal".

One embodiment comprises contacting said biological sample with a compound selected from the group consisting of (R)-1-ethyl-3-(5-(2-(2-hydroxypropan-2-yl)pyrimidin-5-yl)-7-(tetrahydrofuran-2-yl)-1H-benzo[d]imidazol-2-yl) urea, or a pharmaceutically acceptable salt thereof; and (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl) urea, or a pharmaceutically acceptable salt thereof. Pharmaceutical compositions useful for such methods are described below.

One embodiment comprises contacting said biological sample with a phosphate ester prodrug of (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, as defined by formula (IB). Pharmaceutical compositions useful for such methods are described below.

The antimicrobial activity of the compounds of formula (I) may be demonstrated in an antimicrobial susceptibility assay. The details of the conditions used for the antimicrobial susceptibility assays are set forth in the Examples below.

The gyrase and/or topoisomerase IV inhibitors of this invention, or pharmaceutical salts thereof, may be formulated into pharmaceutical compositions for administration to animals or humans. These pharmaceutical compositions effective to treat or prevent a bacterial infection which comprise the gyrase and/or topoisomerase IV inhibitor in an amount sufficient to measurably decrease bacterial quantity and a pharmaceutically acceptable carrier, are another embodiment of the present invention. The term "measurably decrease bacterial quantity", as used herein means a measurable change in the number of bacteria between a sample containing said inhibitor and a sample containing only bacteria.

Agents which increase the susceptibility of bacterial organisms to antibiotics are known. For example, U.S. Pat. Nos. 5,523,288, 5,783,561 and 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in Microbiological Reviews (1992) pp. 395-411, and the sensitization of gram-negative bacteria has been described by Tsubery, H., et al, in J. Med. Chem. (2000) pp. 3085-3092.

Another embodiment of this invention relates to a method, as described above, of preventing, controlling, treating or reducing the advancement, severity or effects of a bacterial infection in a mammal in need thereof, but further comprising the step of administering to said mammal an agent which increases the susceptibility of bacterial organisms to antibiotics.

According to another embodiment, the methods of the present invention are useful to treat patients in the veterinarian field including, but not limited to, zoo, laboratory, human companion, and farm animals including primates, rodents, reptiles and birds. Examples of said animals include, but are not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, ostriches, chickens, turkeys, ducks, and geese.

The pharmaceutical compositions and methods of this invention will be useful generally for controlling bacterial infections in vivo. Examples of bacterial organisms that may be controlled by the compositions and methods of this invention include, but are not limited to the following organisms: *Streptococcus pneumoniae, Streptococcus pyogenes, Enterococcus faecalis, Enterococcus faecium, Klebsiella pneumoniae, Enterobacter* spp. *Proteus* spp. *Pseudomonas aeruginosa, E. coli, Serratia marcescens, Staphylococcus aureus*, Coag. Neg. Staphylococci, *Haemophilus influenzae, Bacillus anthraces, Mycoplasma pneumoniae, Moraxella catarrhalis, Chlamydophila pneumoniae, Chlamydia trachomatis, Legionella pneumophila, Mycobacterium tuberculosis, Helicobacter pylori, Staphylococcus saprophyticus, Staphylococcus epidermidis, Francisella tularensis, Yersinia pestis, Clostridium difficile, Neisseria gonorrhoeae, Neisseria meningitidis, Mycobacterium avium* complex, *Mycobacterium abscessus, Mycobacterium kansasii* and *Mycobacterium ulcerans.*

The compositions and methods will therefore be useful for controlling, treating or reducing the advancement, severity or effects of nosocomial or non-nosocomial infections. Examples of nosocomial and non-nosocomial infections include but are not limited to upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections. Examples of specific bacterial infections include but are not limited to uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial *pneumoniae* (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

The term "non-nosocomial infections" is also referred to as community acquired infections.

In one embodiment, the compositions and methods will therefore be useful for controlling, treating or reducing the advancement, severity or effects of community-acquired bacterial *pneumoniae* (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

In another embodiment, the compositions and methods will therefore be useful for controlling, treating or reducing the advancement, severity or effects of upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial *pneumoniae* (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

In another embodiment, the bacterial infection is characterized by the presence of one or more of *Streptococcus pneumoniae, Streptococcus pyogenes, Enterococcus faecalis, Enterococcus faecium, Staphylococcus aureus*, Coag. Neg. Staphlococci, *Bacillus anthraces, Staphylococcus epidermidis, Staphylococcus saprophyticus*, or *Mycobacterium tuberculosis*.

In another embodiment, the bacterial infection is characterized by the presence of one or more of *Streptococcus pneumoniae, Enterococcus faecalis*, or *Staphylococcus aureus*.

In another embodiment, the bacterial infection is characterized by the presence of one or more of *E. coli, Moraxella catarrhalis*, or *Haemophilus influenzae*.

In another embodiment, the bacterial infection is characterized by the presence of one or more of *Clostridium difficile, Neisseria gonorrhoeae, Neisseria meningitidis, Mycobacterium avium* complex, *Mycobacterium abscessus, Mycobacterium kansasii, Mycobacterium ulcerans, Chlamydophila pneumoniae* and *Chlamydia tracomatis*.

In another embodiment, the bacterial infection is characterized by the presence of one or more of *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium complex, Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci.

In some embodiments, the bacterial infection is characterized by the presence of one or more of Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant Coagulase negative staphylococcus, Fluoroquinolone resistant Coagulase negative *staphylococcus*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, Vancomycin resistant *staphylococcus epidermidis*, Fluoroquinolone resistant *Neisseria gonorrhoeae*, Multidrug Resistant *Pseudomonas aeruginosa* or Cephalosporin resistant *Neisseria gonorrhoeae*.

According to another embodiment, the Methicillin resistant Staphylococci are selected from Methicillin resistant *Staphylococcus aureus*, Methicillin resistant *Staphylococcus epidermidis*, or Methicillin resistant Coagulase negative *staphylococcus*.

In some embodiments, a form of a compound of formula (I) is used to treat community acquired MRSA (i.e., cMRSA).

In other embodiments, a form of a compound of formula (I) is used to treat daptomycin resistant organism including, but not limited to, daptomycin resistant *Enterococcus faecium* and daptomycin resistant *Staphylococcus aureus*.

According to another embodiment, the Fluoroquinolone resistant Staphylococci are selected from Fluoroquinolone resistant *Staphylococcus aureus*, Fluoroquinolone resistant *Staphylococcus epidermidis*, or Fluoroquinolone resistant Coagulase negative *staphylococcus*.

According to another embodiment, the Glycopeptide resistant Staphylococci are selected from Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, or Hetero vancomycin resistant *Staphylococcus aureus*.

According to another embodiment, the Macrolide-Lincosamide-Streptogramin resistant Staphylococci is Macrolide-Lincosamide-Streptogramin resistant *Staphylococcus aureus*.

According to another embodiment, the Linezolid resistant Enterococciare selected from Linezolid resistant *Enterococcus faecalis*, or Linezolid resistant *Enterococcus faecium*.

According to another embodiment, the Glycopeptide resistant Enterococci are selected from Vancomycin resistant *Enterococcus faecium* or Vancomycin resistant *Enterococcus faecalis*.

According to another embodiment, the β-lactam resistant *Enterococcus faecalis* is β-lactam resistant *Enterococcus faecium*.

According to another embodiment, the Penicillin resistant Streptococci is Penicillin resistant *Streptococcus pneumoniae*.

According to another embodiment, the Macrolide resistant Streptococci is Macrolide resistant *Streptococcus pneumonia*.

According to another embodiment, the Ketolide resistant Streptococci are selected from Macrolide resistant *Streptococcus pneumoniae* and Ketolide resistant *Streptococcus pyogenes*.

According to another embodiment, the Fluoroquinolone resistant Streptococci is Fluoroquinolone resistant *Streptococcus pneumoniae*.

According to another embodiment, the β-lactam resistant Haemophilus is β-lactam resistant *Haemophilus influenzae*.

According to another embodiment, the Fluoroquinolone resistant Haemophilus is Fluoroquinolone resistant *Haemophilus influenzae*.

According to another embodiment, the Macrolide resistant Haemophilus is Macrolide resistant *Haemophilus influenzae*.

According to another embodiment, the Macrolide resistant Mycoplasma is Macrolide resistant *Mycoplasma pneumoniae*.

According to another embodiment, the Isoniazid resistant Mycobacterium is Isoniazid resistant *Mycobacterium tuberculosis*.

According to another embodiment, the Rifampin resistant Mycobacterium is Rifampin resistant *Mycobacterium tuberculosis*.

According to another embodiment, the β-lactam resistant *Moraxella* is β-lactam resistant *Moraxella catarrhalis*.

According to another embodiment, the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Fluoroquinolone resistant *Neisseria gonorrhoeae* or Cephalosporin resistant *Neisseria gonorrhoeae*.

According to another embodiment, the bacterial infection is characterized by the presence of one or more of the following: Methicillin resistant *Staphylococcus aureus*, Methicillin resistant *Staphylococcus epidermidis*, Methicillin resistant Coagulase negative *staphylococcus*, Fluoroquinolone resistant *Staphylococcus aureus*, Fluoroquinolone resistant *Staphylococcus epidermidis*, Fluoroquinolone resistant Coagulase negative *staphylococcus*, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, or β-lactam resistant *Haemophilus influenzae*.

According to another embodiment, the bacterial infection is characterized by the presence of one or more of the following: Methicillin resistant *Staphylococcus aureus*, Vancomycin resistant *Enterococcus faecium*, Vancomycin resistant *Enterococcus faecalis*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Multidrug Resistant *Pseudomonas aeruginosa*, Isoniazid resistant *Mycobacterium tuberculosis*, and Rifampin resistant *Mycobacterium tuberculosis*.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Pharmaceutical compositions of this invention comprise a compound of formula (I) or a pharmaceutically acceptable salt thereof and a pharmaceutically acceptable carrier. Such compositions may optionally comprise an additional therapeutic agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an antiviral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as alpha-tocopherol, polyethyleneglycol 1000 succinate, or other similar polymeric delivery matrices.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

Depending upon the particular condition, or disease state, to be treated or prevented, additional therapeutic agents, which are normally administered to treat or prevent that condition, may be administered together with the inhibitors of this invention. Such therapeutic agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. In one embodiment, the compounds of this invention may be used in compositions and methods for treating or protecting individuals against bacterial infections or diseases over a 1-2 week period. In another embodiment, the compounds of this invention may be used in compositions and methods for treating or protecting individuals against bacterial infections or diseases over a 4-8 week period (for example, in the treatment of patients with or at risk for developing endocarditis or osteomyelitis). In another embodiment, the compounds of this invention may be used in compositions and methods for treating or protecting individuals against bacterial infections or diseases over an 8-12 week period. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

In some embodiments, compounds of formula (I) may be used prophylactically to prevent a bacterial infection. In some embodiments, compounds of formula (I) may be used before, during or after a dental or surgical procedure to prevent opportunistic infections such as those encountered in bacterial endocarditis. In other embodiments, compounds of formula (I) may be used prophylactically in dental procedures, including but not limited to extractions, periodontal procedures, dental implant placements and endodontic surgery. In other embodiments, compounds of formula (I) may be used prophylactically in surgical procedures including but not limited to general surgery, respiratory surgery (tonsillectomy/adenoidectomy), gastrointestinal surgery (upper GI and elective small bowel surgery, esophageal sclerotherapy and dilation, large bowel resections, acute appendectomy), trauma surgery (penetrating abdominal surgery), genito-urinary tract surgery (prostatectomy, urethral dilation, cystoscopy, vaginal or abdominal hysterectomy, cesarean section), transplant surgery (kidney, liver, pancreas or kidney transplantation), head and neck surgery (skin excisions, neck dissections, laryngectomy, head and neck cancer surgeries, mandibular fractures), orthopaedic surgery (total joint replacement, traumatic open fractures), vascular surgery (peripheral vascular procedures), cardiothoracic surgery, coronary bypass surgery, pulmonary resection and neurosurgery.

The term "prevent a bacterial infection" as used herein, unless otherwise indicated, means the prophylactic use of an antibiotic, such as a gyrase and/or topoisomerase IV inhibitor of the present invention, to prevent a bacterial infection. Treatment with a gyrase and/or topoisomerase IV inhibitor could be done prophylactically to prevent an infection caused by an organism that is susceptible to the gyrase and/or topoisomerase IV inhibitor. One general set of conditions where prophylactic treatment could be considered is when an individual is more vulnerable to infection due to, for example, weakened immunity, surgery, trauma, presence of an artificial device in the body (temporary or permanent), an anatomical defect, exposure to high levels of bacteria or possible exposure to a disease-causing pathogen. Examples of factors that could lead to weakened immunity include chemotherapy, radiation therapy, diabetes, advanced age, HIV infection, and transplantation. An example of an anatomical defect would be a defect in the heart valve that increases the risk of bacterial endocarditis. Examples of artificial devices include artificial joints, surgical pins, catheters, etc. Another set of situations where prophylactic use of a gyrase and/or topoisomerase IV inhibitor might be appropriate would be to prevent the spread of a pathogen between individuals (direct or indirect). A specific example of prophylactic use to prevent the spread of a pathogen is the use of a gyrase and/or topoisomerase IV inhibitor by individuals in a healthcare institution (for example a hospital or nursing home).

The compounds of formula (I) may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula (I) and another therapeutic or prophylactic agent.

In some embodiments, the additional therapeutic agent or agents is an antibiotic selected from a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide.

In some embodiments, the additional therapeutic agent or agents is an antibiotic selected from a penicillin, a cephalosporin, a quinolone, an aminoglycoside or an oxazolidinone.

In other embodiments, the additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/ tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, Ceftaroline and Ceftobiprole, from a Cephamycin including Cefotetan and Cefoxitin, from a carbapenem including Doripenem, Imipenem and Meropenem, from a monobactam including Aztreonam, from a quinolone including Cinoxacin, Nalidixic acid, Oxolininc acid and Pipemidic acid, from a fluoroquinolone including Besifloxacin, Ciprofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Dalbavancin, Telavancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, colistin, Tygacil, Daptomycin, chloramphenicol, clindamycin, isoniazid, metronidazole, mupirocin, polymyxin B, pyrazinamide, trimethoprim/sulfamethoxazole and sulfisoxazole.

In other embodiments, the additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a carbapenem including Imepenem, Meropenem, Ertapenem, Doripenem, Panipenem and Biapenem, a fluoroquinolone including Ciprofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including Vancomycin, from a Rifamycin including Rifampin and from other antibiotics including isoniazid, pyrazinamide, Tygacil, Daptomycin or trimethoprim/sulfamethoxazole.

In some embodiments, a solid form of a compound of formula (I), can be administered for the treatment of a gram positive infection. In some embodiments, the composition is a solid, liquid (e.g., a suspension), or an iv (e.g., a form of the formula (I) compound is dissolved into a liquid and administered iv) composition. In some embodiments, the composition including a formula (I) compound, is administered in combination with an additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide. In some embodiments, the composition including a solid form of a formula (I) compound is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide is administered iv.

In some embodiments, a solid form of a formula (I) compound, can be administered for the treatment of a gram negative infection. In some embodiments, the composition is a solid, liquid (e.g., a suspension), or an iv (e.g., a form of a formula (I) compound is dissolved into a liquid and administered iv) composition. In some embodiments the composition including a formula (I) compound is administered in combination with an additional antibiotic agent, selected from a: natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a polymyxin, tetracycline or a sulfonamide. In some embodiments, the composition including a solid form of a formula (I) compound is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a polymyxin, tetracycline or a sulfonamide is administered orally. In some embodiments, the additional therapeutic agent is administered iv.

The additional therapeutic agents described above may be administered separately, as part of a multiple dosage regimen, from the inhibitor-containing composition. Alternatively, these agents may be part of a single dosage form, mixed together with the inhibitor in a single composition.

The pharmaceutical compositions of this invention may be administered orally, parenterally, by inhalation spray, topically, rectally, nasally, buccally, vaginally or via an implanted reservoir. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical, compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

According to another embodiment, compounds of formula (I) may also be delivered by implantation (e.g., surgically), such as with an implantable or indwelling device. An implantable or indwelling device may be designed to reside either permanently or temporarily in a subject. Examples of implantable and indwelling devices include, but are not limited to, contact lenses, central venous catheters and needleless connectors, endotracheal tubes, intrauterine devices, mechanical heart valves, pacemakers, peritoneal dialysis catheters, prosthetic joints, such as hip and knee replacements, tympanostomy tubes, urinary catheters, voice prostheses, stents, delivery pumps, vascular filters and implantable control release compositions. Biofilms can be detrimental to the health of patients with an implantable or indwelling medical device because they introduce an artificial substratum into the body and can cause persistent infections. Thus, providing compounds of formula (I) in or on the implantable or indwelling device can prevent or reduce the production of a biofilm. In addition, implantable or indwelling devices may be used as a depot or reservoir of compounds of formula (I). Any implantable or indwelling device can be used to deliver compounds of formula (I) provided that a) the device, compounds of formula (I) and any pharmaceutical composition including compounds of formula (I) are biocompatible, and b) that the device can deliver or release an effective amount of compounds of formula (I) to confer a therapeutic effect on the treated patient.

Delivery of therapeutic agents via implantable or indwelling devices is known in the art. See for example, "Recent Developments in Coated Stents" by Hofma et al. published in *Current Interventional Cardiology Reports* 2001, 3:28-36, the entire contents of which, including references cited therein, incorporated herein by reference. Other descriptions of implantable devices can be found in U.S. Pat. Nos. 6,569,195 and 6,322,847; and U.S. Patent Application Numbers 2004/0044405, 2004/0018228, 2003/0229390, 2003/0225450, 2003/0216699 and 2003/0204168, each of which is incorporated herein by reference in its entirety.

In some embodiments, the implantable device is a stent. In one specific embodiment, a stent can include interlocked meshed cables. Each cable can include metal wires for structural support and polymeric wires for delivering the therapeutic agent. The polymeric wire can be dosed by immersing the polymer in a solution of the therapeutic agent. Alternatively, the therapeutic agent can be embedded in the polymeric wire during the formation of the wire from polymeric precursor solutions.

In other embodiments, implantable or indwelling devices can be coated with polymeric coatings that include the therapeutic agent. The polymeric coating can be designed to control the release rate of the therapeutic agent. Controlled release of therapeutic agents can utilize various technologies. Devices are known that have a monolithic layer or coating incorporating a heterogeneous solution and/or dispersion of an active agent in a polymeric substance, where the diffusion of the agent is rate limiting, as the agent diffuses through the polymer to the polymer-fluid interface and is released into the surrounding fluid. In some devices, a soluble substance is also dissolved or dispersed in the polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically have the active agent physically immobilized in the polymer. The active agent can be dissolved and/or dispersed throughout the polymeric material. The polymeric material is often hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

The implantable or indwelling device coating can include a blend of polymers each having a different release rate of the therapeutic agent. For instance, the coating can include a polylactic acid/polyethylene oxide (PLA-PEO) copolymer and a polylactic acid/polycaprolactone (PLA-PCL) copolymer. The polylactic acid/polyethylene oxide (PLA-PEO) copolymer can exhibit a higher release rate of therapeutic agent relative to the polylactic acid/polycaprolactone (PLA-PCL) copolymer. The relative amounts and dosage rates of therapeutic agent delivered over time can be controlled by controlling the relative amounts of the faster releasing polymers relative to the slower releasing polymers. For higher initial release rates the proportion of faster releasing polymer can be increased relative to the slower releasing polymer. If most of the dosage is desired to be released over a long time period, most of the polymer can be the slower releasing polymer. The device can be coated by spraying the device with a solution or dispersion of polymer, active agent, and solvent. The solvent can be evaporated, leaving a coating of polymer and active agent. The active agent can be dissolved and/or dispersed in the polymer. In some embodiments, the co-polymers can be extruded over the device.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections.

Typically, the pharmaceutical compositions of this invention will be administered from about 1 to 5 times per day or alternatively, as a continuous infusion. Alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula (I) and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

According to another embodiment, the invention provides methods for treating or preventing a bacterial infection, or disease state, comprising the step of administering to a patient any compound, pharmaceutical composition, or combination described herein. The term "patient", as used herein, means an animal, preferably a mammal, and most preferably a human.

The compounds of this invention are also useful as commercial reagents which effectively bind to the gyrase B and/or topoisomerase IV enzymes. As commercial reagents, the compounds of this invention, and their derivatives, may be used to block gyrase B and/or topoisomerase IV activity in biochemical or cellular assays for bacterial gyrase B and/or topoisomerase IV or their homologs or may be derivatized to bind to a stable resin as a tethered substrate for affinity chromatography applications. These and other uses which characterize commercial gyrase B and/or topoisomerase IV inhibitors will be evident to those of ordinary skill in the art.

The compounds of this invention may be prepared in accordance with general methods known to those skilled in the art for analogous compounds, as taught by U.S. Pat. Nos. RE 40245 E; 7,495,014 B2; 7,569,591 B2; 7,582,641 B2; 7,618, 974 B2; and 7,727,992 B2. All six of said patents are incorporated by reference as if fully set forth herein. The details of the conditions used for preparing the compounds of the present invention are further set forth in the Examples.

In order that this invention be more fully understood, the following examples are set forth. These examples are for the purpose of illustration only and are not to be construed as limiting the scope of the invention in any way.

The following definitions describe terms and abbreviations used herein:

Ac acetyl
Bu butyl
Et ethyl
Ph phenyl
Me methyl
THF tetrahydrofuran
DCM dichloromethane
$CH_2Cl_2$ dichloromethane
EtOAc ethyl acetate
$CH_3CN$ acetonitrile
EtOH ethanol
$Et_2O$ diethyl ether
MeOH methanol
MTBE methyl tert-butyl ether
DMF N,N-dimethylformamide
DMA N,N-dimethylacetamide
DMSO dimethyl sulfoxide
HOAc acetic acid
TEA triethylamine
TFA trifluoroacetic acid
TFAA trifluoroacetic anhydride
$Et_3N$ triethylamine
DIPEA diisopropylethylamine
DIEA diisopropylethylamine
$K_2CO_3$ potassium carbonate
$Na_2CO_3$ sodium carbonate
$Na_2S_2O_3$ sodium thiosulfate
$Cs_2CO_3$ cesium carbonate NaHCO₃ sodium bicarbonate
NaOH sodium hydroxide
Na₂SO₄ sodium sulfate
MgSO₄, magnesium sulfate
K₃PO₄ potassium phosphate
NH₄Cl ammonium chloride
LC/MS liquid chromatography/mass spectra
GCMS gas chromatography mass spectra
HPLC high performance liquid chromatography
GC gas chromatography
LC liquid chromatography
IC ion chromatography
IM intramuscular
CFU/cfu colony forming units
MIC minimum inhibitory concentration
Hr or h hours
atm atmospheres
rt or RT room temperature
TLC thin layer chromatography
HCl hydrochloric acid
H₂O water
EtNCO ethyl isocyanate
Pd/C palladium on carbon
NaOAc sodium acetate
H₂SO₄ sulfuric acid
N₂ nitrogen gas
H₂ hydrogen gas
n-BuLi n-butyl lithium
DI de-ionized
Pd(OAc)₂ palladium(II)acetate
PPh₃ triphenylphosphine
i-PrOH isopropyl alcohol
NBS N-bromosuccinimide
Pd[(Ph₃)P]₄ tetrakis(triphenylphosphine)palladium(0)
PTFE polytetrafluoroethylene
rpm revolutions per minute
SM starting material
Equiv. equivalents
¹H-NMR proton nuclear magnetic resonance
HPMCAS hydroxypropylmethylcellulose acetate
PVP polyvinylpyrrolidone
EDTA ethylenediaminetetraacetic acid
K2EDTA dibasic potassium ethylenediaminetetraacetate
mCPBA meta-chloroperoxybenzoic acid
aq aqueous
Boc₂O di-tert-butyl dicarbonate
DMAP N,N-dimethylaminopyridine
mL milliliters
L liters
mol moles
g grams
LCMS liquid chromatography-mass spectrometry
MHz megahertz
CDCl₃ deuterochloroform
NEt₃ triethylamine
mmol millimoles
psi pounds per square inch
iPrOH isopropylalcohol
ppm parts per million
NH₄NO₃ ammonium nitrate
Hz hertz
Pd(dppf)Cl₂ [1,1'-Bis(diphenylphosphino)ferrocene]dichloropalladium(II)
L liters
MeOD deutero-methanol
CD₃OD deutero-methanol
ee enantiomeric excess
min minutes
Bn benzyl
RBF round-bottom flask
MeCN acetonitrile
PES polyethersulfone
mm millimeters
μm micrometers
M molar
N normal
Boc tert-butoxycarbonyl
ESMS electrospray mass spectrometry
CV column volume
D₂O deuterium oxide
NH₃ ammonia
OBD optimum bed density
mg milligrams
CLSI Clinical and Laboratory Standards Institute
ATCC American Type Culture Collection
MHII Mueller Hinton II
μL microliters
WT wild type
CGSC Coli Genetic Stock Center
MS mass spectrometry
IS internal standard
APCI atmospheric pressure chemical ionization
MRM multiple reaction monitoring
m/z mass-to-charge ratio
LLOQ lower limit of quantitation
ng nanograms
UV ultraviolet
SD standard deviation
% CV coefficient of variation
PO perioral
MC microcrystalline cellulose
EDTA ethylenediaminetetraacetic acid or ethylenediaminetetraacetate
PK pharmacokinetic
IV intravenous
D5W 5% dextrose in water solution
HPMC-AS hydroxypropyl methylcellulose acetyl succinate
PVP polyvinylprrolidone
CAPT captisol
ATP adenosine triphosphate
ADP adenosine diphosphate
NADH nicotinamide adenine dinucleotide (reduced form)
NAD+ nicotinamide adenine dinucleotide (oxidized form)
TRIS tris(hydroxymethyl)aminomethane
mM millimolar
MgCl₂ magnesium chloride
KCl potassium chloride
μM micromolar
DTT dithiothreitol
nM nanomolar
$K_i$ dissociation constant
$IC_{50}$ half maximal inhibitory concentration
μg micrograms
BSA bovine serum albumin
LDH lactate dehydrogenase
PVDF polyvinylidene fluoride
AcN acetonitrile
$V_{MAX}$ the maximum initial velocity or rate of a reaction

Example 1

Preparation of 2-(2-nitrophenyl)-2,5-dihydrofuran and 2-(2-nitrophenyl)-2,3-dihydrofuran (3a&3b)

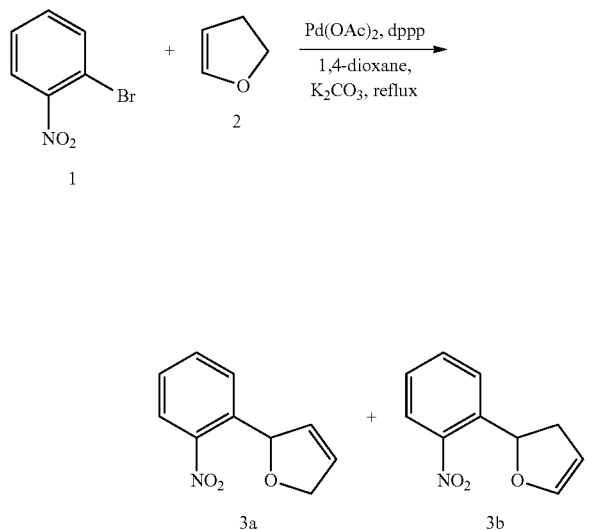

Mixed 1-bromo-2-nitro-benzene (1) (600 g, 99%, 2.941 mol, Alfa Aesar A11686), 1,3-bis(diphenylphosphino)propane (62.50 g, 97%, 147.0 mmol, Alfa Aesar A12931), 1,4-dioxane (2.970 L, Sigma-Aldrich 360481), potassium carbonate (812.9 g, 5.882 mol, JT-Baker 301201), and 2,3-dihydrofuran (2) (1.041 kg, 99%, 1.124 L, 14.70 mol, Aldrich 200018). A stream of nitrogen was bubbled through the stirring mixture for 4 hrs, followed by addition of palladium (II) acetate (16.51 g, 73.52 mmol, Strem 461780) and continuation of deoxygenation for another 10 minutes. The reaction mixture was stirred at reflux under nitrogen overnight (NMR of a worked-up aliquot showed complete consumption of arylbromide). It was allowed to cool, diluted with hexane (1 L), filtered through a short plug of Florisil® (500 g, –200 mesh), and eluted with EtOAc. The filtrate was concentrated under reduced pressure (2-(2-nitrophenyl)-2,3-dihydrofuran is volatile under high vacuum and may be somewhat unstable at room temperature) giving a mixture of (3a) and (3b) as a dark brown oil (654.0 g). The crude material was stored in the refrigerator and carried forward without further purification.

Example 2

Preparation of 2-tetrahydrofuran-2-yl-aniline (4)

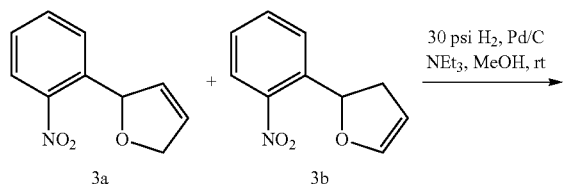

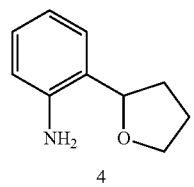

Placed 5% palladium on carbon (16.3 g, 50% wet, 3.83 mmol, Aldrich 330116) in a Parr bottle under nitrogen, followed by MeOH (100 mL, JT-Baker 909333). Added the crude mixture of 2-(2-nitrophenyl)-2,5-dihydrofuran and 2-(2-nitrophenyl)-2,3-dihydrofuran (3a&3b)) (163 g) dissolved in MeOH (389 mL), followed by $NEt_3$ (237.6 mL, 1.705 mol, Sigma-Aldrich 471283). Placed the vessel on a Parr shaker and saturated with $H_2$. Added 30 psi $H_2$ and shook until consumption complete (LCMS and NMR showed complete reaction). The reaction mixture was purged with nitrogen, filtered through Celite™ and rinsed with EtOAc. The filtrate was concentrated on a rotary evaporator giving a brown oil. Repeated the reaction three more times on the same scale and the batches were combined for purification. The crude product was vacuum distilled (ca. 15 ton) collecting the distillate at 108-129° C. to give (4) as a clear faint yellow oil (427.9 g, average yield was 84%; 98% GCMS purity). LCMS (C18 column eluting with 10-90% $CH_3CN$/water gradient over 5 minutes with formic acid modifier) M+1: 163.95 (1.46 min). $^1$H NMR (300 MHz, $CDCl_3$): δ 7.15-7.04 (m, 2H), 6.77-6.62 (m, 2H), 4.85-4.77 (m, 1H), 4.18 (s, 2H), 4.12-4.02 (m, 1H), 3.94-3.85 (m, 1H), 2.25-1.95 (m, 4H) ppm.

Example 2a

Preparation of (R)-2-(tetrahydrofuran-2-yl)aniline (4a)

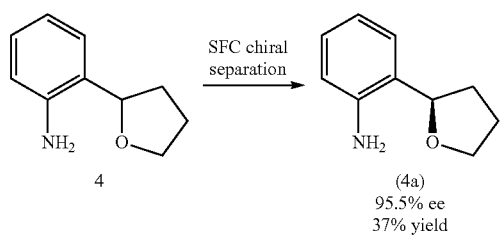 [SMILES: Nc1ccccc1C1CCCO1 ; Nc1ccccc1[C@H]1CCCO1]

Dissolved 33 g of compound (4) into MeOH (265 ml) which resulted in a concentration of approximately 125 mg/ml. The mixture was filtered through a 0.2 micron membrane filter then chromatographed on a ChiralPak® IC column (30 mm×150 mm, column temp 35° C., Chiral Technologies) at 100 bar using a Berger multigram supercritical fluid chromatographic system. Mobile phase was (90:10) $CO_2$:$CH_3OH$ eluting at 350 ml/min with UV monitoring at 220 nanometers. Obtained 15.64 g of desired product (4a) as a green oil. Analytical SFC ([90:10] $CO_2$:$CH_3OH$, at 5 ml/min on a ChiralPak IC column (4.6×100 mm) held at 35° C. and run at 100 bar pressure with UV monitoring at 220 nm) showed 95.5% ee with 95% overall purity.

Example 3

Preparation of 4-bromo-2-tetrahydrofuran-2-yl-aniline (5)

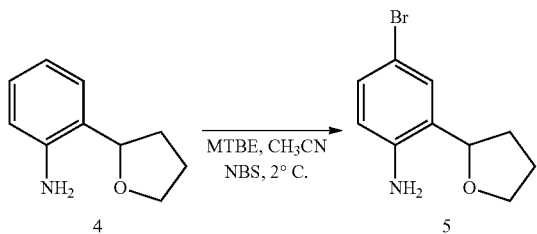 [SMILES: Nc1ccccc1C1CCCO1 ; Nc1ccc(Br)cc1C1CCCO1]

To a stirring solution of 2-tetrahydrofuran-2-yl-aniline (4) (53.45 g, 327.5 mmol) in methyl tert-butyl ether (MTBE, 641.4 mL) and acetonitrile (213.8 mL) cooled to 2° C. was added N-bromosuccinimide (58.88 g, 99%, 327.5 mmol, Aldrich B81255) in 4 portions maintaining internal temperature below about 8° C. The reaction mixture was stirred while cooling with an ice-water bath for 30 minutes (NMR of a worked-up aliquot showed complete consumption of starting material). Added aqueous 1 N Na₂S₂O₃ (330 mL), removed the cold bath and stirred for 20 minutes. The mixture was diluted with EtOAc and the layers were separated. The organic phase was washed with saturated aqueous NaHCO₃ (2×), water, brine, dried over MgSO₄, filtered through a short plug of silica, eluted with EtOAc, and concentrated under reduced pressure to give (5) as a very dark amber oil (82.25 g, 77-94% HPLC purity). Carried forward without further purification. LCMS (C18 column eluting with 10-90% CH₃CN/water gradient over 5 minutes with formic acid modifier) M+1: 242.10 (2.89 min). $^1$H NMR (300 MHz, CDCl₃) δ 7.22 (d, J=2.3 Hz, 1H), 7.16 (dd, J=8.4, 2.3 Hz, 1H), 6.54 (d, J=8.4 Hz, 1H), 4.79-4.73 (m, 1H), 4.15 (s, 2H), 4.10-4.01 (m, 1H), 3.93-3.85 (m, 1H), 2.26-2.13 (m, 1H), 2.12-1.97 (m, 3H) ppm.

Example 4

Preparation of N-(4-bromo-2-nitro-6-tetrahydrofuran-2-yl-phenyl)-2,2,2-trifluoro-acetamide (6)

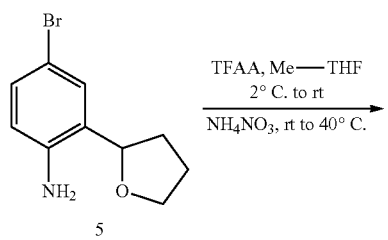

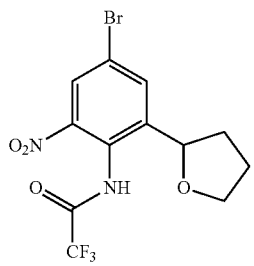

To trifluoroacetic anhydride (455.3 mL, 3.275 mol, Sigma-Aldrich 106232) stirring at 2° C. was slowly added 4-bromo-2-tetrahydrofuran-2-yl-aniline (5) (79.29 g, 327.5 mmol) as a thick oil via addition funnel over 15 minutes (reaction temperature rose to 14° C.). The remaining oil was rinsed into the reaction mixture with anhydrous 2-methyltetrahydrofuran (39.6 mL, Sigma-Aldrich 414247). The cold bath was removed and ammonium nitrate (34.08 g, 425.8 mmol, Aldrich 467758) was added. The reaction temperature rose to 40° C. over about 30 minutes at which time a cold water bath was used to control the exotherm and bring the reaction to room temperature. The cold bath was then removed and stirring continued for another 40 minutes (HPLC showed very little remaining un-nitrated material). The reaction mixture was slowly poured into a stirring mixture of crushed ice (800 g). The solid precipitate was collected by filtration, washed with water, saturated aqueous NaHCO₃ (to pH 8), water again, and hexane. The wet solid was dried first in a convection oven at 50° C. for several hours and then under reduced pressure in an oven at 40° C. overnight giving (6) as a light brown solid (77.86 g, 62% yield; 98% HPLC purity). LCMS (C18 column eluting with 10-90% CH₃CN/water gradient over 5 minutes with formic acid modifier) M+1: 383.19 (3.27 min). $^1$H NMR (300 MHz, CDCl₃) δ 9.81 (s, 1H), 8.08 (d, J=2.2 Hz, 1H), 7.73 (d, J=2.2 Hz, 1H), 4.88 (dd, J=9.0, 6.5 Hz, 1H), 4.17-4.08 (m, 1H), 4.03-3.95 (m, 1H), 2.45-2.34 (m, 1H), 2.17-2.06 (m, 2H), 1.96-1.83 (m, 1H) ppm.

Example 5

Preparation of 4-bromo-2-nitro-6-tetrahydrofuran-2-yl-aniline (6a)

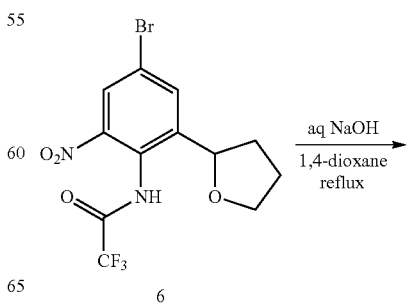

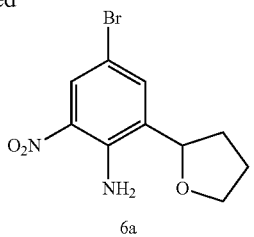

6a

Dissolved N-(4-bromo-2-nitro-6-tetrahydrofuran-2-yl-phenyl)-2,2,2-trifluoro-acetamide (6) (54.00 g, 140.9 mmol) in 1,4-dioxane (162 mL) and added aqueous 6 M NaOH (70.45 mL, 422.7 mmol, JT-Baker 567202). The reaction mixture was stirred at reflux for 2 days (HPLC showed complete conversion), allowed to cool, diluted with MTBE (800 mL), washed with water (2×200 mL), saturated aqueous NH$_4$Cl, water and brine. The mixture was dried over MgSO$_4$, filtered, and concentrated under reduced pressure to give (6a) as a dark amber oil (40.96 g, 93% yield; overall 92% HPLC plus NMR purity). LCMS (C18 column eluting with 10-90% MeOH/water gradient from 3-5 minutes with formic acid modifier) M+1: 287.28 (3.44 min). $^1$H NMR (300 MHz, CDCl$_3$) δ 8.24 (d, J=2.4 Hz, 1H), 7.41 (d, J=2.3 Hz, 1H), 6.91 (s, 2H), 4.80 (t, J=7.2 Hz, 1H), 4.14-4.05 (m, 1H), 3.98-3.90 (m, 1H), 2.36-2.19 (m, 1H), 2.15-2.01 (m, 3H) ppm.

Example 6

Preparation of 2-[5-(4-amino-3-nitro-5-tetrahydrofuran-2-yl-phenyl)pyrimidin-2-yl]propan-2-ol (8)

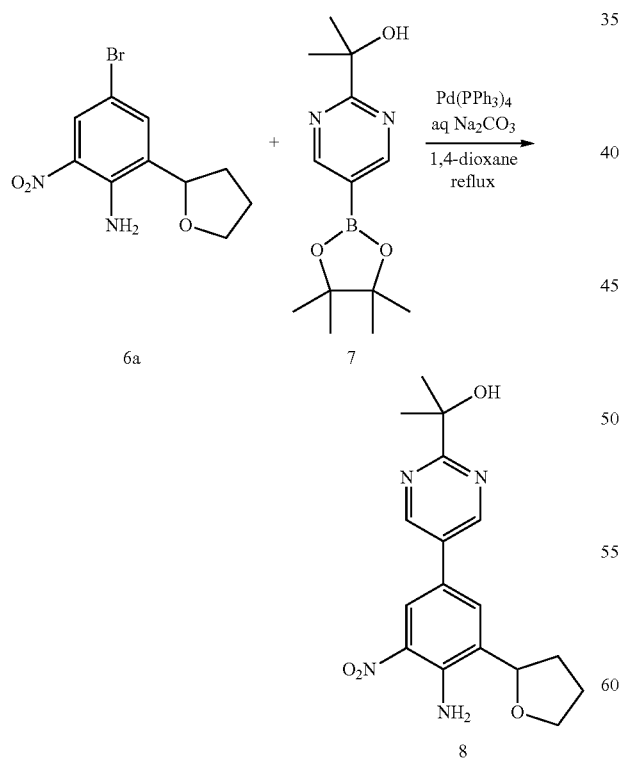

Mixed 4-bromo-2-nitro-6-tetrahydrofuran-2-yl-aniline (6a) (40.40 g, 92%, 129.5 mmol), 1,4-dioxane (260 mL, Sigma-Aldrich 360481), 2-[5-(4,4,5,5-tetramethyl-1,3,2-di-oxaborolan-2-yl)pyrimidin-2-yl]propan-2-ol (7) (41.05 g, 155.4 mmol), and aqueous 2.7 M Na$_2$CO$_3$ (143.9 mL, 388.5 mmol). A stream of nitrogen was bubbled through the stirring mixture for 1 hr, followed by addition of tetrakis(triphenylphosphine)palladium (0) (7.48 g, 6.47 mmol, Strem 462150). The reaction mixture was stirred at reflux for 2 hrs (HPLC showed complete reaction), allowed to cool, diluted with EtOAc, washed with water, saturated aqueous NH$_4$Cl, brine, dried over MgSO$_4$, and filtered through a short plug of Florisil® eluting with EtOAc. The filtrate was concentrated under reduced pressure giving a dark brown oil. Dissolved in CH$_2$Cl$_2$ and eluted through a short plug of silica gel with CH$_2$Cl$_2$ and then EtOAc. The desired fraction was concentrated on a rotary evaporator until a precipitate formed giving a thick brown slurry, which was triturated with MTBE. The solid was collected by filtration, washed with MTBE, and dried under high vacuum giving (8) as a yellow solid (35.14 g, 99+% HPLC purity,). LCMS (C18 column eluting with 10-90% CH$_3$CN/water gradient over 5 minutes with formic acid modifier) M+1: 345.00 (2.69 min). $^1$H NMR (300 MHz, CDCl$_3$) δ 8.88 (s, 2H), 8.36 (d, J=2.2 Hz, 1H), 7.56 (d, J=2.1 Hz, 1H), 7.09 (s, 2H), 4.92 (t, J=7.2 Hz, 1H), 4.62 (s, 1H), 4.20-4.11 (m, 1H), 4.03-3.94 (m, 1H), 2.39-2.26 (m, 1H), 2.23-2.08 (m, 3H), 1.64 (s, 6H) ppm. The filtrate was further concentrated and purified by ISCO silica gel chromatography eluting with 0 to 80% EtOAc/hexane giving a second crop of product (8) as an amber solid (4.46 g, 88% overall yield; 88% HPLC purity.

Example 7

Alternate preparation of 2-[5-(4-amino-3-nitro-5-tetrahydrofuran-2-yl-phenyl)pyrimidin-2-yl]propan-2-ol (8)

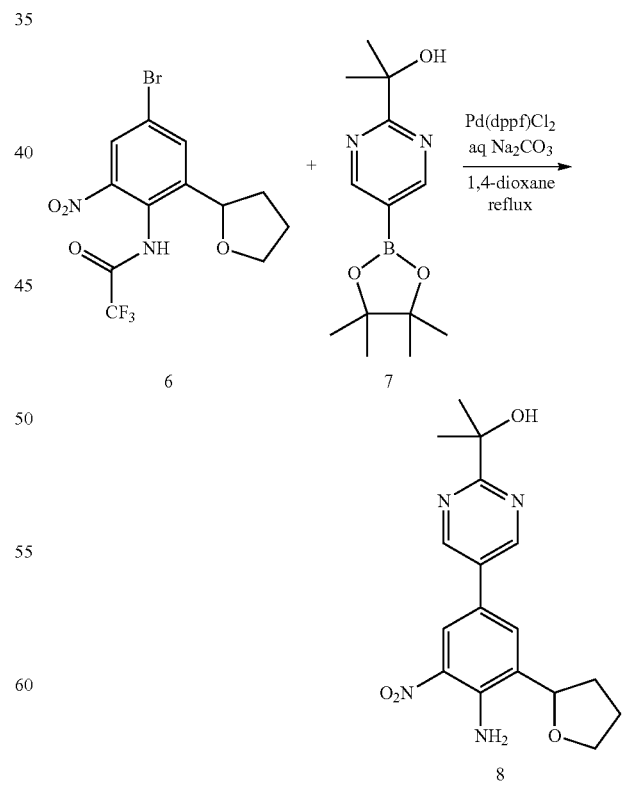

Mixed N-(4-bromo-2-nitro-6-tetrahydrofuran-2-yl-phenyl)-2,2,2-trifluoro-acetamide (6) (19.00 g, 49.59 mmol), 2-[5-(4,4,5,5-tetramethyl-1,3,2-dioxaborolan-2-yl)pyrimidin-2-yl]propan-2-ol (7) (14.41 g, 54.55 mmol), aqueous 2.7 M sodium carbonate (73.48 mL, 198.4 mmol), and 1,4-dioxane (190 mL, Sigma-Aldrich 360481). A stream of nitrogen was bubbled through the stirring mixture for 40 minutes, followed by addition of 1,1'-bis(diphenylphosphino)ferrocene dichloropalladium dichloromethane adduct (2.025 g, 2.480 mmol, Strem 460450). The reaction mixture was stirred at reflux under $N_2$ for 7 hrs, added another 50 mL of saturated aqueous sodium carbonate, and refluxed for another 16 hrs. The mixture was allowed to cool, then diluted with EtOAc (500 mL) and water (200 mL). The layers were separated and the aqueous phase extracted with EtOAc (200 mL). The combined organic phase was washed with water (500 mL), brine (500 mL), dried over $Na_2SO_4$, filtered through a Florisil® plug, and concentrated on a rotary evaporator to give crude (8) as an orange oil. Crude product was purified by ISCO silica gel chromatography eluting with 20-90% EtOAc/hexane to give (8) as an orange solid (15.00 g, 87% yield; 81-88% purity). LCMS (C18 column eluting with 10-90% $CH_3CN$/water gradient over 5 minutes with formic acid modifier) M+1: 345.35 (2.68 min). $^1$H NMR (300 MHz, $CDCl_3$) δ 8.88 (s, 2H), 8.36 (d, J=2.2 Hz, 1H), 7.56 (d, J=2.1 Hz, 1H), 7.09 (s, 2H), 4.92 (t, J=7.2 Hz, 1H), 4.62 (s, 1H), 4.20-4.11 (m, 1H), 4.03-3.94 (m, 1H), 2.39-2.26 (m, 1H), 2.23-2.08 (m, 3H), 1.64 (s, 6H) ppm.

Example 8

Preparation of 2-[5-(3,4-diamino-5-tetrahydrofuran-2-yl-phenyl)pyrimidin-2-yl]propan-2-ol (9)

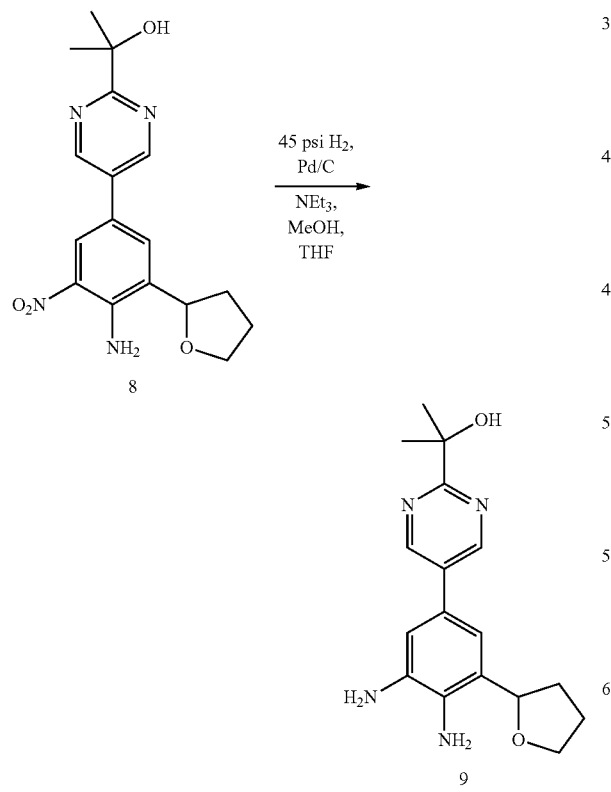

To a suspension of 2-[5-(4-amino-3-nitro-5-tetrahydrofuran-2-yl-phenyl)pyrimidin-2-yl]propan-2-ol (8) (30.10 g, 87.41 mmol) and THF (90 mL) in a Parr bottle under nitrogen was added a slurry of 5% palladium on carbon (3.01 g, 50% wet, 0.707 mmol, Aldrich 330116) in MeOH (90 mL, JT-Baker 909333), followed by $NEt_3$ (24.37 mL, 174.8 mmol, Sigma-Aldrich 471283). Placed the vessel on a Parr shaker and saturated with $H_2$. Added 45 psi $H_2$ and shook until consumption was complete (HPLC showed complete conversion). The reaction mixture was purged with nitrogen, filtered through Celite™ and rinsed with EtOAc. The filtrate was re-filtered through a 0.5 micron glass fiber filter paper sandwiched between two P5 papers, and concentrated under reduced pressure giving (9) as a light brown foam (28.96 g, 98% yield; 93% NMR purity). LCMS (C18 column eluting with 10-90% $CH_3CN$/water gradient over 5 minutes with formic acid modifier) M+1: 315.32 (1.54 min). $^1$H NMR (300 MHz, $CDCl_3$) δ 8.83 (s, 2H), 6.92 (d, J=1.8 Hz, 1H), 6.88 (d, J=1.8 Hz, 1H), 4.90 (dd, J=7.9, 6.2 Hz, 1H), 4.72 (s, 1H), 4.18 (s, 2H), 4.17-4.08 (m, 1H), 3.99-3.89 (m, 1H), 3.46 (s, 2H), 2.34-2.19 (m, 1H), 2.17-2.05 (m, 3H), 1.63 (s, 6H) ppm.

Example 9

Preparation of 1-ethyl-3-[5-[2-(1-hydroxy-1-methylethyl)pyrimidin-5-yl]-7-tetrahydrofuran-2-yl-1H-benzimidazol-2-yl]urea (11)

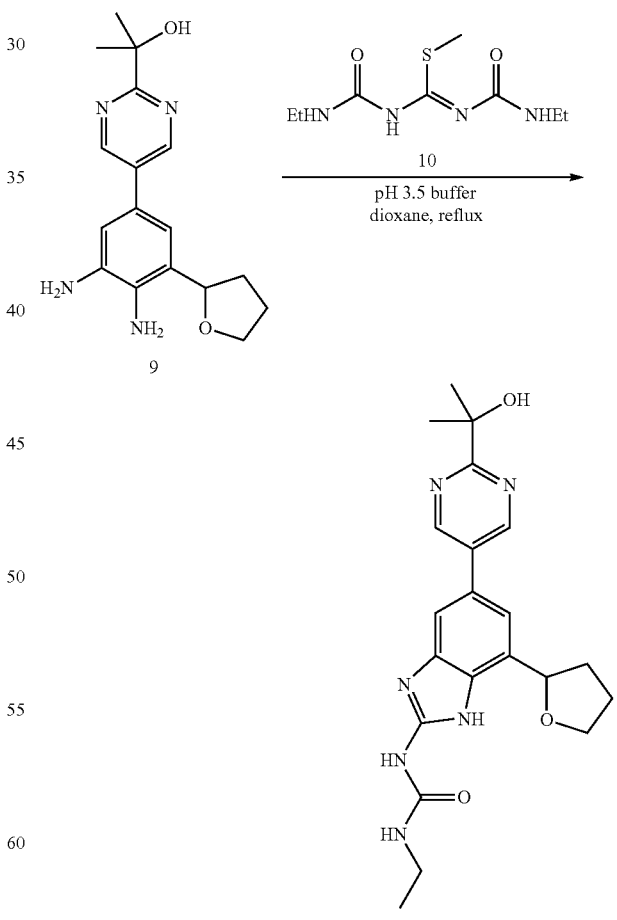

To a stirring solution of 2-[5-(3,4-diamino-5-tetrahydrofuran-2-yl-phenyl)pyrimidin-2-yl]propan-2-ol (9) (32.10 g, 102.1 mmol) in 1,4-dioxane (160.5 mL, Sigma-Aldrich 360481) was added pH 3.5 buffer (240.8 mL), prepared by dissolving NaOAc trihydrate (34.5 g) in 1N aqueous $H_2SO_4$ (240 mL). Added 1-ethyl-3-(N-(ethylcarbamoyl)-C-methyl-sulfanyl-carbonimidoyl)urea (10) (28.46 g, 122.5 mmol, CB Research and Development) and stirred at reflux overnight (HPLC showed 99% consumption of starting diamine). The reaction mixture was cooled to room temperature and poured portion-wise (frothing) into a stirring solution of aqueous saturated $NaHCO_3$ (480 mL) and water (120 mL) giving pH 8-9. This was stirred for 30 minutes, the solid was collected by filtration, washed copiously with water to neutral pH, and then more sparingly with EtOH. The solid was dried under reduced pressure giving (11) as an off-white solid (34.48 g, 82% yield; 99.4% HPLC purity). LCMS (C18 column eluting with 10-90% $CH_3CN$/water gradient over 5 minutes with formic acid modifier) M+1: 411.41 (1.73 min). $^1$H NMR (300 MHz, MeOD) δ 9.02 (s, 2H), 7.62 (s, 1H), 7.37 (s, 1H), 5.31 (s, 1H), 4.23 (dd, J=14.5, 7.3 Hz, 1H), 4.01 (dd, J=15.0, 7.1 Hz, 1H), 3.38-3.28 (m, 2H), 2.58-2.46 (m, 1H), 2.16-2.05 (m, 2H), 2.02-1.88 (m, 1H), 1.63 (s, 6H), 1.22 (t, J=7.2 Hz, 3H) ppm.

Example 10

Chiral chromatographic isolation of 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea (12)

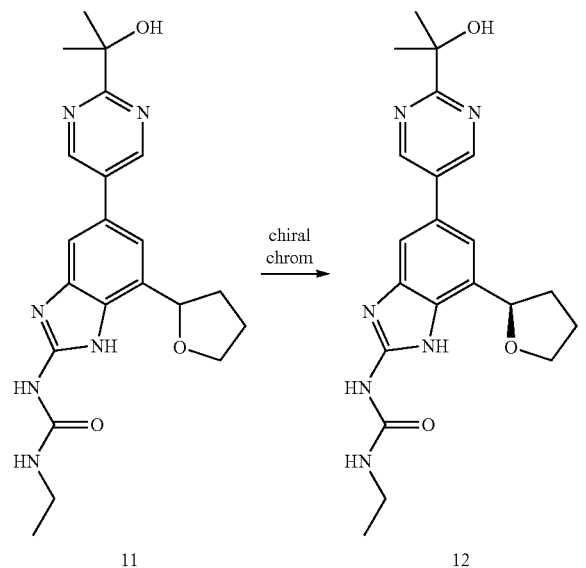 [SMILES: CCNC(=O)Nc1nc2cc(-c3cnc(C(C)(C)O)nc3)cc(C3CCCO3)c2[nH]1 ; CCNC(=O)Nc1nc2cc(-c3cnc(C(C)(C)O)nc3)cc([C@H]3CCCO3)c2[nH]1]

A racemic sample of 1-ethyl-3-[5-[2-(1-hydroxy-1-methyl-ethyl)pyrimidin-5-yl]-7-tetrahydrofuran-2-yl-1H-benzimidazol-2-yl]urea (11) (24.60 g) was resolved on a CHIRALPAK® IC® column (by Chiral Technologies) eluting with DCM/MeOH/TEA (60/40/0.1) at 35° C. giving the desired enantiomer (12) as a white solid (11.35 g, 45% yield; 99+% HPLC purity, 99+% ee). Analytical chiral HPLC retention time was 6.2 min (CHIRALPAK® IC® 4.6×250 mm column, 1 mL/min flow rate, 30° C.).

The structure and absolute stereochemistry of 12 were confirmed by single-crystal x-ray diffraction analysis. Single crystal diffraction data were acquired on a Bruker Apex II diffractometer equipped with sealed tube Cu K-alpha source (Cu Kα radiation, γ=1.54178 Å) and an Apex II CCD detector. A crystal with dimensions of ½×0.05×0.05 mm was selected, cleaned using mineral oil, mounted on a MicroMount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric $P2_1$ space group.

A diffraction data set of reciprocal space was obtained to a resolution of 0.9 Å using 0.5° steps using 60 s exposure for each frame. Data were collected at 100 (2) K. Integration of intensities and refinement of cell parameters were accomplished using APEXII software. Observation of the crystal after data collection showed no signs of decomposition. As shown in FIG. 1, there are two symmetry independent molecules in the structure and both symmetry independent molecules are R isomers.

The data were collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with $P2_1$ space group. The lattice parameters are a=9.8423(4) Å, b=10.8426(3) Å, c=19.4441 (7) Å, β=102.966(3)°. Volume=2022.09(12) Å$^3$.

Example 11

Preparation of the methanesulfonic acid salt of 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea (13)

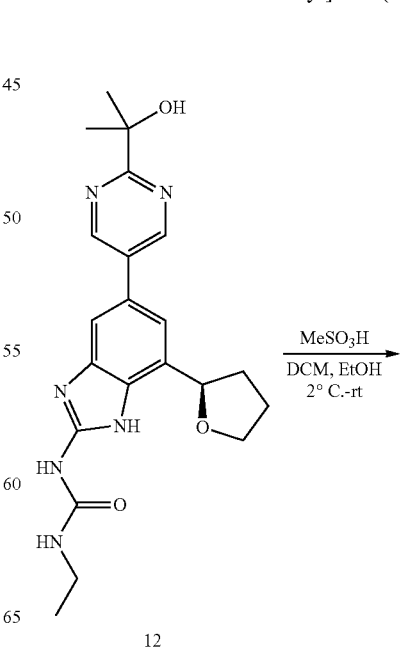

Example 12

Preparation of 2-(2-fluoro-6-nitro-phenyl)-2,3-dihydrofuran (15A) and 2-(2-fluoro-6-nitro-phenyl)-2,5-dihydrofuran (15B)

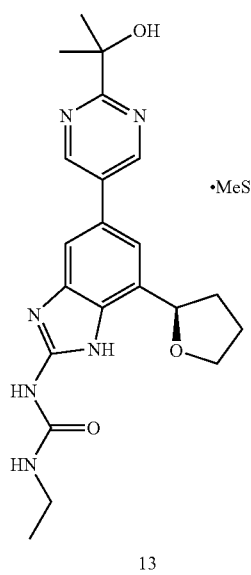

13

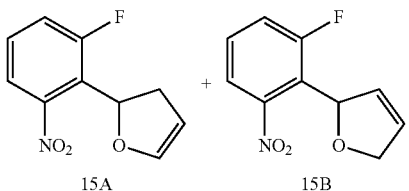

A stirring suspension of 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea (12) (9.32 g, 22.71 mmol) in absolute ethanol (93.2 mL) was cooled with an ice-water bath. Added methanesulfonic acid (1.548 mL, 23.85 mmol, Sigma-Aldrich 471356), removed cold bath and stirred at room temperature for 20 minutes. It was concentrated on a rotary evaporator at 35° C. to a thick slurry, diluted with EtOAc, collected the solid by filtration, washed with EtOAc, and dried under reduced pressure giving an initial crop of (13) as a white solid (8.10 g). The filtrate was concentrated on a rotavap giving a yellowish glassy foam, which was dissolved in EtOH, concentrated to a solid slurry, triturated with EtOAc/Et$_2$O, and collected by filtration. The solid was washed with EtOAc/Et$_2$O, combined with the first crop, and dried under reduced pressure giving (13) as a white solid (9.89 g, 86% yield; 99+% HPLC purity, 99+% ee). Analytical chiral HPLC shows one enantiomer with retention time of 6.3 min eluting with DCM/MeOH/TEA (60/40/0.1) on a CHIRALPAK® IC® 4.6×250 mm column with 1 mL/min flow rate at 30° C. LCMS (C18 column eluting with 10-90% CH$_3$CN/water gradient over 5 minutes with formic acid modifier) M+1: 411.53 (1.74 min). $^1$H NMR (300 MHz, MeOD) δ 9.07 (s, 2H), 7.79 (s, 1H), 7.62 (s, 1H), 5.30 (t, J=7.3 Hz, 1H), 4.24 (dd, J=14.6, 7.3 Hz, 1H), 4.04 (dd, J=15.0, 7.6 Hz, 1H), 3.40-3.30 (m, 2H), 2.72 (s, 3H), 2.65-2.54 (m, 1H), 2.20-2.07 (m, 2H), 2.04-1.90 (m, 1H), 1.64 (s, 6H), 1.23 (t, J=7.2 Hz, 3H) ppm.

2-Bromo-1-fluoro-3-nitro-benzene (14) (200.3 g, 98%, 892.3 mmol, Bosche F6657), 1,4-dioxane (981.5 mL, Sigma-Aldrich 360481), and 2,3-dihydrofuran (2) (341.1 mL, 99%, 4.462 mol, Aldrich 200018) were charged in a reaction flask, followed by N,N-diisopropylethylamine (155.4 mL, 892.3 mmol, Sigma-Aldrich 550043) and bromo(tri-tert-butylphosphine)palladium(I) dimer (6.936 g, 8.923 mmol, Johnson Matthey C4099). The mixture was stirred at reflux for 2 hrs (HPLC showed 98% consumption of starting arylbromide). It was allowed to cool, the precipitate was removed by filtration, rinsed with EtOAc, and the filtrate concentrated in vacuo to a dark reddish brown semi-solid oil. This was dissolved in CH$_2$Cl$_2$, eluted through a plug of silica with CH$_2$Cl$_2$, and concentrated in vacuo giving a mixture of 15A and 15B as a dark amber oil (291.3 g). The crude product was carried forward without further purification. The major product was 2-(2-fluoro-6-nitro-phenyl)-2,3-dihydrofuran (15A) (96%): LCMS (C18 column eluting with 10-90% CH$_3$CN/water gradient over 5 minutes with formic acid modifier) M+1: 210.23 (3.13 min); $^1$H NMR (300 MHz, CDCl$_3$) δ 7.54 (dt, J=8.0, 1.2 Hz, 1H), 7.43 (td, J=8.2, 5.2 Hz, 1H), 7.32 (ddd, J=9.7, 8.3, 1.3 Hz, 1H), 6.33 (dd, J=4.9, 2.4 Hz, 1H), 5.80 (t, J=10.9 Hz, 1H), 5.06 (q, J=2.4 Hz, 1H), 3.18-3.07 (m, 1H), 2.94-2.82 (m, 1H) ppm. The minor product was 2-(2-fluoro-6-nitro-phenyl)-2,5-dihydrofuran (15B) (4%): GCMS (Agilent HP-5MS 30 m×250 μm×0.25 μm column heating at 60° C. for 2 min to 300° C. over 15 min with a 1 mL/min flow rate) M+1: 210 (11.95 min). $^1$H NMR (300 MHz, CDCl$_3$) δ 7.47 (d, J=8.0 Hz, 1H), 7.43-7.34 (m, 1H), 7.30-7.23 (m, 1H), 6.21-6.15 (m, 1H), 6.11-6.06 (m, 1H), 5.97-5.91 (m, 1H), 4.89-4.73 (m, 2H) ppm.

Example 13

Preparation of
3-fluoro-2-tetrahydrofuran-2-yl-aniline (16)

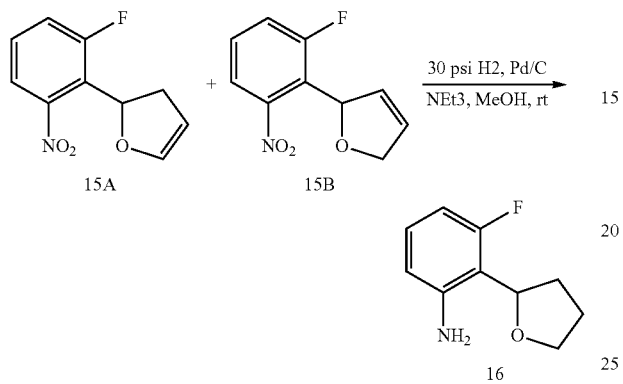

Placed 5% palladium on carbon (37.3 g, 50% wet, 8.76 mmol, Aldrich 330116) in a Parr bottle under nitrogen, followed by MeOH (70 mL, JT-Baker 909333). Added the crude mixture of 2-(2-fluoro-6-nitro-phenyl)-2,3-dihydrofuran and 2-(2-fluoro-6-nitro-phenyl)-2,5-dihydrofuran (15A&15B) (186.6 g, 892.1 mmol) dissolved in MeOH (117 mL), followed by NEt₃ (124.3 mL, 892.1 mmol, Sigma-Aldrich 471283). Placed the vessel on a Parr shaker and saturated with H₂. After adding 45 psi H₂, the reaction mixture was shaken until consumption of the starting material was complete (HPLC and LCMS showed complete reaction). The reaction mixture was purged with nitrogen, filtered through Celite™ and rinsed with EtOAc. The filtrate was concentrated on a rotary evaporator giving a brown oil, which was dissolved in Et₂O and washed with water (2×). The ether phase was extracted with aqueous 1 N HCl (5×250 mL), which was washed with Et₂O (3×) and then basified with aqueous 6 N NaOH to pH 12-14. The basic aqueous phase was extracted with CH₂Cl₂(4×), and the combined organic extract washed with saturated aqueous NH₄Cl, dried over MgSO₄, and filtered through a pad of silica eluting with CH₂Cl₂ to 25% EtOAc/hexane. The desired filtrate was concentrated under reduced pressure giving 16 as a light brown oil (121.8 g, 84% GCMS plus NMR purity). GCMS (Agilent HP-5MS 30 m×250 μm×0.25 μm column heating at 60° C. for 2 min to 300° C. over 15 min with a 1 mL/min flow rate) M+1: 182.0 (11.44 min). LCMS (C18 column eluting with 10-90% CH₃CN/water gradient over 5 minutes with formic acid modifier) M+1: 182.10 (2.61 min). ¹H NMR (300 MHz, CDCl₃) δ 6.97 (td, J=8.1, 6.3 Hz, 1H), 6.43-6.35 (m, 2H), 5.21-5.13 (m, 1H), 4.54 (s, 2H), 4.16-4.07 (m, 1H), 3.90-3.81 (m, 1H), 2.23-2.00 (m, 4H) ppm. Additional crops were obtained as follows: the combined ether phase was washed with saturated aqueous NaHCO₃, brine, dried over Na₂SO₄, decanted, and concentrated under reduced pressure. The oil was vacuum distilled (ca. 15 torr) collecting the distillate at 101-108° C. To a stirring solution of the distilled oil in EtOH (1 volume) at 2° C. was slowly added 5 M HCl (1 eq) in iPrOH. The resulting suspension was brought to room temperature, diluted with EtOAc (3 volumes, vol/vol), and stirred for 2 hrs. The white solid was collected by filtration, washed with EtOAc, and dried under reduced pressure giving a second crop of product as the HCl salt. The mother liquor was concentrated to a slurry, diluted with EtOAc and the solid collected by filtration, washed with EtOAc, and dried in vacuo giving the HCl salt as a third crop of the product. LCMS (C18 column eluting with 10-90% CH₃CN/water gradient over 5 minutes with formic acid modifier) M+1: 182.10 (2.58 min). ¹H NMR (300 MHz, CDCl₃) δ 10.73 (br.s, 3H), 7.66 (d, J=8.1 Hz, 1H), 7.33 (td, J=8.2, 5.9 Hz, 1H), 7.13-7.05 (m, 1H), 5.26 (dd, J=9.0, 6.5 Hz, 1H), 4.38-4.28 (m, 1H), 4.00-3.91 (m, 1H), 2.59-2.46 (m, 1H), 2.30-1.95 (m, 3H) ppm. The overall yield from the three crops was 76%.

Example 14

Preparation of
4-bromo-3-fluoro-2-tetrahydrofuran-2-yl-aniline (17)

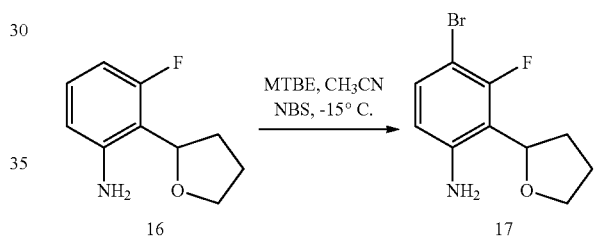

To a stirring solution of 3-fluoro-2-tetrahydrofuran-2-yl-aniline (16) (131.9 g, 92%, 669.7 mmol) in methyl tert-butyl ether (1.456 L) and acetonitrile (485 mL) cooled to −20° C. was added N-bromosuccinimide (120.4 g, 99%, 669.7 mmol, Aldrich B81255) in 3 portions maintaining a reaction temperature below about −15° C. After complete addition stirring was continued at −15 to −10° C. for 30 minutes. ¹H NMR of a worked-up aliquot showed 96% consumption of starting aniline so added another 4.82 g NBS and stirred at −10° C. for another 30 minutes. Aqueous 1 N Na₂S₂O₃ (670 mL) was added to the reaction mixture. The cold bath was removed, the mixture stirred for 20 minutes, then diluted with EtOAc. The layers were separated and the organic phase was washed with saturated aqueous NaHCO₃ (2×), water, brine, dried over Na₂SO₄, decanted, and concentrated under reduced pressure giving a dark amber oil. The residue was diluted with hexane and eluted through a short plug of silica eluting with 25% EtOAc/hexane to 50% EtOAc/hexane. The desired filtrate was concentrated in vacuo giving 17 as a dark amber oil (182.9 g, 90% yield; 86% NMR purity). LCMS (C18 column eluting with 10-90% CH₃CN/water gradient over 5 minutes with formic acid modifier) M+1: 260.12 (3.20 min). ¹H NMR (300 MHz, CDCl₃) δ 7.15 (dd, J=8.6, 7.6 Hz, 1H), 6.30 (dd, J=8.7, 1.3 Hz, 1H), 5.19-5.12 (m, 1H), 4.58 (s, 2H), 4.16-4.07 (m, 1H), 3.90-3.81 (m, 1H), 2.23-1.99 (m, 4H) ppm.

Example 15

Preparation of N-(4-bromo-3-fluoro-6-nitro-2-tetrahydrofuran-2-yl-phenyl)-2,2,2-trifluoro-acetamide (18)

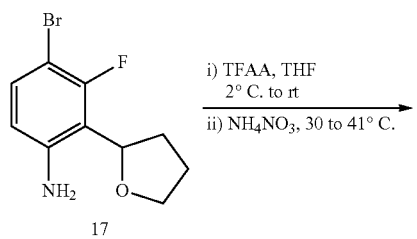

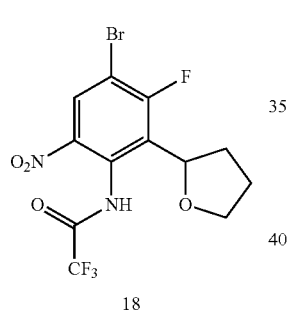

To trifluoroacetic anhydride (565.3 mL, 4.067 mol, Sigma-Aldrich 106232) stirring at 2° C. was slowly added neat 4-bromo-3-fluoro-2-tetrahydrofuran-2-yl-aniline (17) (123.0 g, 86%, 406.7 mmol) as a thick oil via addition funnel over about 20 minutes (reaction temperature rose to 13° C.). The remaining oil was rinsed into the reaction mixture with anhydrous THF (35 mL). The cold bath was removed and the reaction was heated to 35° C., followed by portion-wise addition of NH$_4$NO$_3$ (4.88 g×20 portions, 1.22 mol, Sigma-Aldrich A7455) over 2.5 hrs maintaining the reaction temperature between 30 and 41° C. using an ice-water bath only as needed to control the exotherm. After complete addition the reaction mixture was stirred for another 10 minutes (HPLC showed reaction 99% complete). It was slowly poured into crushed ice (1.23 kg) and stirred for 1 hr to allow formation of a filterable solid precipitate, which was collected and washed with water, sparingly with saturated aqueous NaHCO$_3$, and water again (to pH 7). The product was dried in a convection oven overnight at 40° C. and then under reduced pressure in an oven at 50° C. overnight giving 18 as a beige solid (152.5 g, 90% yield; 96% HPLC purity). LCMS (C18 column eluting with 10-90% CH$_3$CN/water gradient over 5 minutes with formic acid modifier) M+1: 401.30 (3.41 min). $^1$H NMR (300 MHz, CDCl$_3$) δ 10.56 (s, 1H), 8.19 (d, J=6.6 Hz, 1H), 5.22 (dd, J=10.3, 6.4 Hz, 1H), 4.22 (dd, J=15.8, 7.2 Hz, 1H), 3.99 (dd, J=16.1, 7.5 Hz, 1H), 2.50-2.38 (m, 1H), 2.22-2.11 (m, 2H), 1.86-1.71 (m, 1H) ppm.

Example 16

Preparation of 4-bromo-3-fluoro-6-nitro-2-tetrahydrofuran-2-yl-aniline (19)

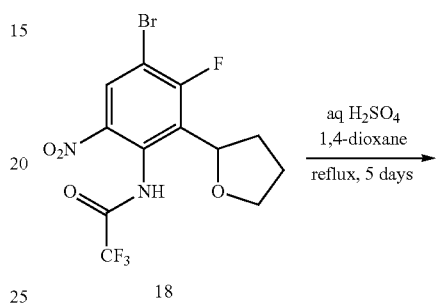

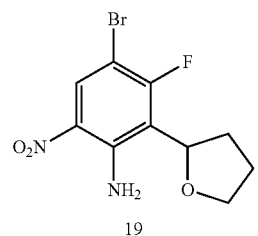

A reaction flask was charged with N-(4-bromo-3-fluoro-6-nitro-2-tetrahydrofuran-2-yl-phenyl)-2,2,2-trifluoro-acetamide (18) (242.3 g, 604.1 mmol), 1,4-dioxane (1.212 L), aqueous 2 M sulfuric acid (362.4 mL, 724.9 mmol), and stirred at reflux for 5 days (HPLC showed 98% conversion). Allowed to cool, diluted with EtOAc, neutralized with saturated aqueous NaHCO$_3$, separated the layers, and re-extracted the aqueous phase with EtOAc (2×). The combined organic phase was washed with brine (2×), dried over MgSO$_4$, filtered and concentrated in vacuo giving 19 as a greenish brown solid (181.7 g, 94% yield; 95% HPLC purity). The product was carried to the next step without further purification. LCMS (C18 column eluting with 10-90% CH$_3$CN/water gradient over 5 minutes with formic acid modifier) M+1: 305.20 (3.63 min). $^1$H NMR (300 MHz, CDCl$_3$) δ 8.35 (d, J=7.3 Hz, 1H), 7.45 (s, 2H), 5.23-5.16 (m, 1H), 4.23-4.14 (m, 1H), 3.93-3.84 (m, 1H), 2.31-1.96 (m, 4H) ppm.

Example 17

Preparation of 2-[5-(4-amino-2-fluoro-5-nitro-3-tetrahydrofuran-2-yl-phenyl)pyrimidin-2-yl]propan-2-ol (20)

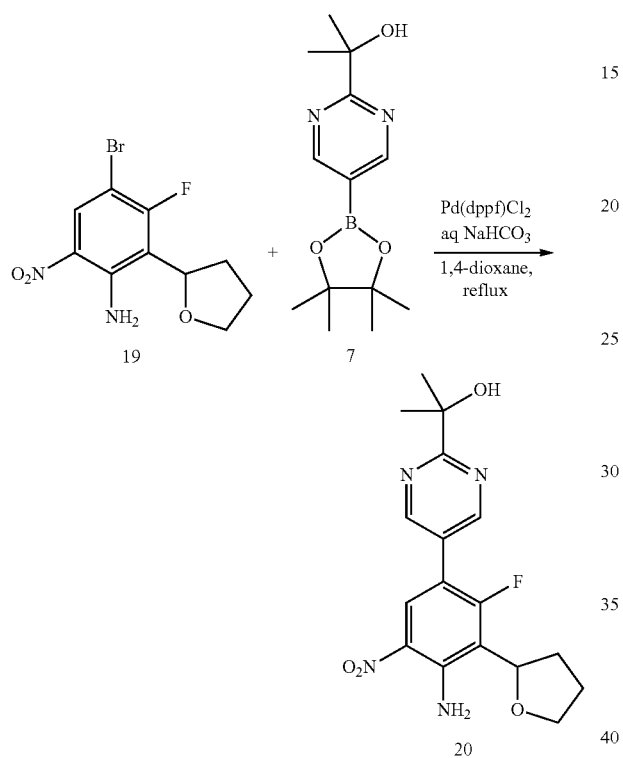

To a stirring solution of 4-bromo-3-fluoro-6-nitro-2-tetrahydrofuran-2-yl-aniline (19) (525.0 g, 1.721 mol, Bridge Organics Co.) in 1,4-dioxane (4.20 L, Sigma-Aldrich 360481) was added a 1.2 M aqueous solution of NaHCO$_3$ (4.302 L, 5.163 mol). A stream of nitrogen was bubbled through the stirring mixture for 2 hrs, followed by addition of 2-[5-(4,4,5,5-tetramethyl-1,3,2-dioxaborolan-2-yl)pyrimidin-2-yl]propan-2-ol (7) (545.4 g, 2.065 mol, Bridge Organics Co.) and 1,1'-bis(diphenylphosphino)ferrocene dichloropalladium dichloromethane adduct (42.16 g, 51.63 mmol, Strem 460450). The reaction mixture was stirred at reflux overnight, allowed to cool, diluted with EtOAc (8.4 L), and the layers were separated. The organic phase was washed with saturated aqueous NH$_4$Cl and then brine. The aqueous phase was re-extracted with EtOAc (4 L) and washed this organic extract with brine. The combined organic phase was dried over MgSO$_4$, filtered through a short plug of Florisil®, eluted with EtOAc, and the filtrate concentrated on a rotary evaporator giving a dark brown wet solid. This was dissolved in CH$_2$Cl$_2$, loaded on a pad of silica gel, eluted with hexane, then 25% EtOAc/hexane, and then 50% EtOAc/hexane. The desired filtrate was concentrated on a rotary evaporator to a thick suspension, and the solid was collected by filtration, triturated with MTBE, and dried in vacuo giving 20 as a bright yellow solid (55.8% yield, 90-97% HPLC purity). The filtrate was concentrated and the above purification was repeated giving a second crop of 20 as a bright yellow solid (19.7% yield). The filtrate was again concentrated giving a dark brown oil and this was loaded on a silica column with toluene and minimal CH$_2$Cl$_2$. It was eluted with EtOAc/hexane (0% to 50%). The desired fractions were concentrated to a slurry and diluted with MTBE/hexane. The solid was collected by filtration and washed with minimal MTBE giving a third crop of 20 as a bright yellow solid (4.9% yield) with an overall yield of 80% from the three crops. LCMS (C18 column eluting with 10-90% CH$_3$CN/water gradient over 5 minutes with formic acid modifier) M+1: 363.48 (2.95 min). $^1$H NMR (300 MHz, CDCl$_3$) δ 8.84 (d, J=1.6 Hz, 2H), 8.27 (d, J=8.0 Hz, 1H), 7.62 (s, 2H), 5.31-5.24 (m, 1H), 4.63 (s, 1H), 4.27-4.18 (m, 1H), 3.97-3.87 (m, 1H), 2.33-2.05 (m, 4H), 1.64 (s, 6H) ppm.

Example 18

Preparation of 2-[5-(4,5-diamino-2-fluoro-3-tetrahydrofuran-2-yl-phenyl)pyrimidin-2-yl]propan-2-ol (21)

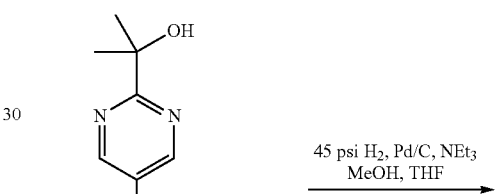

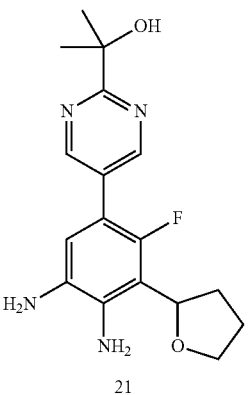

Placed 5% palladium on carbon (14.21 g, 50% wet, 3.339 mmol, Aldrich 330116) in a Parr bottle under nitrogen, followed by MeOH (242 mL, JT-Baker 909333) and NEt$_3$ (46.54 mL, 333.9 mmol, Sigma-Aldrich 471283). Dissolved 2-[5-(4-amino-2-fluoro-5-nitro-3-tetrahydrofuran-2-yl-phenyl)pyrimidin-2-yl]propan-2-ol (20) (121.0 g, 333.9 mmol) in hot THF (360 mL), allowed to cool, added to the reaction mixture, and rinsed with another portion of THF (124 mL). Placed the vessel on a Parr shaker and saturated with H$_2$. Added 45 psi H$_2$ and shook until consumption was complete (HPLC and LCMS showed complete reaction). The reaction mixture was purged with nitrogen, filtered through Celite™ and rinsed with EtOAc. It was re-filtered through paper (glass microfibre) and the filtrate concentrated in vacuo. Repeated the reaction three more times on the same scale and the batches were combined giving 21 as a brown solid (447 g, 99% yield; 93% HPLC purity). LCMS (C18 column eluting with 10-90% CH$_3$CN/water gradient over 5 minutes with formic acid modifier) M+1: 333.46 (1.79 min). $^1$H NMR (300 MHz, CDCl$_3$) δ 8.81 (d, J=1.4 Hz, 2H), 6.69 (d, J=7.3 Hz, 1H), 5.27-5.20 (m, 1H), 4.73 (s, 1H), 4.70 (s, 2H), 4.23-4.14 (m, 1H), 3.94-3.86 (m, 1H), 3.22 (s, 2H), 2.32-2.22 (m, 1H), 2.18-1.99 (m, 3H), 1.63 (s, 6H) ppm.

Example 19

Preparation of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22)

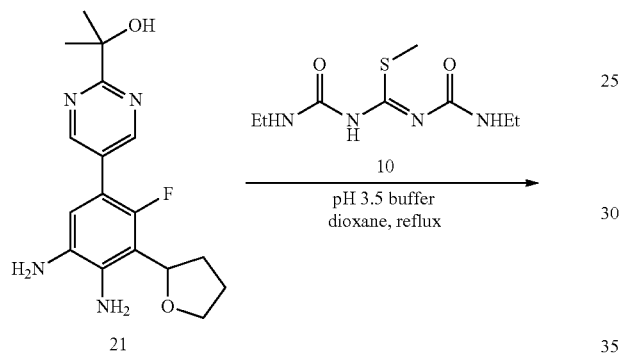

To a stirring suspension of 2-[5-(4,5-diamino-2-fluoro-3-tetrahydrofuran-2-yl-phenyl)pyrimidin-2-yl]propan-2-ol (21) (111.3 g, 334.9 mmol) and 1,4-dioxane (556.5 mL, Sigma-Aldrich 360481) was added 1-ethyl-3-(N-(ethylcarbamoyl)-C-methylsulfanyl-carbonimidoyl)urea (10) (93.36 g, 401.9 mmol, CB Research and Development) followed by a pH 3.5 buffer (1.113 L), prepared by dissolving NaOAc trihydrate (158.1 g) in 1N aqueous H$_2$SO$_4$ (1.100 L). The reaction mixture was stirred at reflux overnight (HPLC showed complete conversion), cooled to room temperature, and poured portion-wise (frothing) into a stirring solution of aqueous saturated NaHCO$_3$ (2.23 L) giving pH 8-9. This was stirred for 30 minutes, the solid was collected by filtration, washed copiously with water to neutral pH, and then more sparingly with EtOH. The solid was dried under reduced pressure giving 22 as an off-white yellowish solid (135.2 g, 94% yield; 99% HPLC purity). LCMS (C18 column eluting with 10-90% CH$_3$CN/water gradient over 5 minutes with formic acid modifier) M+1: 429.58 (2.03 min). $^1$H NMR (300 MHz, MeOD) δ 8.95 (d, J=1.6 Hz, 2H), 7.45 (d, J=6.5 Hz, 1H), 5.38 (br.s, 1H), 4.27 (dd, J=14.9, 7.1 Hz, 1H), 4.01 (dd, J=15.1, 7.0 Hz, 1H), 3.37-3.29 (m, 2H), 2.55 (br.s, 1H), 2.19-2.07 (m, 2H), 2.02-1.82 (br.s, 1H), 1.63 (s, 6H), 1.21 (t, J=7.2 Hz, 3H) ppm.

Example 20

Chiral chromatographic isolation of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23)

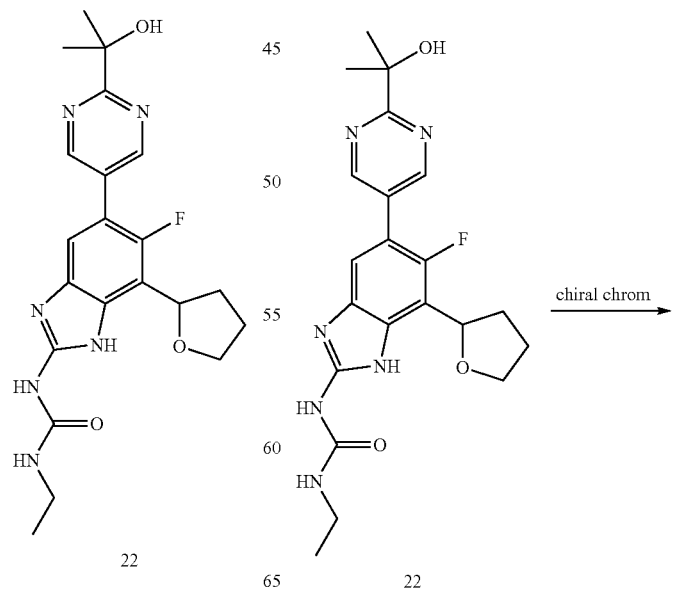

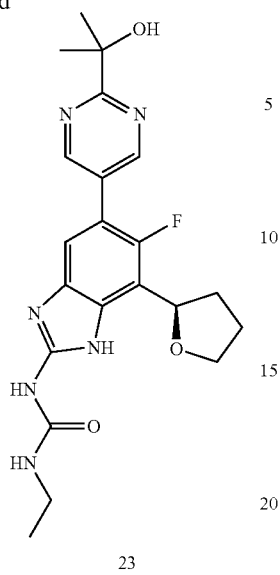

23

A racemic sample of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22) (133.60 g) was resolved on a CHIRALPAK® IC® column (by Chiral Technologies) eluting with DCM/MeOH/TEA (60/40/0.1) at 25° C. giving the desired enantiomer 23 as an off-white solid (66.8 g, 45% yield; 99.8% HPLC purity, 99+% ee). Analytical chiral HPLC retention time was 7.7 min (CHIRALPAK® IC® 4.6×250 mm column, 1 mL/min flow rate, 30° C.). The solid was suspended in 2:1 EtOH/Et₂O (5 volumes), stirred for 10 minutes, collected by filtration, washed with 2:1 EtOH/Et₂O, and dried under reduced pressure giving a white solid (60.6 g).

The structure and absolute stereochemistry of 23 were confirmed by single-crystal x-ray diffraction analysis. Single crystal diffraction data were acquired on a Bruker Apex II diffractometer equipped with sealed tube Cu K-alpha source (Cu Kα radiation, γ=1.54178 Å) and an Apex II CCD detector. A crystal with dimensions of 0.15×0.15×0.10 mm was selected, cleaned using mineral oil, mounted on a MicroMount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric P2₁ space group.

Figure 2:
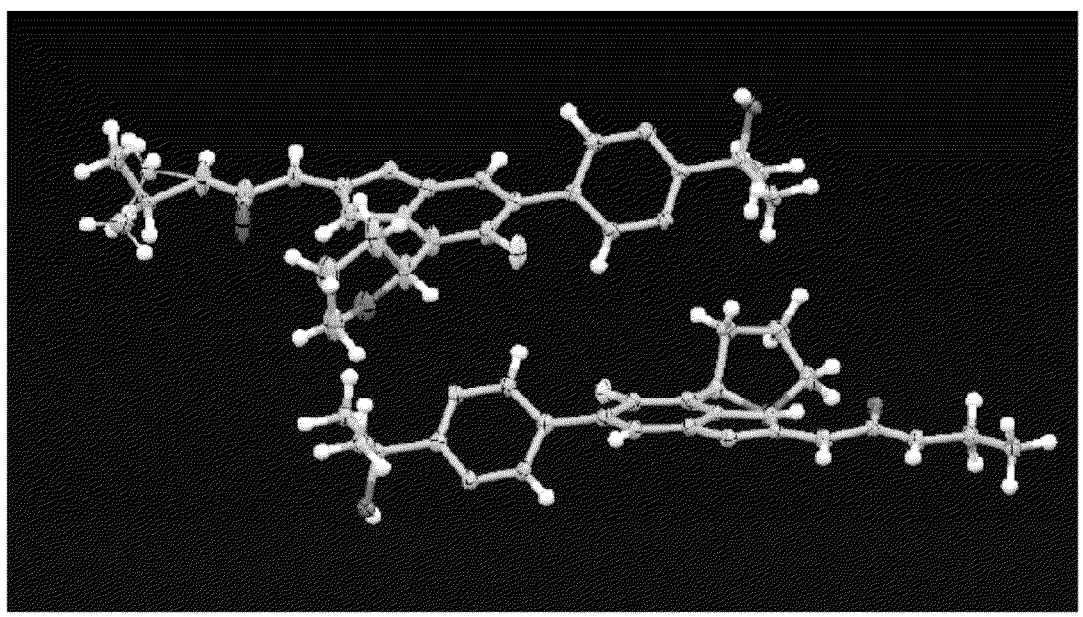
FIG. 2 is a thermal ellipsoid plot of two symmetry independent molecules of compound 23.

A diffraction data set of reciprocal space was obtained to a resolution of 0.85 Å using 0.5° steps using 30 s exposures for each frame. Data were collected at 100 (2) K. Integration of intensities and refinement of cell parameters were accomplished using APEXII software. Observation of the crystal after data collection showed no signs of decomposition. As shown in FIG. 2, there are two symmetry independent molecules in the structure and both symmetry independent molecules are R isomers.

The data were collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with P2₁ space group. The lattice parameters are a=9.9016(2) Å, b=10.9184(2) Å, c=19.2975(4) Å, β=102.826(1)°. Volume=2034.19(7) Å³.

Example 21

Preparation of the methanesulfonic acid salt of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23A)

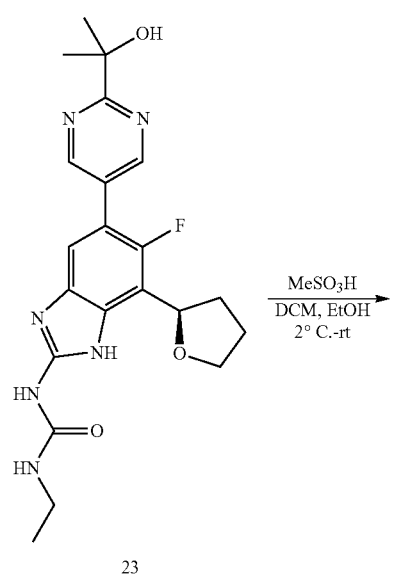

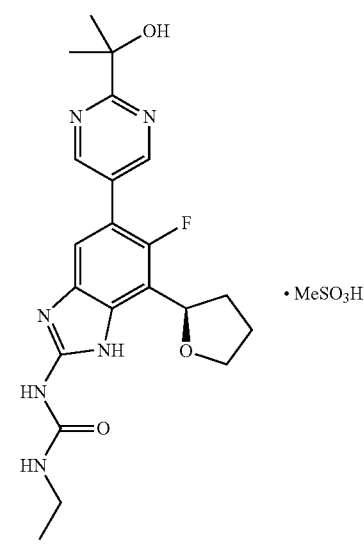

To a stirring suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (15.05 g, 35.13 mmol) in dichloromethane (60 mL, J. T. Baker 931533) and absolute ethanol (15 mL, Pharmco-AAPER 111000200) was added methanesulfonic acid (2.392 mL, 36.89 mmol, Sigma-Aldrich 471356). Stirred at room temperature until a clear solution was observed. Added heptane (300 mL) slowly over about 1 hr and collected the solid precipitate by filtration (using a Whatman qualitative #3 paper on top of a Whatman GF/F glass microfibre paper). Dried under reduced pressure in a vacuum oven (desiccated with calcium sulfate and potassium hydroxide) overnight at 40° C. giving 23A as a white solid (13.46 g, 99+% HPLC purity, 99+% ee). Analytical chiral HPLC shows one enantiomer with retention time of 8.6 min eluting with $CH_2Cl_2$/MeOH/TEA (60/40/0.1) on a CHIRALPAK® IC® 4.6×250 mm column with 1 mL/min flow rate at 30° C. A second crop of white solid product 23A (4.36 g, 98% HPLC purity, 99+% ee) was obtained from the filtrate. LCMS (C18 column eluting with 10-90% $CH_3CN$/water gradient over 5 minutes with formic acid modifier) M+1: 429.58 (2.03 min). $^1$H NMR (300 MHz, MeOD) δ 9.00 (d, J=1.6 Hz, 2H), 7.67 (d, J=6.1 Hz, 1H), 5.39 (t, J=7.7 Hz, 1H), 4.30 (dd, J=14.9, 6.9 Hz, 1H), 4.03 (dd, J=14.8, 7.7 Hz, 1H), 3.40-3.31 (m, 2H), 2.72 (s, 3H), 2.70-2.60 (m, 1H), 2.21-2.08 (m, 2H), 1.98-1.84 (m, 1H), 1.65 (s, 6H), 1.22 (t, J=7.2 Hz, 3H) ppm.

The (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea 23 may then be converted to the phosphate or phosphate salt prodrugs according to the schemes set forth below.

Scheme 1

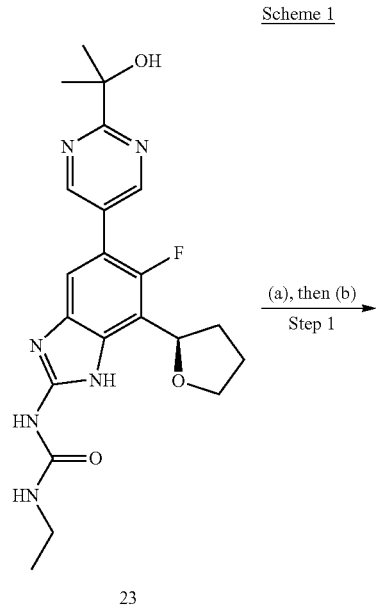

23

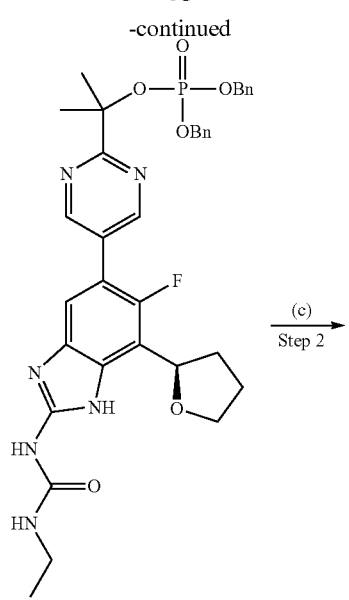

24

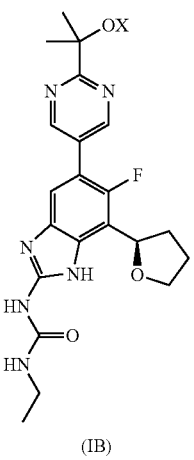

(IB)

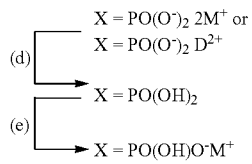

Reagents and conditions: (a) dibenzyl N,N-diisopropylphosphoramidite, tetrazole, 23° C., DMF; (b) mCPBA, 0-23° C., DMF; (c) $H_2$, Pd/C, $M^+OH^-$ or $D^{2+}(OH^-)_2$, EtOH, $H_2O$; (d) aq $H^+$; (e) aq $M^+OH^-$.

Compounds of formula (IB) may be prepared from compound 23 as shown in Scheme 1. In Step 1, compound 23 is treated with dibenzyl N,N-diisopropylphosphoramidite and tetrazole, followed by meta-chloroperoxybenzoic acid (mCPBA), to afford dibenzyl phosphate 24. In Step 2, hydrogenolysis of 24 in the presence of $M^+OH^-$ or $D^{2+}(OH^-)_2$ affords the dianionic form of the compound of formula (IB) (X=—PO(O$^-$)$_2$.2M$^+$or —PO(O$^-$)$_2$.D$^{2+}$). The free acid form of the compound of formula (IB) (X=PO(OH)$_2$) may be obtained by treating the dianionic form with aqueous acid. The monoanionic form of the compound of formula (IB) (X=PO(OH)O$^-$M$^+$) may be obtained by treating the free acid form with one equivalent of M$^+$OH$^-$.

Scheme 2

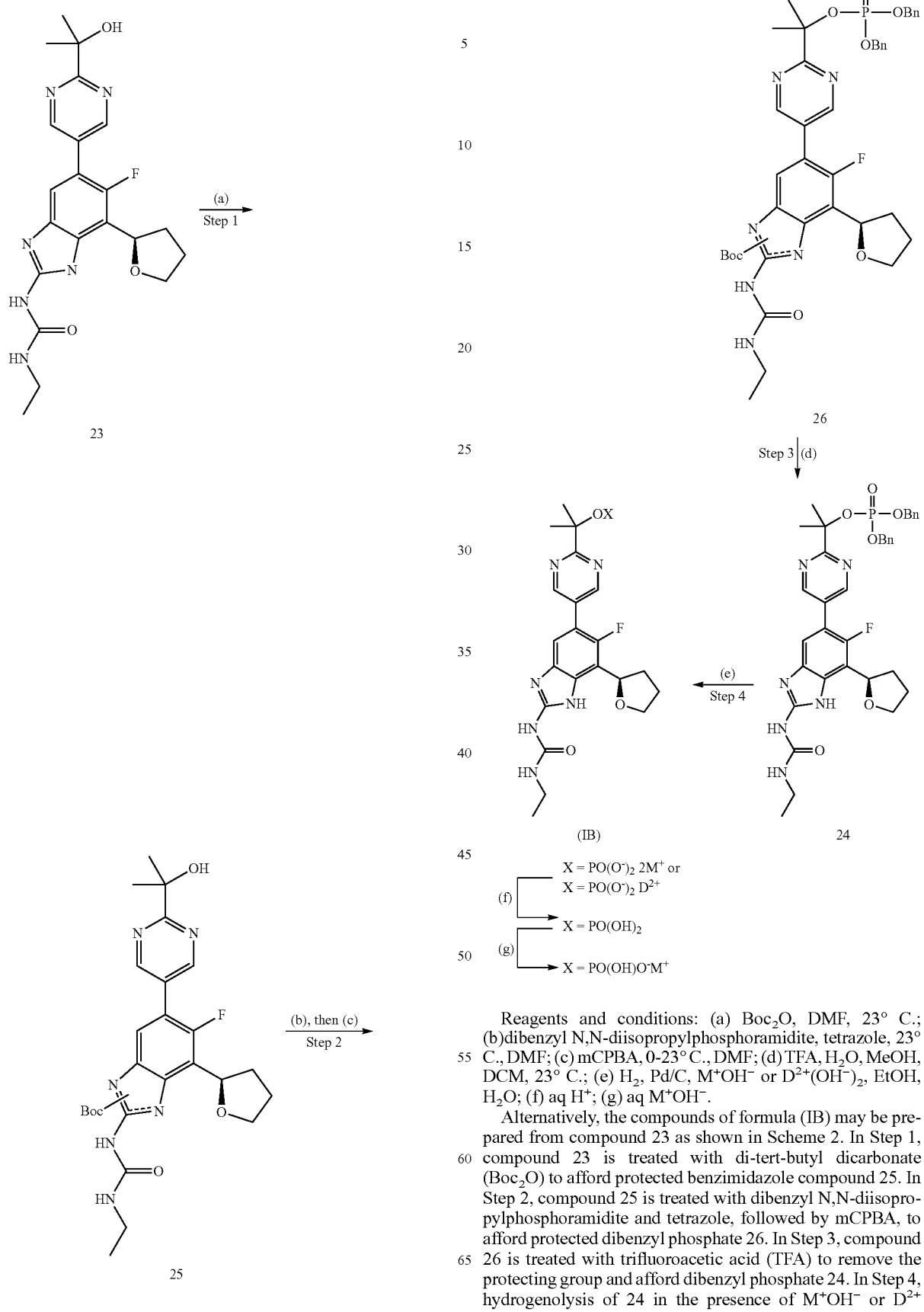

Reagents and conditions: (a) Boc₂O, DMF, 23° C.; (b) dibenzyl N,N-diisopropylphosphoramidite, tetrazole, 23° C., DMF; (c) mCPBA, 0-23° C., DMF; (d) TFA, H₂O, MeOH, DCM, 23° C.; (e) H₂, Pd/C, M⁺OH⁻ or D²⁺(OH⁻)₂, EtOH, H₂O; (f) aq H⁺; (g) aq M⁺OH⁻.

Alternatively, the compounds of formula (IB) may be prepared from compound 23 as shown in Scheme 2. In Step 1, compound 23 is treated with di-tert-butyl dicarbonate (Boc₂O) to afford protected benzimidazole compound 25. In Step 2, compound 25 is treated with dibenzyl N,N-diisopropylphosphoramidite and tetrazole, followed by mCPBA, to afford protected dibenzyl phosphate 26. In Step 3, compound 26 is treated with trifluoroacetic acid (TFA) to remove the protecting group and afford dibenzyl phosphate 24. In Step 4, hydrogenolysis of 24 in the presence of M⁺OH⁻ or D²⁺

(OH⁻)₂ affords the dianionic form of the compound of formula (IB) (X=—PO(O⁻)₂.2M⁺ or —PO(O⁻)₂.D²⁺). The free acid form of the compound of formula (IB) (X=PO(OH)₂) may be obtained by treating the dianionic form with aqueous acid. The monoanionic form of the compound of formula (I) (X=PO(OH)O⁻M⁺) may be obtained by treating the free acid form with one equivalent of M⁺OH⁻.

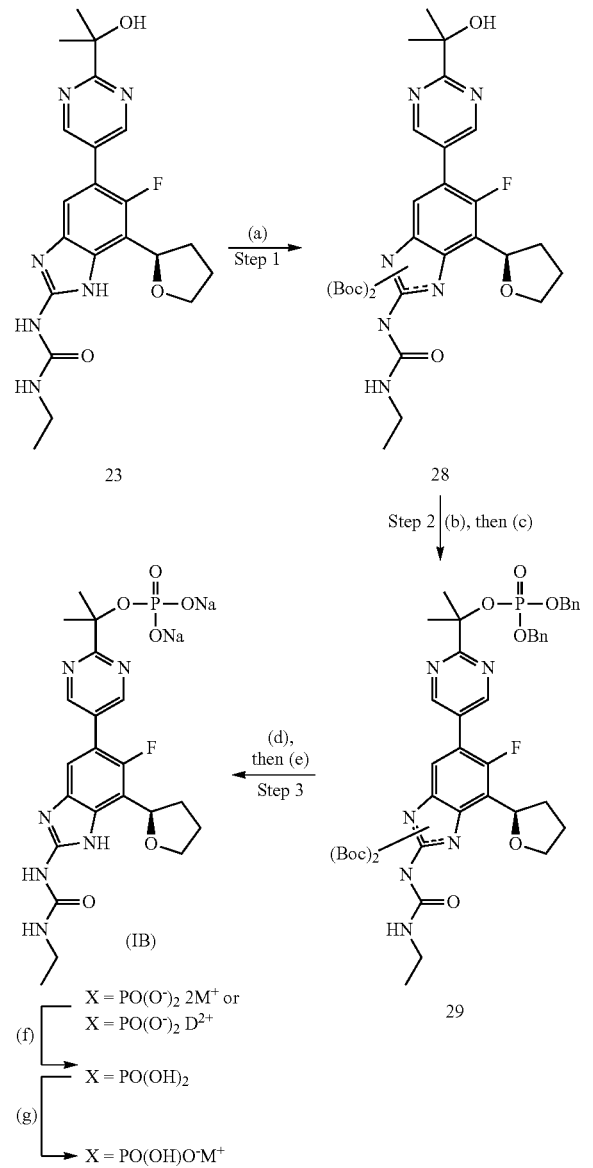

Reagents and conditions: (a) Boc₂O, DMAP, DMF, 23° C.; (b) dibenzyl N,N-diisopropylphosphoramidite, tetrazole, 23° C., DMF; (c) mCPBA, 0-23° C., DMF; (d) TFA, DCM; (e) aq M⁺OH⁻ or D²⁺(OH⁻)₂; (f) aq H⁺; (g) aq M⁺OH⁻.

The compounds of formula (IB) may also be prepared from compound 23 as shown in Scheme 3. In Step 1, compound 23 is treated with two equivalents of Boc₂O in the presence of N,N-dimethylaminopyridine (DMAP) to afford bis-protected benzimidazole compound 28. In Step 2, compound 28 is treated with dibenzyl N,N-diisopropylphosphoramidite and tetrazole, followed by mCPBA, to afford bis-protected dibenzyl phosphate 29. In Step 3, compound 29 is treated with TFA to remove the protecting groups. Treatment of the resulting intermediate with aqueous M⁺OH⁻ or D²⁺(OH⁻)₂ affords the dianionic form of the compound of formula (IB) (X=—PO(O⁻)₂.2M⁺ or —PO(O⁻)₂.D²⁺). The free acid form of the compound of formula (IB) (X=PO(OH)₂) may be obtained by treating the dianionic form with aqueous acid. The monoanionic form of the compound of formula (I) (X=PO(OH)O⁻M⁺) may be obtained by treating the free acid form with one equivalent of M⁺OH⁻.

Example 22

Preparation of (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24)

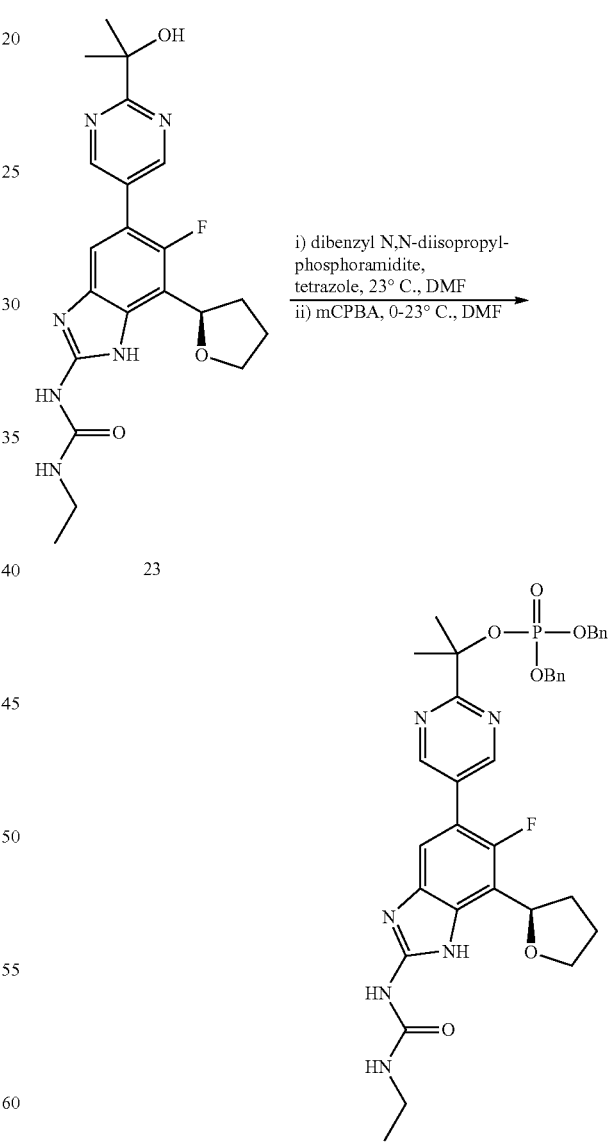

To 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (10.24 g, 23.66 mmol) in a 1 L round bottom flask under N₂ at 23° C. was added DMF (200 mL) followed by a solution of tetrazole (105.2 mL of 0.45 M in MeCN, 47.32 mmol) followed by N-dibenzyloxyphosphanyl-N-isopropyl-propan-2-amine (12.26 g, 11.93 mL, 35.49 mmol). After 4.5 h more N-dibenzyloxyphosphanyl-N-isopropyl-propan-2-amine (4 mL) was added. After stirring a further 16 h the reaction was cooled to 0° C. (ice-water bath) then treated with mCPBA (15.17 g, 61.52 mmol). The mixture was stirred at 0° C. for 30 min then at 23° C. for 30 min after which the reaction mixture was partitioned between water (400 mL) and EtOAc (700 mL). The organic layer was separated, washed with saturated aqueous sodium bicarbonate (500 mL), 10% aqueous sodium bisulfite (500 mL), saturated aqueous sodium bicarbonate (500 mL), and brine (500 mL) then dried (magnesium sulfate), filtered and concentrated. The residue was purified by MPLC using an ISCO COMBIFLASH brand flash chromatography purification system (330 g column) eluting with a 0-10% EtOH in DCM linear gradient over 16.5 column volumes at a 200 mL/min flow rate. After concentration in vacuo, (R)-dibenzyl 2-(5-(2-(3-ethylureido)-6-fluoro-7-(tetrahydrofuran-2-yl)-1H-benzo[a]imidazol-5-yl)pyrimidin-2-yl)propan-2-yl phosphate(24) (13.89 g, 20.17 mmol, 85.27%) was obtained as a white solid. ESMS (M+1)=689.5; ¹H NMR (300 MHz, CD₃OD) δ 8.88 (d, J=1.6 Hz, 2H), 7.37 (d, J=6 Hz, 1H), 7.30 (m, 10H), 5.38-5.33 (m, 1H), 5.12-5.01 (m, 4H), 4.24 (dd, J=6.8, 14.9 Hz, 1H), 3.98 (dd, J=6.9, 15.1 Hz, 1H), 3.35-3.27 (m, 3H), 2.52 (q, J=5.9 Hz, 1H), 2.14-2.05 (m, 2H), 1.91 (s, 6H) and 1.22-1.14 (m, 3H) ppm.

Example 23

Preparation of disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

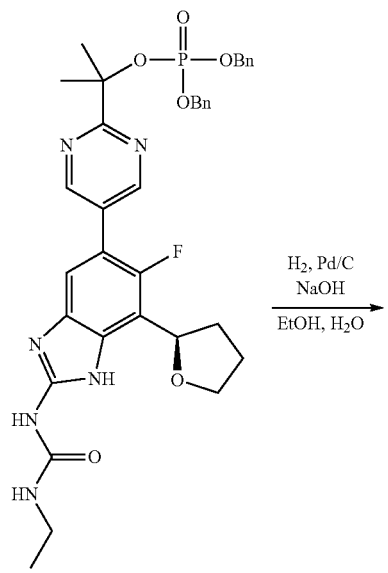

24

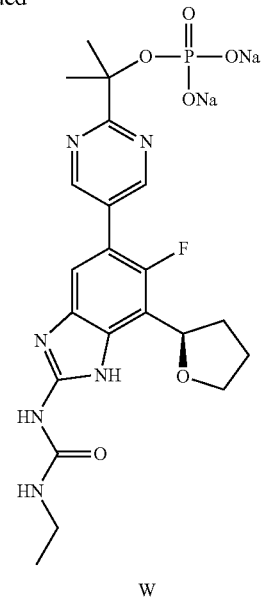

W

A 1 L Parr vessel was charged with water (200 mL), Pd/C (4 g, 10 wt % dry basis, wet, Degussa type), (R)-dibenzyl 2-(5-(2-(3-ethylureido)-6-fluoro-7-(tetrahydrofuran-2-yl)-1H-benzo[c]imidazol-5-yl)pyrimidin-2-yl)propan-2-yl phosphate(24) (13.89 g, 20.17 mmol), EtOH (400 mL) and aqueous 1 M NaOH (40.34 mL, 40.34 mmol). The resulting mixture was hydrogenated under 50 psi H₂ on a Parr shaker apparatus for 40 min. The reaction mixture was filtered through a 0.22 μm polyethersulfone (PES) membrane giving a dark colored filtrate. A water rinse resulted in more dark material crossing the filter membrane. The resulting filtrate was passed through a pad of Celite and the dark material did not elute until the pad was rinsed with water. The resulting dark solution (approx. 700 mL) was diluted with three volumes of EtOH (2100 mL), filtered through a 0.22 μm PES membrane (using 4 disposable Corning polystyrene filter systems, #431098) and the filtrate concentrated in vacuo. The resulting residue was dissolved in water (100 mL) and EtOH (300 mL), filtered through a 0.22 μm PES membrane to give a clear yellow solution, then passed through a Celite plug (26 mm diameter×60 mm height, pre-wet with EtOH) rinsing with EtOH (50 mL) and the filtrate then concentrated. The resulting residue was dissolved in water (250 mL) in a 1 L round bottom flask, then 1 M aqueous HCl (40 mL) was slowly added over 15 min with stirring to give a slurry of white solid. Twenty minutes following completion of the HCl addition, the solid was collected via filtration through a 0.22 μm PES membrane. The collected solid was washed with water (100 mL), then transferred (still wet) to a 1 L round bottom flask and slurried in MeOH (150 mL) for 30 min. The resulting fine white precipitate was collected via filtration then dried in vacuo overnight. The resulting free acid (9.17 g, 18.0 mmol) was treated with water (80 mL) then 1.0 N aq NaOH (36.0 mL, 2 equiv). The resulting solution was frozen and lyophilized to give disodium [1-[5-[2-(ethylcarbamoylamino)-6-fluoro-7-[(2R)-tetrahydrofuran-2-yl]-1H-benzimidazol-5-yl]pyrimidin-2-yl]-1-methyl-ethyl]phosphate (W) (10.206 g, 18.08 mmol, 89.66%) as a pale, cream-colored solid with consistent analytical data. ESMS (M+1) =509.4; ¹H NMR (300 MHz, D₂O) δ 8.58 (s, 2H), 6.92 (d, J=6.3 Hz, 1H), 5.13 (t, J=7.5 Hz, 1H), 3.98-3.81 (m, 2H), 3.04

(q, J=7.2 Hz, 2H), 2.26 (t, J=5.7 Hz, 1H), 1.97-1.92 (m, 2H), 1.67 (s, 6H) and 1.01 (t, J=7.2 Hz, 3H) ppm.

Example 24

Preparation of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25).

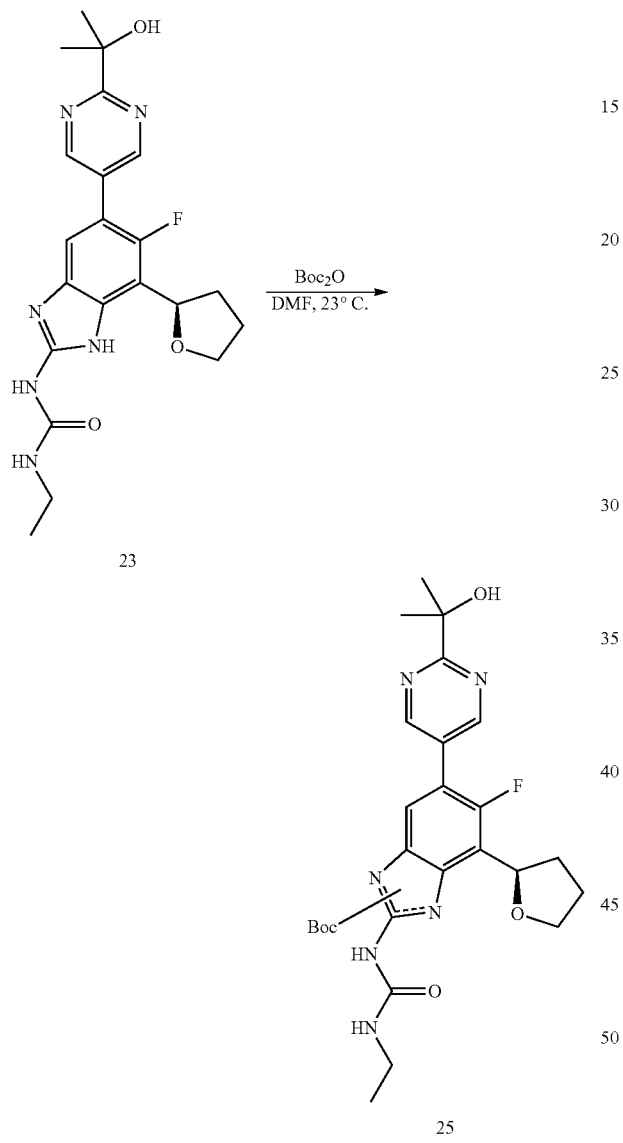

To a solution/suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (10.72 g, 25.02 mmol) in DMF (250 mL) at 23° C. was added Boc₂O (6.11 g, 28.00 mmol). After 2 hours, 2 M ammonia in MeOH (2 mL) was added to quench any excess Boc₂O. The quenched reaction mixture was partitioned between EtOAc and water (400 mL each), the organic layer separated, washed with water (2×400 mL) and brine (400 mL), then dried over MgSO₄, filtered and concentrated to give Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25) (12.69 g, 23.58 mmol, 94.26%) which was used without further purification. ESMS (M+1)=529.3; ¹H NMR (300.0 MHz, CDCl₃) δ 9.50 (s, 1H), 9.02 (t, J=5.3 Hz, 1H), 8.91 (d, J=1.6 Hz, 2H), 7.74 (d, J=6.5 Hz, 1H), 5.58 (t, J=7.8 Hz, 1H), 4.64 (s, 1H), 4.22 (q, J=7.4 Hz, 1H), 4.05 (td, J=7.8, 4.3 Hz, 1H), 3.47 (td, J=7.2, 4.3 Hz, 2H), 2.42-2.35 (m, 2H), 2.28-2.16 (m, 2H), 1.75 (s, 9H), 1.68 (s, 6H) and 1.31 (t, J=7.3 Hz, 3H) ppm.

Example 25

Preparation of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26)

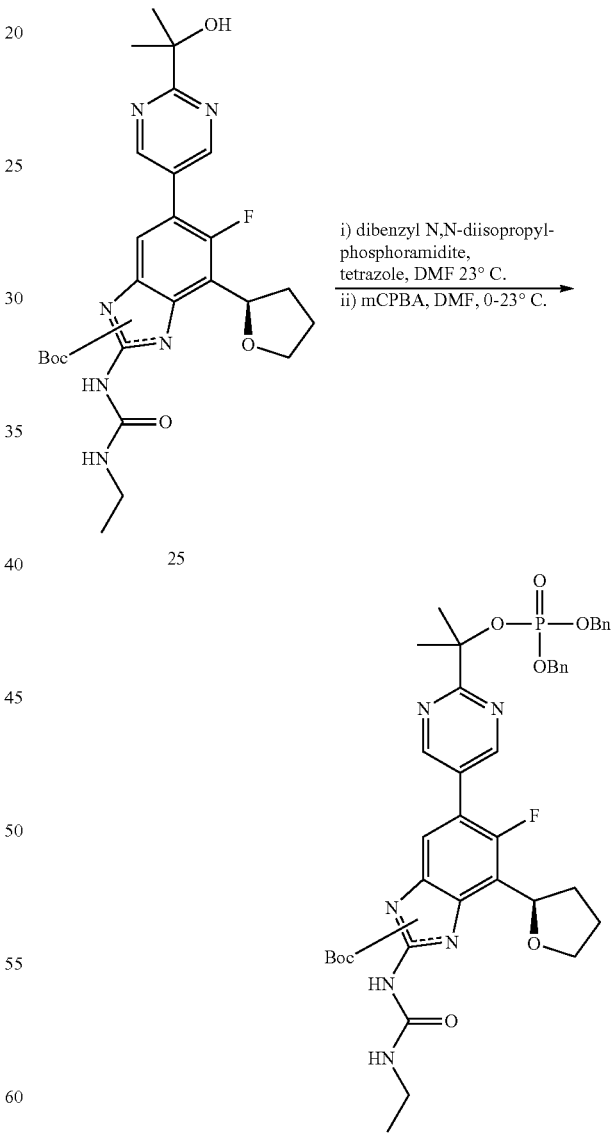

To Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25) (12.69 g, 23.58 mmol) and tetrazole (3.304 g, 47.16 mmol) under $N_2$ at 23° C. was added DCM (240 mL) followed by N-dibenzyloxyphosphanyl-N-isopropyl-propan-2-amine (9.775 g, 9.509 mL, 28.30 mmol). After 3 hours at 23° C., the reaction was cooled to 0° C. then mCPBA (6.977 g, 28.30 mmol) was added. The resulting solution was stirred for 45 min at 0° C. then for 20 min at 23° C. The reaction mixture was then partitioned between DCM (50 mL) and saturated aqueous sodium bicarbonate (400 mL). The organic layer was separated, then washed successively with aqueous sodium bisulfite (63 g in 350 mL water) and saturated aqueous sodium bicarbonate (400 mL), then dried over magnesium sulfate, filtered and concentrated in vacuo. The residue was purified by MPLC using an ISCO COMBI-FLASH brand flash chromatography purification system (330 g silica column) eluting with a 0-100% EtOAc in hexanes linear gradient over 16 column volumes at 200 mL/min. Product containing fractions were evaporated in vacuo to give Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26) (11.92 g, 15.11 mmol, 64.09%). ESMS (M+1)=789.2; $^1$H NMR (300.0 MHz, $CDCl_3$) δ 9.51 (s, 1H), 9.03 (t, J=5.4 Hz, 1H), 8.91 (d, J=1.6 Hz, 2H), 7.73 (d, J=6.5 Hz, 1H), 7.37-7.28 (m, 10H), 5.58 (t, J=7.8 Hz, 1H), 5.17-5.05 (m, 4H), 4.23 (t, J=7.5 Hz, 1H), 4.05 (td, J=7.8, 4.3 Hz, 1H), 3.53-3.44 (m, 2H), 2.39 (dd, J=7.9, 14.5 Hz, 2H), 2.28-2.15 (m, 2H), 1.98 (s, 6H), 1.72 (m, 9H) and 1.31 (t, J=7.2 Hz, 3H) ppm.

Example 26

Preparation of (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24)

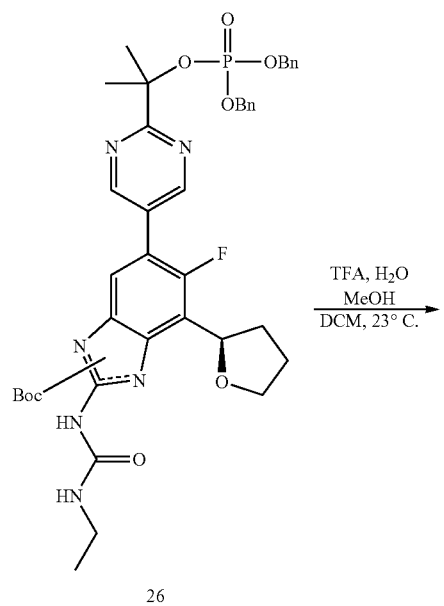

26

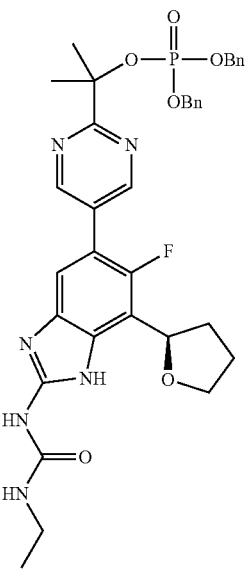

24

To a solution of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26) (11.9 g, 15.09 mmol) in DCM (300 mL) at 23° C. was added water (2.325 mL, 129.1 mmol) then TFA (3.441 g, 2.325 mL, 30.18 mmol). After 1 h, only partial conversion was observed by tlc, so more TFA (3.441 g, 2.325 mL, 30.18 mmol) was added. After a further 2.5 h, MeOH (2 mL) was added and the mixture stirred a further 18 hours. The reaction mixture was washed with 1:1 brine:saturated aqueous sodium bicarbonate (200 mL). The aqueous layer was re-extracted with DCM (150 mL), the organic layers combined, then dried (over magnesium sulfate), filtered and concentrated in vacuo. The resulting residue was re-dissolved in EtOAc (200 mL) washed with water (150 mL) and brine (100 mL), then dried (magnesium sulfate) filtered and concentrated to give (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24) (10.21 g, 14.83 mmol, 98.27%) as a white solid. ESMS (M+1)=689.4; $^1$H NMR (300 MHz, $CD_3OD$) δ 8.88 (d, J=1.6 Hz, 2H), 7.37 (d, J=6 Hz, 1H), 7.30 (m, 10H), 5.38-5.33 (m, 1H), 5.12-5.01 (m, 4H), 4.24 (dd, J=6.8, 14.9 Hz, 1H), 3.98 (dd, J=6.9, 15.1 Hz, 1H), 3.35-3.27 (m, 3H), 2.52 (q, J=5.9 Hz, 1H), 2.14-2.05 (m, 2H), 1.91 (s, 6H) and 1.22-1.14 (m, 3H) ppm.

Example 27

Preparation of disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

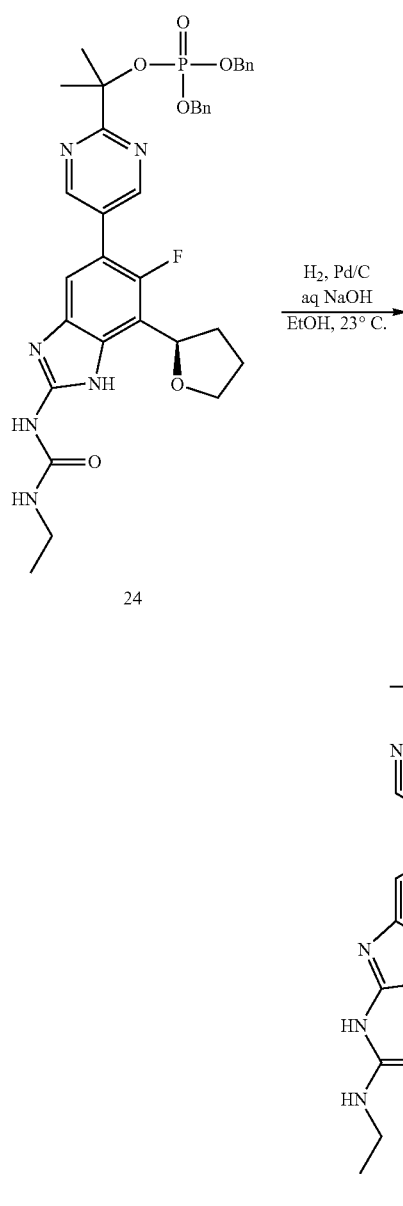

A 1 L round bottom flask was charged with (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24) (9.37 g, 13.61 mmol), EtOH (300 mL), water (150 mL), Pd/C (10 wt % dry basis, wet, Degussa type, 3 g) and 1 M aqueous NaOH (27.22 mL, 27.22 mmol). The suspension was evacuated for 3 min (needle to pump) then placed under an atmosphere of hydrogen gas (balloon). After stirring 2.5 h at 23° C., the reaction was filtered through a 0.22 μm PES membrane (disposable Corning filter system, 1 L, polystyrene, #431098) to remove catalyst and washed with EtOH (50 mL). The resulting solution was concentrated, the residue dissolved in water (80 mL), treated with MeCN (80 mL), then frozen and lyophilized to give disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W) (7.10 g, 12.81 mmol, 94.12%) as a white solid. ESMS (M+1)= 509.3; $^1$H NMR (300 MHz, D$_2$O) δ 8.58 (s, 2H), 6.92 (d, J=6.3 Hz, 1H), 5.13 (t, J=7.5 Hz, 1H), 3.98-3.81 (m, 2H), 3.04 (q, J=7.2 Hz, 2H), 2.26 (t, J=5.7 Hz, 1H), 1.97-1.92 (m, 2H), 1.67 (s, 6H) and 1.01 (t, J=7.2 Hz, 3H) ppm.

Example 28

Preparation of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (28)

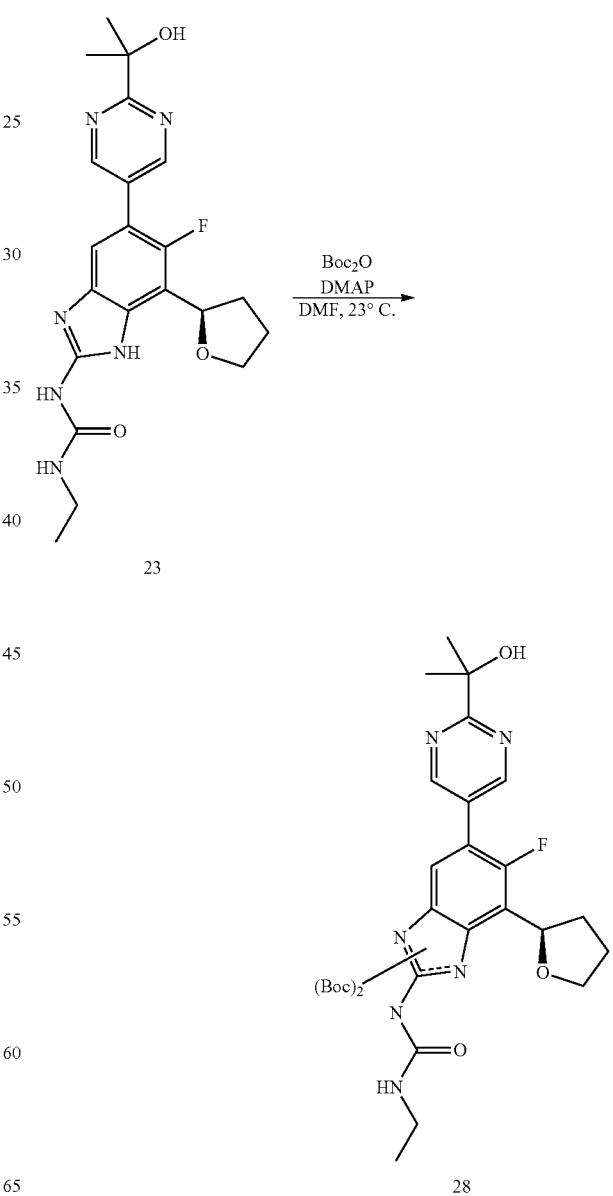

To a solution/suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (1.333 g, 3.111 mmol) in DMF (30 mL) was added DMAP (38.01 mg, 0.3111 mmol) followed by Boc₂O (1.426 g, 1.501 mL, 6.533 mmol). After 30 min, the reaction mixture was diluted with water and EtOAc (300 mL each), the organic layer separated, washed with water and brine (300 mL each), then dried over magnesium sulfate, filtered and concentrated. The residue was purified by MPLC using an ISCO COMBIFLASH brand flash chromatography purification system (80 g silica column) eluting with a 0-60% EtOAc in hexanes linear gradient over 20 column volumes at 60 mL/min flow rate. Desired product fractions were combined and evaporated to give diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (28) (1.43 g, 2.275 mmol, 73.11%) as a clear foam. ESMS (M+1)=629.3; ¹H NMR (300.0 MHz, CDCl₃) δ 8.95 (d, J=1.6 Hz, 2H), 8.31-8.27 (m, 1H), 8.05 (d, J=6.5 Hz, 1H), 5.80-5.68 (m, 1H), 4.70 (s, 1H), 4.21-4.09 (m, 1H), 3.98 (d, J=6.4 Hz, 1H), 3.42-3.37 (m, 2H), 2.45-2.00 (m, 4H), 1.65 (s, 6H), 1.62 (s, 9H), 1.37 (s, 9H) and 1.28-1.21 (m, 3H) ppm.

Example 29

Preparation of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29)

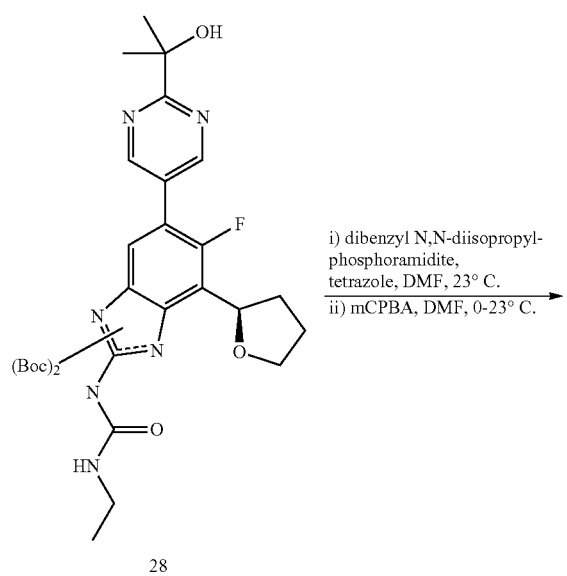

i) dibenzyl N,N-diisopropyl-phosphoramidite, tetrazole, DMF, 23° C.
ii) mCPBA, DMF, 0-23° C.

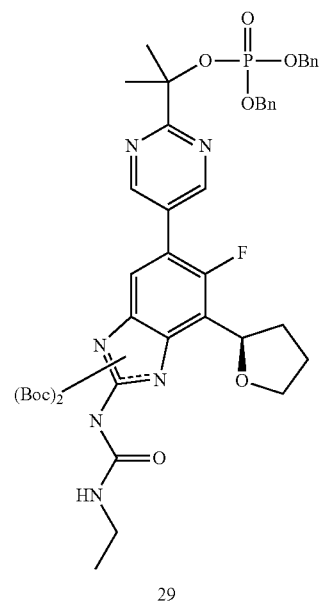

To diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (28) (1.13 g, 1.797 mmol) and tetrazole (251.8 mg, 3.594 mmol) at 23° C. under N₂ was added DCM (30 mL) followed by N-dibenzyloxyphosphanyl-N-isopropyl-propan-2-amine (744.7 mg, 724.4 µL, 2.156 mmol). After stirring for 18 h, the reaction was cooled to 0° C. then treated with mCPBA (531.5 mg, 2.156 mmol). The reaction was stirred for 15 min at 0° C., then for 30 min at 23° C. The resulting solution was then partitioned between EtOAc and saturated aqueous sodium bicarbonate (300 mL each), the organic layer separated, then washed with 10% aqueous sodium bisulfite, saturated aqueous sodium bicarbonate and brine (300 mL each), then dried over magnesium sulfate filtered and concentrated. The residue was purified by MPLC using an ISCO COMBIFLASH brand flash chromatography purification system (80 g silica column) eluting with a 0-80% EtOAc in hexanes linear gradient over 20 column volumes at 60 mL/min flow rate. Desired product fractions were combined and evaporated to give diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29) (1.03 g, 1.159 mmol, 64.50%) as a clear, glassy oil. ESMS (M+1)=889.5; ¹H NMR (300.0 MHz, CDCl₃) δ 8.93 (d, J=1.5 Hz, 2H), 8.31 (s, 1H), 8.04 (d, J=6.4 Hz, 1H), 7.36-7.26 (m, 10H), 5.83-5.70 (m, 1H), 5.16-5.05 (m, 4H), 4.24-4.18 (m, 1H), 4.03-3.97 (m, 1H), 3.42-3.36 (m, 2H), 2.43-2.05 (m, 4H), 1.98 (s, 6H), 1.64 (s, 9H), 1.40 (s, 9H) and 1.26 (t, J=7.2 Hz, 3H) ppm.

Example 30

Preparation of sodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

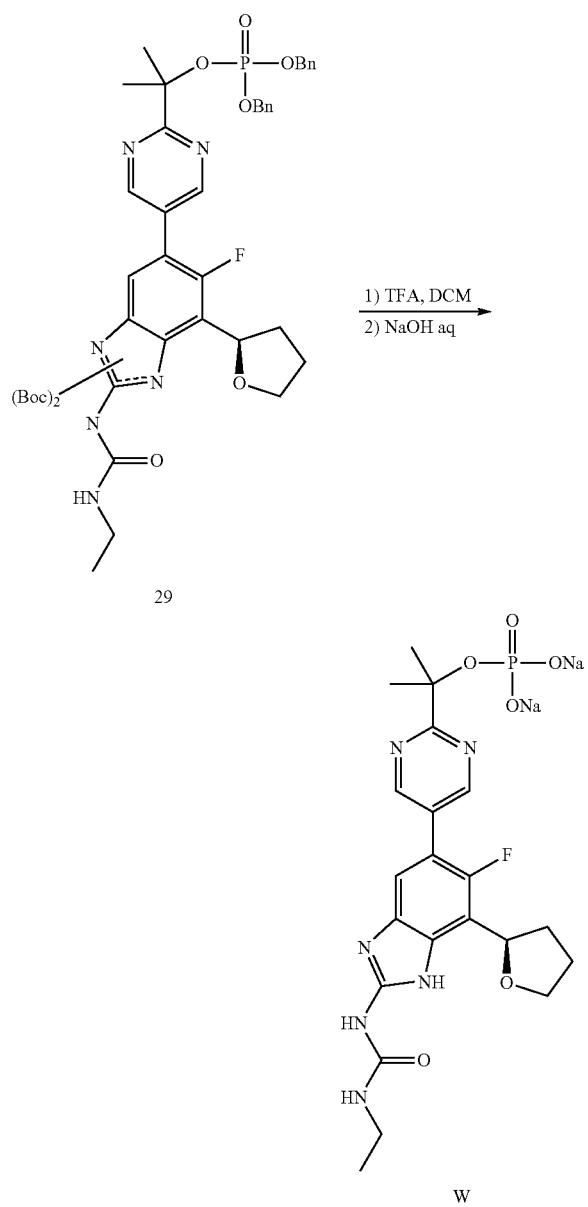

To a solution of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29) (121 mg, 0.1361 mmol) in DCM (10 mL) at 23° C. was added TFA (5 mL). After 2 h, the reaction mixture was concentrated in vacuo. The residue was dissolved in MeOH (6 mL) and treated with approx 0.5 mL 2 M $NH_3$ in MeOH (to fully dissolve the material). The resulting solution was purified in 6 injections on preparative HPLC, reverse phase, Sunfire prep C18 OBD 5 µM column 19×100 mm; eluting with a 10-90% aq MeCN w/0.1% TFA buffer, linear gradient over 15 min at 20 mL/min flow rate. Fractions containing product were pooled and lyophilized. The resulting material was suspended in MeOH (3 mL), stirred at 23° C. for 30 min, then the precipitate was collected via filtration through a plastic frit. The resulting white solid was re-subjected to a MeOH slurry (3 mL), then collected via filtration to give 68 mg of white solid after drying. The white solid was treated with 0.10 M aq NaOH (2.68 mL, 2 equiv NaOH) to give a solution that was then passed through an Acrodisc CR 13 mm syringe filter with 0.45 µm PTFE membrane, flushing with water (2 mL). The resulting solution was treated with MeCN (3 mL), frozen and lyophilized to give sodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W) as a white powder. ESMS (M+1)=509.2; $^1$H NMR (300 MHz, $D_2O$) δ 8.58 (s, 2H), 6.92 (d, J=6.3 Hz, 1H), 5.13 (t, J=7.5 Hz, 1H), 3.98-3.81 (m, 2H), 3.04 (q, J=7.2 Hz, 2H), 2.26 (t, J=5.7 Hz, 1H), 1.97-1.92 (m, 2H), 1.67 (s, 6H) and 1.01 (t, J=7.2 Hz, 3H) ppm.

Example 31

Susceptibility Testing in Liquid Media

Compounds of this invention were tested for antimicrobial activity by susceptibility testing in liquid media. Such assays were performed within the guidelines of the latest CLSI document governing such practices: "M07-A8 Methods for Dilution Antimicrobial Susceptibility Tests for Bacteria that Grow Aerobically; Approved Standard—Eighth Edition (2009)". Other publications such as "Antibiotics in Laboratory Medicine" (Edited by V. Lorian, Publishers Williams and Wilkins, 1996) provide essential practical techniques in laboratory antibiotic testing. The specific protocols used were as follows:

Protocol #1: Gyrase MIC Determination of Compounds Using Microdilution Broth Method Materials:
Round bottom 96-well microtiter plates (Costar 3788)
Mueller Hinton II agar plates (MHII; BBL premix)
Mueller Hinton II liquid broth (MHII; BBL premix)
BBL Prompt Inoculation System (Fisher B26306)
Test Reading Mirror (Fisher)
Agar plates with bacteria streaked to single colonies, freshly prepared
Sterile DMSO
Human serum (U.S. Biologicals S1010-51)
Laked horse blood (Quad Five 270-100)
Resazurin 0.01%
Sprague Dawley Rat serum (U.S. Biologicals 1011-90B or Valley BioMedical AS3061 SD)
Pooled Mouse serum (Valley BioMedical AS3054)
Strains (Media, Broth and Agar):
1. *Staphylococcus aureus* ATCC #29213
   a. MHII
   b. MHII+50% human serum
   c. MHII+50% rat serum
   d. MHII+50% mouse serum
2. *Staphylococcus aureus* ATCC #29213 GyrB T1731 (MHII)
3. *Staphylococcus aureus*, JMI collection strains; see table 5 (MHII)
4. *Staphylococcus epidermidis*, JMI collection strains; see table 5 (MHII)
5. *Enterococcus faecalis* ATCC #29212 (MHII+3% laked horse blood)

6. *Enterococcus faecium* ATCC #49624 (MHII+3% laked horse blood)
7. *Enterococus faecalis*, JMI collection strains; see table 5 (MHII+3% laked horse blood)
8. *Enterocus faecium*, JMI collection strains; see table 5 (MHII+3% laked horse blood)
9. *Streptococcus pneumoniae* ATCC #10015 (MHII+3% laked horse blood)
10. *Streptococcus pneumoniae*, JMI collection strains; see table 5 (MHII+3% laked horse blood)
11. β-haemolytic streptococci, Groups A, B, C, G) JMI collection strains; see table 5 (MHII+3% laked horse blood)
12. *Bacillus cereus* ATCC 10987 (MHII)
13. *Bacillus cereus* ATCC 14579 (MHII)
14. *Bacillus subtilis* ATCC 6638 (MHII)
15. *Bacillus subtilis* (168) ATCC 6051 (MHII)

Inoculum Prep (for all Strains Other than *S. Aureus*+50% Sera):

1. Using the BBL Prompt kit, picked 5 big or 10 small, well separated colonies from culture grown on the appropriate agar medium as indicated above and inoculated 1 mL of sterile saline provided in the kit.
2. Vortexed the wells for ~30 s to provide a suspension of ~$10^8$ cells/mL. Actual density could be confirmed by plating out dilutions of this suspension.
3. Diluted the suspension 1/100 by transferring 0.15 mL of cells into 15 mL (~$10^6$ cells/mL) sterile broth (or see below) for each plate of compounds tested, then swirled to mix. If more than 1 plate of compounds (>8 compounds) were tested, volumes were increased accordingly.
   a. For *E. faecalis, E. faecium* and *S. pneumoniae*: 14.1 mL MHII+0.9 mL laked horse blood was used.
4. Used 50 μl cells (~$5\times10^4$ cells) to inoculate each microtiter well containing 50 μl of the drug diluted in broth (see below).

Drug Dilutions, Inoculation, MIC Determination:

1. All drug/compound stocks were prepared at 12.8 mg/mL concentration, usually in 100% DMSO.
2. Diluted drug/compound stocks to 200× desired final concentration in 50 μL DMSO. If starting concentration of MICs was 8 μg/mL final concentration, then required 6.25 μL of stock+43.75 μL DMSO. Each 200× stock was placed in a separate row of column 1 of a new 96 well microtiter plate.
3. Added 25 μL of DMSO to columns 2-12 of all rows of the microtiter plate containing 200× compound stocks and serially diluted 25 μL from column 1 through column 11, changed tips after each column. i.e. 25 μL compound+25 μL DMSO=2× dilution. Left "no compound" DMSO well at the end of the series for control.
4. For each strain tested (except *S. aureus*+50% human serum), prepared two microtiter plates with 50 μL of MHII broth using a Matrix pipettor.
5. Transferred 0.5 μL of each dilution (w/Matrix auto-pipettor) to 50 μL of medium/microtiter well prior to the addition of 50 μl of cells. The usual starting concentration of compound was 8 μg/mL after the 1/200 dilution into medium+cells–compound concentrations decreased in 2× steps across the rows of the microtiter plate. All MICs were done in duplicate.
6. All wells were inoculated with 50 μl of diluted cell suspension (see above) to a final volume of 100 μl.
7. After inoculum was added, mixed each well thoroughly with a manual multichannel pipettor; same tips were used going from low to high concentration of drug in the same microtiter plate.
8. Plates were incubated at 37° C. for at least 18 hours.
9. Plates were viewed with a test reading mirror after 18 hours and the MIC was recorded as the lowest concentration of drug where no growth was observed (optical clarity in the well).

Preparation of *S. Aureus*+50% Human Serum, *S. Aureus*+50% Rat Serum or *S. Aureus*+50% Mouse Serum.

1. Prepared 50% serum media by combining 15 mL of MHII+15 mL human serum—total 30 mL. Increased volume in 30 mL increments when more than 1 compound plate was tested.
2. Used the same BBL Prompt inoculum of *S. aureus* ATCC #29213 as described above, diluted 1/200 by transferring 0.15 mL of cells into 30 mL (~$5\times10^5$ cells/mL) of the 50% human serum media prepared above and swirled to mix.
3. Filled all test wells of the desired number of microtiter plates with 100 μL cells in 50% serum media.
4. Transferred 0.5 μL of each compound dilution (w/Matrix auto-pipettor) to 100 μL of cells/media. The usual starting concentration of compound was 8 μg/mL after the 1/200 dilution into medium+cells–compound concentrations decreased in 2× steps across the rows of a microtiter plate. All MICs were done in duplicate.
5. Mixed each well thoroughly with a manual multichannel pipettor; same tips were used going from low to high concentration of drug in the same microtiter plate.
6. Plates were incubated at 37° C. for at least 18 hours. After incubation, added 25 μL of 0.01% Resazurin to each well and continued to incubate at 37° C. for at least 1 additional hour or until the Resazurin color changes.
7. Plates were viewed with a test reading mirror and the MIC was recorded. When using Resazurin, the color of the dye changed from a dark blue to a bright pink in wells with no growth. The lowest concentration of drug that turned the dye pink was the MIC.

Protocol 2: Gyrase MIC Determination of Compounds Against Gram Negatives Using Microdilution Broth Method Materials:
Round bottom 96-well microtiter plates (Costar 3788)
Mueller Hinton II agar plates (MHII; BBL premix)
Mueller Hinton II liquid broth (MHII; BBL premix)
BBL Prompt Inoculation System (Fisher b26306)
Test Reading Mirror (Fisher)
Agar plates with bacteria streaked to single colonies, freshly prepared
Sterile DMSO
Strains (MHII Media for all; Broth and Agar):

1. *Escherichia coli* ATCC #25922
2. *Escherichia coli*, JMI collection strains, see table 5
3. *Escherichia coli* AG100 WT
4. *Escherichia coli* AG100 tolC
5. *Acinetobacter baumannii* ATCC #BAA-1710
6. *Acinetobacter baumannii* ATCC #19606
7. *Acinetobacter baumannii*, JMI collection strains, see table 5
8. *Klebsiella pneumoniae* ATCC #BAA-1705
9. *Klebsiella pneumoniae* ATCC #700603
10. *Klebsiella pneumoniae*, JMI collection strains, see table 5
11. *Moraxella catarrhalis* ATCC#25238
12. *Moraxella catarrhalis* ATCC#49143

13. *Moraxella catarrhalis*, JMI collection strains, see table 5
14. *Haemophilus influenzae* ATCC 49247
15. *Haemophilus influenzae* (Rd1 KW20) ATCC 51907
16. *Haemophilus influenzae* Rd0894 (AcrA-)
17. *Haemophilus influenzae*, JMI collection strains, see table 5
18. *Pseudomonas aeruginosa* PAO1
19. *Pseudomonas aeruginosa*, JMI collection strains, see table 5
20. *Proteus mirabilis*, JMI collection strains, see table 5
21. *Enterobacter cloacae*, JMI collection strains, see table 5
22. *Stenotrophomonas maltophilia* ATCC BAA-84
23. *Stenotrophomonas maltophilia* ATCC13637

Inoculum Prep:
1. Using the BBL Prompt kit, picked 5 big or 10 small, well separated colonies from cultures grown on agar medium and inoculated 1 mL sterile saline that came with the kit.
2. Vortexed the wells for ~30 s to give a suspension of ~$10^8$ cells/mL. Actual density could be confirmed by plating out dilutions of this suspension.
3. Diluted the suspension 1/100 by transferring 0.15 mL of cells into 15 mL (~$10^6$ cells/mL) sterile broth (see below) for each plate of compounds tested, swirled to mix. If more than 1 plate of compounds (>8 compounds) was to be tested, increased volumes accordingly.
4. Used 50 µl cells (~$5 \times 10^4$ cells) to inoculate each microtiter well containing 50 µl of the drug diluted in broth (see below).

Drug Dilutions, Inoculation, MIC Determination:
1. All drug/compound stocks were prepared at 12.8 mg/mL concentration, usually in 100% DMSO.
2. Diluted drug/compound stocks to 200× desired final concentration in 50 µL DMSO. If starting concentration of MICs was 8 µg/mL final concentration, then required 6.25 µL of stock+43.75 µL DMSO. Each 200× stock was placed in a separate row of column 1 of a new 96 well microtiter plate.
3. Added 25 µL of DMSO to columns 2-12 of all rows of the microtiter plate containing 200× compound stocks and serially diluted 25 µL from column 1 through column 11, changed tips after each column. i.e. 25 µL compound+25 µL DMSO=2× dilution. Left "no compound" DMSO well at the end of the series for control.
4. For each strain tested, prepared two microtiter plates with 50 µL of MHII broth using a Matrix pipettor.
5. Transferred 0.5 µL of each dilution (w/Matrix autopipettor) to 50 µL of medium/microtiter well prior to the addition of 50 µl of cells. The usual starting concentration of compound was 8 µg/mL after the 1/200 dilution into medium+cells–compound concentrations decreased in 2× steps across the rows of a microtiter plate. All MICs were done in duplicate.
6. All wells were inoculated with 50 µl of diluted cell suspension (see above) to a final volume of 100 µl.
7. After inoculum was added, each well was mixed thoroughly with a manual multichannel pipettor; same tips were used going from low to high concentration of drug in the same microtiter plate.
8. Plates were incubated at 37° C. for at least 18 hours.
9. Plates were viewed with a test reading mirror after 18 hours and the MIC was recorded as the lowest concentration of drug where no growth was observed (optical clarity in the well).

Protocol #3: Gyrase MIC Determination of Compounds Using Agar Dilution Method

Materials:
Petri plates 60×15 mm (Thermo Scientific Cat. #12567100)
Centrifuge tubes, 15 mL (Costar)
BBL Prompt Inoculation System (Fisher b26306)
Agar plates with bacteria streaked to single colonies, freshly prepared
Sterile DMSO
GasPak™ incubation containers (BD Cat. #260672)
GasPak™ EZ Anaerobe container system sachets (BD Cat. #260678)
GasPak™ EZ C02 container system sachets (BD Cat. #260679)
GasPak™ EZ Campy container system sachets (BD Cat. #260680)

Strains:
1. *Clostridium difficile* ATCC BAA-1382;
2. *Clostridium difficile*, CMI collection strains, see table 4
3. *Clostridium perfringens*, CMI collection strains, see table 4
4. *Bacteroides fragilis* and *Bacteroides* spp., CMI collection strains, see table 4
5. *Fusobacterium* spp., CMI collection strains, see table 4
6. *Peptostreptococcus*, spp., CMI collections strains, see table 4
7. *Prevotella* spp., CMI collection strains, see table 4
8. *N. gonorrhoeae* ATCC 35541
9. *N. gonorrhoeae* ATCC 49226
10. *Neisseria gonorrhoeae*, JMI collection strains, see table 4
11. *Neisseria meningitidis*, JMI collection strains, see table 4

Media Preparation and Growth Conditions:
Growth medium recommended for each microbial species was prepared according to the CLSI publication 'M11-A7 Methods for Antimicrobial Susceptibility Testing of Anaerobic Bacteria; Approved Standard—Seventh Edition (2007)' with the exception of *N. gonorrhoeae* and *N. meningitidis* for which media was prepared according to "M07-A8 Methods for Dilution Antimicrobial Susceptibility Tests for Bacteria that Grow Aerobically; Approved Standard—Eighth Edition (2009)".

Plate Pouring:
1. Prepared 100× drug stocks of each test compound as described in Table 1. Used a 15 mL centrifuge tube, added 100 uL of each drug stock to 10 mL of molten agar (cooled to ~55° C. in water bath). Mixed by inverting tube 2-3× then pour into individually labeled 60×15 mm Petri dish.
2. Routine test concentrations were: 0.002 ug/mL-16 ug/mL (14 plates).
3. Poured 4 drug free plates: 2 as positive control, 2 as aerobic control.
4. Allowed plates to dry. Used same day or stored overnight at RT or stored up to 3 days at 4° C.
5. Plates were labeled accordingly for drug concentration and strain placement.

Growth of Cells Requiring the Maintenance of an Anaerobic Environment:
1. All work performed with anaerobic bacteria was done as rapidly as possible; work performed in biosafety cabinets (i.e., aerobic environment) was completed in less then 30 minutes before cells were returned to anaerobic chambers.

2. Incubation of anaerobic bacteria was achieved using GasPak™ chambers. The large box style chambers (VWR 90003-636) required 2 anaerobic sachets (VWR 90003-642), while the tall cylinder style chambers (VWR 90003-602) only required 1 sachet.

Plate Inoculation (Performed in Biosafety Cabinet):

1. Streaked each strain onto individual agar plates as described above. Incubated for required time and environmental condition (i.e. anaerobic, microaerophilic, etc).

2. Used direct colony suspension method to suspend loopfuls of freshly streaked cells into ~4 mL 0.9% $NaCl_2$ and vortexed.
3. Adjusted suspension to $O.D._{600}$ 0.05 ($5 \times 10e7$ cfu/mL). Vortexed to mix.
4. Transferred ~0.2 mL of adjusted, mixed cultures to a 96 well plate. When ≤5 strains were tested, all strains were lined together in a single row. When testing >5 strains, transferred strains into plate with no more that 5 strains in a single row. This was necessary to fit on the small plates.
5. Used multi-channel pipettor, spotted 0.002 mL of each strain from prepared 96 well plates onto each MIC test plate. This resulted in ~$1 \times 10e5$ cfu/spot. When testing *C. difficile*, strains swarmed when grown, however distance between multi-channel pipettor spots was far enough such that swarming cells did not impair assay results.
   a. Inoculated 2 drug free plates first, while the other 2 drug free plates were inoculated last after the MIC test plates. The former and latter served as growth and inoculation controls. Incubated one plate from each set of drug-free controls under required atmospheric conditions with MIC plates and one set aerobically to test for contamination with aerobic bacteria. Aerobic culture was negative for growth when working with strict anaerobe or microaerophilic strain. Some growth was visible with *N. gonorrhoeae*.
6. Allowed inoculum to dry (for as short a time as necessary), then placed upside down in GasPak with appropriate number of sachets and incubate.
7. *Neisseria* spp. were incubated at 37° C. in a5% $CO_2$ environment for 24 h.

MIC Determination:

Examined the test plates after the correct incubation time and read the MIC endpoint at the concentration where a marked reduction occurred in the appearance of growth on the test plate as compared to that of growth on the positive control plates.

TABLE 1

Compound dilutions for MIC determination using the agar dilution method.

| Step | Stock (ug/ml) | Source | Volume from stock (uL) | Diluent, DMSO (uL)** | Intermediate Conc. (ug/mL) | Final Conc. At 1:100 (ug/mL) | Volume (uL) added to 10 mL agar |
|---|---|---|---|---|---|---|---|
| 1 | 1,600* | Stock | | | 1,600 | 16 | 100 |
| 2 | 1,600 | Stock | 75 | 75 | 800 | 8 | 100 |
| 3 | 1,600 | Stock | 75 | 225 | 400 | 4 | 100 |
| 4 | 1,600 | Stock | 75 | 525 | 200 | 2 | 100 |
| 5 | 200 | Step 4 | 75 | 75 | 100 | 1 | 100 |
| 6 | 200 | Step 4 | 75 | 225 | 50 | 0.5 | 100 |
| 7 | 200 | Step 4 | 75 | 525 | 25 | 0.25 | 100 |
| 8 | 25 | Step 7 | 75 | 75 | 12.5 | 0.125 | 100 |
| 9 | 25 | Step 7 | 75 | 225 | 6.25 | 0.06 | 100 |
| 10 | 25 | Step 7 | 75 | 525 | 3.1 | 0.03 | 100 |
| 11 | 3 | Step 10 | 75 | 75 | 1.6 | 0.016 | 100 |
| 12 | 3 | Step 10 | 75 | 225 | 0.8 | 0.008 | 100 |
| 13 | 3 | Step 10 | 75 | 525 | 0.4 | 0.004 | 100 |
| 14 | 0.4 | Step 13 | 75 | 75 | 0.2 | 0.002 | 100 |

*1,600 ug/ml = 64 ul (10 mg/ml stock) + 336 ul DMSO; 400 ul total volume to start
**compound dissolved and diluted in 100% DMSO Protocol 4. MIC Determination Procedure for *Mycobacterium* species Materials Round bottom 96-well microtiter plates (Costar 3788) or similar Film plate seals (PerkinElmer, TopSeal-A #6005250 or similar)

Middlebrook 7H10 broth with 0.2% glycerol
Middlebrook 7H10 agar with 0.2% glycerol
Middlebrook OADC Enrichment Inoculum Preparation for *M. tuberculosis*:
1. Used prepared frozen *M. tuberculosis* stock stored at −70° C. *M. tuberculosis* was grown in 7H10 broth+10% OADC, then frozen at a concentration of 100 Klett or $5 \times 10^7$ cfu/ml,
2. Prepared a 1:20 dilution by removal of 1 ml of the frozen stock and added it to 19 ml of 7H10 broth+10% OADC (final concentration $2.5 \times 10^6$ cfu/ml).
3. From this dilution prepared a second 1:20 dilution, removed 1 ml and added it to 19 ml of fresh broth. This was the final inoculum to add to the 96-well plates.

Inoculum Preparation for *M. kansasii*, *M. avium*, *M. abscessus* and *Nocardia* spc.:
1. Used prepared frozen stock of culture or a fresh culture grown in 7H10 broth at a concentration of 10 Klett or $5 \times 10^7$/ml.
2. Prepared a 1:20 dilution by removing 1.0 ml of the culture stock and added it to 19 ml of 7H10 broth (final concentration $2.5 \times 10^6$ cfu/ml).

3. From this dilution prepared a 1:20 dilution, removed 1 ml and added it to 19 ml of fresh broth (final suspension).

Plate Preparation:
1. Labeled plates.
2. Added 50 µl of 7H10 broth+10% OADC to all wells being utilized for MIC determination using a multichannel electronic pipettor.
3. Prepared stock solutions of drugs (e.g. 1 mg/ml concentration) to be tested.
4. Thawed and diluted frozen stock solutions using 7H10 broth+10% OADC to obtain a working solution 4× the maximum concentration tested (e.g. final concentration 32 µg/ml, highest concentration tested was 8 µg/ml). Dilutions were made from the stock solution. To start at a concentration of 1 µg/ml, the drugs were prepared at 4 µg/ml, so the starting concentration was 1 µg/ml. Removed 25 µl of the 1 mg/ml stock and added to 6.2 ml of broth. All dilutions of drugs were done in broth.
5. Added 50 µl of the 4× working solution to the first well of the designated row. Continued for all compounds to be tested. Using a multichannel electronic pipettor, mixed 4× and serial diluted compounds through the 11th well. Discarded remaining 50 µl. Used the 12th well as the positive control.
6. Incubated plates at 37° C. *M. tuberculosis* for ~18 days; *M. avium* and *M. kansasii* for ~7 days; *Nocardia* and *M. abcessus* for ~4 days; with film seals.
7. Read visually and recorded the results. The MIC was recorded as the lowest concentration of drug where no growth was observed (optical clarity in the well).

Protocol 5. Protocol for *Mycobacterium tuberculosis* Serum Shift MIC Assay

Materials and Reagents:
Costar #3904 Black-sided, flat-bottom 96-well microtiter plates
Middlebrook 7H9 broth (BD271310) with 0.2% glycerol
Middlebrook OADC Enrichment
Fetal Bovine Serum
Catalase (Sigma C1345)
Dextrose
$NaCl_2$
BBL Prompt Inoculation System (Fisher b26306)
Agar plates (Middlebrook 7H11 with 0.2% glycerol and OADC enrichment) with bacteria streaked to single colonies
Sterile DMSO Media prep:
1. For serum shifted MICs, three different media were required which all had a base of 7H9+0.2% glycerol. It was important that all media and supplements were sterilized prior to MICs.
2. Prepared all media below and inoculated as described in next section. Tested all compounds against Mtb using each media.
   a. 7H9+0.2% glycerol+10% OADC ("standard" MIC media).
   b. 7H9+0.2% glycerol+2 g/L dextrose+0.85 g/L NaCl+ 0.003 g/L catalase (0% FBS).
   c. 2×7H9+0.2% glycerol+2 g/L dextrose+0.85 g/L NaCl+0.003 g/L catalase combined with equal volume Fetal Bovine Serum (50% FBS).

Inoculum Prep:
1. Using BBL Prompt, picked 5-10 well-separated colonies and inoculated 1 ml sterile saline that came in the kit. Typically plates were two to three weeks of age when used for this assay due to the slow growth of this organism in culture.
2. Vortexed well, then sonicated in water bath for 30 sec providing a suspension of ~$10^8$ cells/ml. Actual density could be confirmed by plating out dilutions of this suspension.
3. Prepared inoculum in each of the three media formulations by diluting the BBL Prompt suspension 1/200 (for example: transferred 0.2 ml of cells to 40 ml of medium) to obtain a starting cell density of ~$10^6$ cells/ml.

4. Used 100 µl cells (~$5 \times 10^4$ cells) to inoculate each microtiter well containing 1 µl of drug in DMSO (see below).

Drug Dilutions, Inoculation, MIC Determination:
1. Control drug stocks Isoniazid and Novobiocin were prepared at 10 mM in 100% DMSO while Ciprofloxacin and Rifampin were prepared at 1 mM in 50% DMSO and 100% DMSO, respectively. Prepared dilutions-dispensed 100 µL of the stock solution into the first column of a 96-well plate. Prepared 11-step, 2-fold serial dilutions across the row for each compound by transferring 50 µl from column 1 into 50 µl of DMSO in column 2. Continued to transfer 50 µL from column 2 through column 11 while mixing and changing tips at each column. Left column 12 with DMSO only as a control.
2. Transferred 1 µl of each dilution into an empty microtiter well prior to the addition of 100 µl of cells. The starting concentration of Isoniazid and Novobiocin was 100 µM after the dilution into medium+cells; the starting concentration of Ciprofloxacin and Rifampin was 10 µM after the dilution into medium+cells. Compound concentrations decreased in 2× steps moving across the rows of the microtiter plate. All MICs were done in duplicate at each of the three medium conditions.
3. Test sets of compounds were typically at 10 mM and 50 µL, volume.
4. Used a multichannel pipettor, removed all of the volume from each column of the master plate and transferred into the first column of a new 96-well microtiter plate. Repeated for each column of compounds on master plate, transferring into column 1 of a new 96-well plate.
5. As described above for control compounds, generated 2-fold, 11-point dilutions of each compound using DMSO as diluent. In all cases, left column 12 as DMSO only for a control. Once all dilutions were complete, again transferred 1 µl of each dilution into an empty microtiter well prior to the addition of 100 µl of cells as done for the control compounds.
6. All wells were inoculated with 100 µl of diluted cell suspension (see above).
7. After inoculum addition, mixed plates by gently tapping sides of plate.
8. Plates were incubated in a humidified 37° C. chamber for 9 days.
9. At 9 days added 25 µl 0.01% sterile resazurin to each well. Measured background fluorescence at Excitation 492 nm, Emission 595 nm and returned the plate to the incubator for another 24 hours.

After 24 hours the fluorescence of each well was measured at Excitation 492 nm, Emission 595 nm.

Percent inhibition by a given compound was calculated as follows: Percent inhibition=100−([well fluorescence−average background fluorescence]/[DMSO control−average background fluorescence]×100). MICs were scored for all three medium conditions as the lowest compound concentration that inhibited resazurin reduction ('%-inhibition') signal ≥70% at a given medium condition.

Table 2 shows the results of the MIC assay for selected compounds of this invention.

In Table 2 and in subsequent Tables and Examples, "Compound 12" corresponds to 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea and "Compound 13" relates to the mesylate salt of Compound 12. Similarly, "Compound 23" corresponds to 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea and "Compound 23A" relates to the mesylate salt of Compound 23. These are the same numbers used to identify said compounds and salts as used in the Examples above.

TABLE 2

MIC Values of Selected Compounds

| Strain/Special Condition | Protocol | MIC (µg/ml) Compound 13 | MIC (µg/ml) Compound 23A |
|---|---|---|---|
| *Staphylococcus aureus* ATCC 29213 | 1 | 0.13 | 0.021 |
| *Staphylococcus aureus* ATCC 29213 with Human Serum | 1 | 0.31 | 0.15 |
| *Staphylococcus aureus* ATCC 29213 with Rat Serum | 1 | 0.53 | 0.18 |
| *Staphylococcus aureus* ATCC 29213 with Mouse Serum | 1 | 2 | 0.5 |
| *Staphylococcus aureus* ATCC 29213 GyrB T173I | 1 | 1.29 | 0.3 |
| *Enterococcus faecalis* ATCC 29212, with Laked Horse Blood | 1 | 0.081 | 0.028 |
| *Enterococcus faecium* ATCC 49624 with Laked Horse Blood | 1 | 0.39 | 0.11 |
| *Enterococcus faecium* ATCC 49624 | 1 | 0.25 | 0.11 |
| *Streptococcus pneumoniae* ATCC 10015, with Laked Horse Blood | 1 | 0.022 | 0.01 |
| *Bacillus cereus* ATCC 10987 | 1 | 0.5 | 0.031 |
| *Bacillus cereus* ATCC 14579 | 1 | 0.5 | 0.031 |
| *Bacillus subtilis* ATCC 6638 | 1 | >8 | 2 |
| *Bacillus subtilis* (168) ATCC 6051 | 1 | >8 | 4 |
| *Clostridium difficile* ATCC BAA-1382 | 3 | 1 | 0.38 |
| *Haemophilus influenzae* ATCC 49247 | 2 | 1 | 0.5 |
| *Haemophilus influenzae* (Rd1 KW20) ATCC 51907 | 2 | 2.5 | 1.3 |
| *Haemophilus influenzae* Rd0894 (AcrA-) | 2 | 0.14 | 0.041 |
| *Moraxella catarrhalis* ATCC 25238 | 2 | 0.071 | ≤0.016 |
| *Moraxella catarrhalis* ATCC 49143 | 2 | 0.04 | ≤0.016 |
| *Neisseria gonorrhoeae* ATCC 35541 | 3 | 1.3 | 0.42 |
| *Neisseria gonorrhoeae* ATCC 49226 | 3 | 2.3 | 1 |
| *Escherichia coli* AG100 WT | 2 | >16 | 4 |
| *Escherichia coli* AG100 tolC | 2 | 0.11 | 0.063 |
| *Escherichia coli* ATCC 25922 | 2 | 16 | 12 |
| *Escherichia coli* CHE30 | 2 | >16 | 8 |
| *Escherichia coli* CHE30 tolC | 2 | 0.5 | 0.125 |
| *Escherichia coli* MC4100 | 2 | >16 | >16 |
| *Escherichia coli* MC4100 tolC | 2 | 1 | 0.25 |
| *Klebsiella pneumoniae* ATCC 700603 | 2 | >16 | 16 |
| *Klebsiella pneumoniae* ATCC BAA-1705 | 2 | >16 | 12 |
| *Acinetobacter baumannii* ATCC 19606 | 2 | >16 | 8 |

TABLE 2-continued

MIC Values of Selected Compounds

| Strain/Special Condition | Protocol | MIC (µg/ml) Compound 13 | MIC (µg/ml) Compound 23A |
|---|---|---|---|
| *Acinetobacter baumannii* ATCC BAA-1710 | 2 | >16 | 6 |
| *Pseudomonas aeruginosa* PAO1 | 2 | >16 | >16 |
| *Pseudomonas aeruginosa* PAO750 | 2 | 0.33 | 0.25 |
| *Stenotrophomonas maltophilia* ATCC BAA-84 | 2 | Not done | >8 |
| *Stenotrophomonas maltophilia* ATCC13637 | 2 | Not done | >8 |
| *Mycobacterium avium* 103 | 4 | 0.47 | 0.18 |
| *M. avium* Far | 4 | 0.94 | 0.23 |
| *M. avium* 3404.4 | 4 | 0.94 | 0.23 |
| *Nocardia caviae* 2497 | 4 | 2 | 0.125 |
| *N. asteroids* 2039 | 4 | 8 | 1 |
| *N. nova* 10 | 4 | 8 | 1 |
| *M. kansasii* 303 | 4 | Not Done | 0.03 |
| *M. kansasii* 316 | 4 | Not Done | 0.06 |
| *M. kansasii* 379 | 4 | Not Done | <0.015 |
| *M. tuberculosis* H37Rv ATCC 25618 | 4 | 0.37 | 0.015 |
| *M. tuberculosis* Erdman ATCC 35801 | 4 | 0.25 | 0.06 |
| *M. tuberculosis* Erdman ATCC 35801 | 5 | 0.045 | 0.03 |
| *M. tuberculosis* Erdman ATCC 35801 with Mouse Serum | 5 | 2 | 0.5 |
| *M. abscessus* BB2 | 4 | Not Done | 1 |
| *M. abscessus* MC 6005 | 4 | Not Done | 1 |
| *M. abscessus* MC 5931 | 4 | Not Done | 0.5 |
| *M. abscessus* MC 5605 | 4 | Not Done | 1.5 |
| *M. abscessus* MC 6025 | 4 | Not Done | 0.75 |
| *M. abscessus* MC 5908 | 4 | Not Done | 1.5 |
| *M. abscessus* BB3 | 4 | Not Done | 0.5 |
| *M. abscessus* BB4 | 4 | Not Done | 2 |
| *M. abscessus* BB5 | 4 | Not Done | 0.5 |
| *M. abscessus* MC 5922 | 4 | Not Done | 0.25 |
| *M. abscessus* MC 5960 | 4 | Not Done | 0.5 |
| *M. abscessus* BB1 | 4 | Not Done | 2 |
| *M. abscessus* MC 5812 | 4 | Not Done | 1 |
| *M. abscessus* MC 5901 | 4 | Not Done | 1 |
| *M. abscessus* BB6 | 4 | Not Done | 0.5 |
| *M. abscessus* BB8 | 4 | Not Done | 0.5 |
| *M. abscessus* MC 5908 | 4 | Not Done | 1 |
| *M. abscessus* LT 949 | 4 | Not Done | 1 |
| *M. abscessus* BB10 | 4 | Not Done | 0.015 |
| *M. abscessus* MC 6142 | 4 | Not Done | 0.5 |
| *M. abscessus* MC 6136 | 4 | Not Done | 0.5 |
| *M. abscessus* MC 6111 | 4 | Not Done | 0.5 |
| *M. abscessus* MC 6153 | 4 | Not Done | 1 |

Table 3 shows the results of the MIC90 assay for selected compounds of this invention.

TABLE 3

MIC90 Values of Selected Compounds with Panels of Gram
Positive, Gram Negative and Anaerobic Pathogens

| Organism | Number of Isolates Tested | Protocol | Compound 13 Range (µg/ml) | Compound 13 MIC90 (µg/ml) | Compound 23A Range (µg/ml) | Compound 23A MIC90 (µg/ml) |
|---|---|---|---|---|---|---|
| Aerobic Gram-positive | | | | | | |
| Staphylococcus aureus | 67 | 1 | 0.03-0.5 | 0.25 | 0.008-0.06 | 0.03 |
| Staphlococcus epidermidis | 35 | 1 | 0.03-0.25 | 0.12 | 0.008-0.03 | 0.03 |
| Enterococcus faecalis | 34 | 1 | 0.03-0.25 | 0.25 | 0.015-0.12 | 0.06 |
| Enterococcus faecium | 33 | 1 | 0.12-0.5 | 0.5 | 0.003-0.25 | 0.12 |
| Streptococcus pneumoniae | 67 | 1 | 0.015-0.06 | 0.06 | 0.008-0.03 | 0.015 |
| β-haemolytic streptococci (Groups A, B, C and G) | 28 | 1 | 0.06-0.5 | 0.25 | 0.015-0.12 | 0.12 |
| Aerobic Gram-negative | | | | | | |
| Haemophilus influenzae | 55 | 2 | 0.25-8 | 2 | 0.06-2 | 1 |
| Moraxella catarrhalis | 26 | 2 | 0.015-0.12 | 0.12 | ≤0.004-0.03 | 0.03 |
| Acinetobacter baumannii | 12 | 2 | >8->8 | >8 | 4->8 | >8 |
| Pseudomonas aeruginosa | 12 | 2 | >8->8 | >8 | >8->8 | >8 |
| Escherichia coli | 12 | 2 | >8->8 | >8 | 2->8 | >8 |
| Klebsiella pneumoniae | 12 | 2 | >8->8 | >8 | 2->8 | >8 |
| Proteus mirabilis | 12 | 2 | >8->8 | >8 | 4->8 | >8 |
| Enterobacter cloacae | 12 | 2 | >8->8 | >8 | >8->8 | >8 |
| Neisseria gonorrhoeae | 13 | 3 | 0.5-1 | 1 | 0.12-0.25 | 0.25 |
| Neisseria meningitidis | 12 | 3 | 0.015-0.25 | 0.12 | 0.008-0.06 | 0.03 |
| Anaerobes | | | | | | |
| Bacteroides and Parabacter spp. | 26 | 3 | 2->16 | >16 | 0.12-16 | 16 |
| Bacteroides fragilis | 25 | 3 | 8->16 | >16 | 1-16 | 16 |
| Clostridium difficile | 16 | 3 | 0.5-16 | 1 | 0.06-4 | 0.25 |
| Clostridium perfringens | 12 | 3 | 0.12-0.5 | 0.5 | 0.12-0.5 | 0.5 |
| Fusobacterium spp. | 16 | 3 | 1-4 | 2 | 0.015->16 | >16 |
| Peptostreptococcus spp. | 11 | 3 | 0.06->16 | >16 | 0.03->16 | >16 |
| Prevotella spp. | 13 | 3 | 0.5->16 | >16 | 0.06-16 | 16 |

Table 3A also shows the results of the MIC assays for selected compounds of this invention. In Table 3A, "Compound 23A" corresponds to the methanesulfonic acid salt of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23A). Similarly, "Compound W" corresponds to disodium (R)-2-(5-(2-(3-ethylureido)-6-fluoro-7-(tetrahydrofuran-2-yl)-1H-benzo[d]imidazol-5-yl)pyrimidin-2-yl) propan-2-yl phosphate (W). These are the same numbers used to identify said compounds in the synthetic Examples above.

TABLE 3A

MIC Values of Selected Compounds

| Strain/Special Condition | Strain Source | Protocol | Compound 23A MIC (µg/ml) | Compound W MIC (µg/ml) |
|---|---|---|---|---|
| Staphylococcus aureus ATCC 29213 | ATCC[1] | 1 | 0.021 | 8 |
| Staphylococcus aureus ATCC 29213 with Human Serum | ATCC | 1 | 0.15 | 8 |
| Staphylococcus aureus ATCC 29213 with Rat Serum | ATCC | 1 | 0.18 | 8 |
| Staphylococcus aureus ATCC 29213 with Mouse Serum | ATCC | 1 | 0.5 | 8 |
| Staphylococcus aureus ATCC 29213 GyrB T173I | Vertex[2] | 1 | 0.3 | >8 |

TABLE 3A-continued

MIC Values of Selected Compounds

| Strain/Special Condition | Strain Source | Protocol | Compound 23A MIC (µg/ml) | Compound W MIC (µg/ml) |
|---|---|---|---|---|
| *Enterococcus faecalis* ATCC 29212, with Laked Horse Blood | ATCC | 1 | 0.028 | 1 |
| *Enterococcus faecium* ATCC 49624 with Laked Horse Blood | ATCC | 1 | 0.11 | 2 |
| *Streptococcus pneumoniae* ATCC 10015, with Laked Horse Blood | ATCC | 1 | 0.01 | 0.25 |
| *Haemophilus influenzae* (Rd1 KW20) ATCC 51907 | ATCC | 2 | 1.3 | 8 |
| *Haemophilus influenzae* Rd0894 (AcrA-) | Hiroshi Nikaido | 2 | 0.041 | 0.25 |
| *Escherichia coli* AG100 WT | CGSC[3] | 2 | 4 | >16 |
| *Escherichia coli* AG100 tolC[4] | Vertex | 2 | 0.063 | 8 |

[1] American Type Culture Collection
[2] Constructed by Vertex
[3] *Coli* Genetic Stock Center
[4] all tolC constructs are tolC::Tn10 derived from CAG12184 (*Coli* Genetic Stock Center)

In Table 4 below, the term "CMI" stands for The Clinical Microbiology Institute located in Wilsonville, Oreg.

TABLE 4

Panels of Anaerobic Organism Used to Generate MIC90 Data

| CMI# | ORGANISM |
|---|---|
| A2380 | *B. fragilis* |
| A2381 | *B. fragilis* |
| A2382 | *B. fragilis* |
| A2486 | *B. fragilis* |
| A2487 | *B. fragilis* |
| A2489 | *B. fragilis* |
| A2527 | *B. fragilis* |
| A2529 | *B. fragilis* |
| A2562 | *B. fragilis* |
| A2627 | *B. fragilis* |
| A2802 | *B. fragilis* |
| A2803 | *B. fragilis* |
| A2804 | *B. fragilis* |
| A2805 | *B. fragilis* |
| A2806 | *B. fragilis* |
| A2807 | *B. fragilis* |
| A2808 | *B. fragilis* |
| A2809 | *B. fragilis* |
| A2810 | *B. fragilis* |
| A2811 | *B. fragilis* |
| A2812 | *B. fragilis* |
| A2813 | *B. fragilis* |
| A2814 | *B. fragilis* |
| A2460 | *B. thetaiotaomicron* |
| A2462 | *B. thetaiotaomicron* |
| A2463 | *B. thetaiotaomicron* |
| A2464 | *B. thetaiotaomicron* |
| A2536 | *B. thetaiotaomicron* |
| A2591 | *B. uniformis* |
| A2604 | *B. vulgatus* |
| A2606 | *B. vulgatus* |
| A2613 | *B. ovatus* |
| A2616 | *B. ovatus* |
| A2815 | *Bacteroides tectum* |
| A2816 | *B. ureolyticus* |
| A2817 | *Bacteroides capillosus* |
| A2818 | *B. ureolyticus* |
| A2824 | *Parabacter distasonis* |
| A2825 | *B. ovatus* |
| A2826 | *B. uniformis* |
| A2827 | *B. uniformis* |
| A2828 | *B. vulgatus* |
| A2829 | *B. vulgatus* |
| A2830 | *B. ovatus* |
| A2831 | *B. thetaiotaomicron* |
| A2832 | *Parabacter distasonis* |
| A2833 | *B. thetaiotaomicron* |
| A2767 | *C. difficile* |
| A2768 | *C. difficile* |
| A2769 | *C. difficile* |
| A2770 | *C. difficile* |
| A2771 | *C. difficile* |
| A2772 | *C. difficile* |
| A2773 | *C. difficile* |
| A2774 | *C. difficile* |
| A2775 | *C. difficile* |
| A2776 | *C. difficile* |
| A2777 | *C. difficile* |
| A2778 | *C. difficile* |
| A2779 | *C. difficile* |
| A2780 | *C. difficile* |
| A2140 | *C. perfringens* |
| A2203 | *C. perfringens* |
| A2204 | *C. perfringens* |
| A2227 | *C. perfringens* |
| A2228 | *C. perfringens* |
| A2229 | *C. perfringens* |
| A2315 | *C. perfringens* |
| A2332 | *C. perfringens* |
| A2333 | *C. perfringens* |
| A2334 | *C. perfringens* |
| A2389 | *C. perfringens* |
| A2390 | *C. perfringens* |
| A864 | *F. necrophorum* |
| A871 | *F. nucleatum* |
| A1667 | *F. necrophorum* |
| A1666 | *F. necrophorum* |
| A2249 | *F. nucleatum* |
| A2716 | *Fusobacterium* species |
| A2717 | *Fusobacterium* species |
| A2719 | *Fusobacterium* species |
| A2721 | *Fusobacterium* species |
| A2722 | *Fusobacterium* species |
| A2710 | *Fusobacterium* species |
| A2711 | *Fusobacterium* species |
| A2712 | *Fusobacterium* species |
| A2713 | *Fusobacterium* species |
| A2714 | *Fusobacterium* species |
| A2715 | *Fusobacterium* species |
| A1594 | *Peptostreptococcus anaerobius* |
| A2158 | *Peptostreptococcus magnus* |
| A2168 | *Peptostreptococcus anaerobius* |
| A2170 | *Peptostreptococcus magnus* |
| A2171 | *Peptostreptococcus magnus* |
| A2575 | *Peptostreptococcus* spp. |
| A2579 | *Peptostreptococcus asaccharolyticus* |
| A2580 | *Peptostreptococcus asaccharolyticus* |
| A2614 | *Peptostreptococcus asaccharolyticus* |
| A2620 | *Peptostreptococcus asaccharolyticus* |
| A2629 | *Peptostreptococcus* spp. |
| A2739 | *Prevotella denticola* |
| A2752 | *Prevotella bivia* |
| A2753 | *Prevotella intermedia* |
| A2754 | *Prevotella intermedia* |
| A2756 | *Prevotella bivia* |
| A2759 | *Prevotella bivia* |
| A2760 | *Prevotella denticola* |
| A2761 | *Prevotella intermedia* |
| A2762 | *Prevotella melaninogenica* |
| A2765 | *Prevotella melaninogenica* |
| A2766 | *Prevotella melaninogenica* |
| A2821 | *Prevotella bivia* |
| A2822 | *Prevotella bivia* |
| QCBF | *B. fragilis* |
| QCBT | *B. thetaiotaomicron* |

TABLE 4-continued

Panels of Anaerobic Organism Used to GenerateMIC90 Data

| CMI# | ORGANISM |
|---|---|
| QCCD | C. difficile |
| QCBF | B. fragilis |
| QCBT | B. thetaiotaomicron |
| QCCD | C. difficile |

In Table 5 below, the term "JMI" stands for The Jones Microbiology Institute located in North Liberty, Iowa.

TABLE 5

Panels of Gram Positive and Gram Negative Organism Used to GenerateMIC90 Data

| JMI Isolate # | JMI Organism Code | Organism |
|---|---|---|
| 394 | ACB | Acinetobacter baumannii |
| 2166 | ACB | Acinetobacter baumannii |
| 3060 | ACB | Acinetobacter baumannii |
| 3170 | ACB | Acinetobacter baumannii |
| 9328 | ACB | Acinetobacter baumannii |
| 9922 | ACB | Acinetobacter baumannii |
| 13618 | ACB | Acinetobacter baumannii |
| 14308 | ACB | Acinetobacter baumannii |
| 17086 | ACB | Acinetobacter baumannii |
| 17176 | ACB | Acinetobacter baumannii |
| 30554 | ACB | Acinetobacter baumannii |
| 32007 | ACB | Acinetobacter baumannii |
| 1192 | ECL | Enterobacter cloacae |
| 3096 | ECL | Enterobacter cloacae |
| 5534 | ECL | Enterobacter cloacae |
| 6487 | ECL | Enterobacter cloacae |
| 9592 | ECL | Enterobacter cloacae |
| 11680 | ECL | Enterobacter cloacae |
| 12573 | ECL | Enterobacter cloacae |
| 12735 | ECL | Enterobacter cloacae |
| 13057 | ECL | Enterobacter cloacae |
| 18048 | ECL | Enterobacter cloacae |
| 25173 | ECL | Enterobacter cloacae |
| 29443 | ECL | Enterobacter cloacae |
| 44 | EF | Enterococcus faecalis |
| 355 | EF | Enterococcus faecalis |
| 886 | EF | Enterococcus faecalis |
| 955 | EF | Enterococcus faecalis |
| 1000 | EF | Enterococcus faecalis |
| 1053 | EF | Enterococcus faecalis |
| 1142 | EF | Enterococcus faecalis |
| 1325 | EF | Enterococcus faecalis |
| 1446 | EF | Enterococcus faecalis |
| 2014 | EF | Enterococcus faecalis |
| 2103 | EF | Enterococcus faecalis |
| 2255 | EF | Enterococcus faecalis |
| 2978 | EF | Enterococcus faecalis |
| 2986 | EF | Enterococcus faecalis |
| 5027 | EF | Enterococcus faecalis |
| 5270 | EF | Enterococcus faecalis |
| 5874 | EF | Enterococcus faecalis |
| 7430 | EF | Enterococcus faecalis |
| 7904 | EF | Enterococcus faecalis |
| 8092 | EF | Enterococcus faecalis |
| 8691 | EF | Enterococcus faecalis |
| 9090 | EF | Enterococcus faecalis |
| 10795 | EF | Enterococcus faecalis |
| 14104 | EF | Enterococcus faecalis |
| 16481 | EF | Enterococcus faecalis |
| 18217 | EF | Enterococcus faecalis |
| 22442 | EF | Enterococcus faecalis |
| 25726 | EF | Enterococcus faecalis |
| 26143 | EF | Enterococcus faecalis |
| 28131 | EF | Enterococcus faecalis |
| 29765 | EF | Enterococcus faecalis |
| 30279 | EF | Enterococcus faecalis |
| 31234 | EF | Enterococcus faecalis |
| 31673 | EF | Enterococcus faecalis |

TABLE 5-continued

Panels of Gram Positive and Gram Negative Organism Used to GenerateMIC90 Data

| JMI Isolate # | JMI Organism Code | Organism |
|---|---|---|
| 115 | EFM | Enterococcus faecium |
| 227 | EFM | Enterococcus faecium |
| 414 | EFM | Enterococcus faecium |
| 712 | EFM | Enterococcus faecium |
| 870 | EFM | Enterococcus faecium |
| 911 | EFM | Enterococcus faecium |
| 2356 | EFM | Enterococcus faecium |
| 2364 | EFM | Enterococcus faecium |
| 2762 | EFM | Enterococcus faecium |
| 3062 | EFM | Enterococcus faecium |
| 4464 | EFM | Enterococcus faecium |
| 4473 | EFM | Enterococcus faecium |
| 4653 | EFM | Enterococcus faecium |
| 4679 | EFM | Enterococcus faecium |
| 6803 | EFM | Enterococcus faecium |
| 6836 | EFM | Enterococcus faecium |
| 8280 | EFM | Enterococcus faecium |
| 8702 | EFM | Enterococcus faecium |
| 9855 | EFM | Enterococcus faecium |
| 10766 | EFM | Enterococcus faecium |
| 12799 | EFM | Enterococcus faecium |
| 13556 | EFM | Enterococcus faecium |
| 13783 | EFM | Enterococcus faecium |
| 14687 | EFM | Enterococcus faecium |
| 15268 | EFM | Enterococcus faecium |
| 15525 | EFM | Enterococcus faecium |
| 15538 | EFM | Enterococcus faecium |
| 18102 | EFM | Enterococcus faecium |
| 18306 | EFM | Enterococcus faecium |
| 19967 | EFM | Enterococcus faecium |
| 22428 | EFM | Enterococcus faecium |
| 23482 | EFM | Enterococcus faecium |
| 29658 | EFM | Enterococcus faecium |
| 597 | EC | Escherichia coli |
| 847 | EC | Escherichia coli |
| 1451 | EC | Escherichia coli |
| 8682 | EC | Escherichia coli |
| 11199 | EC | Escherichia coli |
| 12583 | EC | Escherichia coli |
| 12792 | EC | Escherichia coli |
| 13265 | EC | Escherichia coli |
| 14594 | EC | Escherichia coli |
| 22148 | EC | Escherichia coli |
| 29743 | EC | Escherichia coli |
| 30426 | EC | Escherichia coli |
| 470 | BSA | Group A Streptococcus |
| 2965 | BSA | Group A Streptococcus |
| 3112 | BSA | Group A Streptococcus |
| 3637 | BSA | Group A Streptococcus |
| 4393 | BSA | Group A Streptococcus |
| 4546 | BSA | Group A Streptococcus |
| 4615 | BSA | Group A Streptococcus |
| 5848 | BSA | Group A Streptococcus |
| 6194 | BSA | Group A Streptococcus |
| 8816 | BSA | Group A Streptococcus |
| 11814 | BSA | Group A Streptococcus |
| 16977 | BSA | Group A Streptococcus |
| 18083 | BSA | Group A Streptococcus |
| 18821 | BSA | Group A Streptococcus |
| 25178 | BSA | Group A Streptococcus |
| 30704 | BSA | Group A Streptococcus |
| 12 | BSB | Group B Streptococcus |
| 10366 | BSB | Group B Streptococcus |
| 10611 | BSB | Group B Streptococcus |
| 16786 | BSB | Group B Streptococcus |
| 18833 | BSB | Group B Streptococcus |
| 30225 | BSB | Group B Streptococcus |
| 10422 | BSC | Group C Streptococcus |
| 14209 | BSC | Group C Streptococcus |
| 29732 | BSC | Group C Streptococcus |
| 8544 | BSG | Group G Streptococcus |
| 18086 | BSG | Group G Streptococcus |
| 29815 | BSG | Group G Streptococcus |
| 147 | HI | Haemophilus influenzae |

TABLE 5-continued

Panels of Gram Positive and Gram Negative Organism Used to GenerateMIC90 Data

| JMI Isolate # | JMI Organism Code | Organism |
|---|---|---|
| 180 | HI | *Haemophilus influenzae* |
| 934 | HI | *Haemophilus influenzae* |
| 970 | HI | *Haemophilus influenzae* |
| 1298 | HI | *Haemophilus influenzae* |
| 1819 | HI | *Haemophilus influenzae* |
| 1915 | HI | *Haemophilus influenzae* |
| 2000 | HI | *Haemophilus influenzae* |
| 2562 | HI | *Haemophilus influenzae* |
| 2821 | HI | *Haemophilus influenzae* |
| 3133 | HI | *Haemophilus influenzae* |
| 3140 | HI | *Haemophilus influenzae* |
| 3497 | HI | *Haemophilus influenzae* |
| 3508 | HI | *Haemophilus influenzae* |
| 3535 | HI | *Haemophilus influenzae* |
| 4082 | HI | *Haemophilus influenzae* |
| 4108 | HI | *Haemophilus influenzae* |
| 4422 | HI | *Haemophilus influenzae* |
| 4868 | HI | *Haemophilus influenzae* |
| 4872 | HI | *Haemophilus influenzae* |
| 5858 | HI | *Haemophilus influenzae* |
| 6258 | HI | *Haemophilus influenzae* |
| 6875 | HI | *Haemophilus influenzae* |
| 7063 | HI | *Haemophilus influenzae* |
| 7600 | HI | *Haemophilus influenzae* |
| 8465 | HI | *Haemophilus influenzae* |
| 10280 | HI | *Haemophilus influenzae* |
| 10732 | HI | *Haemophilus influenzae* |
| 10850 | HI | *Haemophilus influenzae* |
| 11366 | HI | *Haemophilus influenzae* |
| 11716 | HI | *Haemophilus influenzae* |
| 11724 | HI | *Haemophilus influenzae* |
| 11908 | HI | *Haemophilus influenzae* |
| 12093 | HI | *Haemophilus influenzae* |
| 12107 | HI | *Haemophilus influenzae* |
| 13424 | HI | *Haemophilus influenzae* |
| 13439 | HI | *Haemophilus influenzae* |
| 13672 | HI | *Haemophilus influenzae* |
| 13687 | HI | *Haemophilus influenzae* |
| 13792 | HI | *Haemophilus influenzae* |
| 13793 | HI | *Haemophilus influenzae* |
| 14440 | HI | *Haemophilus influenzae* |
| 15351 | HI | *Haemophilus influenzae* |
| 15356 | HI | *Haemophilus influenzae* |
| 15678 | HI | *Haemophilus influenzae* |
| 15800 | HI | *Haemophilus influenzae* |
| 17841 | HI | *Haemophilus influenzae* |
| 18614 | HI | *Haemophilus influenzae* |
| 25195 | HI | *Haemophilus influenzae* |
| 27021 | HI | *Haemophilus influenzae* |
| 28326 | HI | *Haemophilus influenzae* |
| 28332 | HI | *Haemophilus influenzae* |
| 29918 | HI | *Haemophilus influenzae* |
| 29923 | HI | *Haemophilus influenzae* |
| 31911 | HI | *Haemophilus influenzae* |
| 428 | KPN | *Klebsiella pneumoniae* |
| 791 | KPN | *Klebsiella pneumoniae* |
| 836 | KPN | *Klebsiella pneumoniae* |
| 1422 | KPN | *Klebsiella pneumoniae* |
| 1674 | KPN | *Klebsiella pneumoniae* |
| 1883 | KPN | *Klebsiella pneumoniae* |
| 6486 | KPN | *Klebsiella pneumoniae* |
| 8789 | KPN | *Klebsiella pneumoniae* |
| 10705 | KPN | *Klebsiella pneumoniae* |
| 11123 | KPN | *Klebsiella pneumoniae* |
| 28148 | KPN | *Klebsiella pneumoniae* |
| 29432 | KPN | *Klebsiella pneumoniae* |
| 937 | MCAT | *Moraxella catarrhalis* |
| 1290 | MCAT | *Moraxella catarrhalis* |
| 1830 | MCAT | *Moraxella catarrhalis* |
| 1903 | MCAT | *Moraxella catarrhalis* |
| 4346 | MCAT | *Moraxella catarrhalis* |
| 4880 | MCAT | *Moraxella catarrhalis* |
| 6241 | MCAT | *Moraxella catarrhalis* |
| 6551 | MCAT | *Moraxella catarrhalis* |
| 7074 | MCAT | *Moraxella catarrhalis* |
| 7259 | MCAT | *Moraxella catarrhalis* |
| 7544 | MCAT | *Moraxella catarrhalis* |
| 8142 | MCAT | *Moraxella catarrhalis* |
| 8451 | MCAT | *Moraxella catarrhalis* |
| 9246 | MCAT | *Moraxella catarrhalis* |
| 9996 | MCAT | *Moraxella catarrhalis* |
| 12158 | MCAT | *Moraxella catarrhalis* |
| 13443 | MCAT | *Moraxella catarrhalis* |
| 13692 | MCAT | *Moraxella catarrhalis* |
| 13817 | MCAT | *Moraxella catarrhalis* |
| 14431 | MCAT | *Moraxella catarrhalis* |
| 14762 | MCAT | *Moraxella catarrhalis* |
| 14842 | MCAT | *Moraxella catarrhalis* |
| 15361 | MCAT | *Moraxella catarrhalis* |
| 15741 | MCAT | *Moraxella catarrhalis* |
| 17843 | MCAT | *Moraxella catarrhalis* |
| 18639 | MCAT | *Moraxella catarrhalis* |
| 241 | GC | *Neisseria gonorrhoeae* |
| 291 | GC | *Neisseria gonorrhoeae* |
| 293 | GC | *Neisseria gonorrhoeae* |
| 344 | GC | *Neisseria gonorrhoeae* |
| 451 | GC | *Neisseria gonorrhoeae* |
| 474 | GC | *Neisseria gonorrhoeae* |
| 491 | GC | *Neisseria gonorrhoeae* |
| 493 | GC | *Neisseria gonorrhoeae* |
| 503 | GC | *Neisseria gonorrhoeae* |
| 521 | GC | *Neisseria gonorrhoeae* |
| 552 | GC | *Neisseria gonorrhoeae* |
| 573 | GC | *Neisseria gonorrhoeae* |
| 592 | GC | *Neisseria gonorrhoeae* |
| 25 | NM | *Neisseria meningitidis* |
| 813 | NM | *Neisseria meningitidis* |
| 1725 | NM | *Neisseria meningitidis* |
| 2747 | NM | *Neisseria meningitidis* |
| 3201 | NM | *Neisseria meningitidis* |
| 3335 | NM | *Neisseria meningitidis* |
| 7053 | NM | *Neisseria meningitidis* |
| 9407 | NM | *Neisseria meningitidis* |
| 10447 | NM | *Neisseria meningitidis* |
| 12685 | NM | *Neisseria meningitidis* |
| 12841 | NM | *Neisseria meningitidis* |
| 14038 | NM | *Neisseria meningitidis* |
| 1127 | PM | *Proteus mirabilis* |
| 3049 | PM | *Proteus mirabilis* |
| 4471 | PM | *Proteus mirabilis* |
| 8793 | PM | *Proteus mirabilis* |
| 10702 | PM | *Proteus mirabilis* |
| 11218 | PM | *Proteus mirabilis* |
| 14662 | PM | *Proteus mirabilis* |
| 17072 | PM | *Proteus mirabilis* |
| 19059 | PM | *Proteus mirabilis* |
| 23367 | PM | *Proteus mirabilis* |
| 29819 | PM | *Proteus mirabilis* |
| 31419 | PM | *Proteus mirabilis* |
| 1881 | PSA | *Pseudomonas aeruginosa* |
| 5061 | PSA | *Pseudomonas aeruginosa* |
| 7909 | PSA | *Pseudomonas aeruginosa* |
| 8713 | PSA | *Pseudomonas aeruginosa* |
| 14318 | PSA | *Pseudomonas aeruginosa* |
| 14772 | PSA | *Pseudomonas aeruginosa* |
| 15512 | PSA | *Pseudomonas aeruginosa* |
| 17093 | PSA | *Pseudomonas aeruginosa* |
| 17802 | PSA | *Pseudomonas aeruginosa* |
| 19661 | PSA | *Pseudomonas aeruginosa* |
| 29967 | PSA | *Pseudomonas aeruginosa* |
| 31539 | PSA | *Pseudomonas aeruginosa* |
| 82 | SA | *Staphylococcus aureus* |
| 99 | SA | *Staphylococcus aureus* |
| 138 | SA | *Staphylococcus aureus* |
| 139 | SA | *Staphylococcus aureus* |
| 140 | SA | *Staphylococcus aureus* |
| 141 | SA | *Staphylococcus aureus* |
| 142 | SA | *Staphylococcus aureus* |

TABLE 5-continued

Panels of Gram Positive and Gram Negative Organism Used to GenerateMIC90 Data

| JMI Isolate # | JMI Organism Code | Organism |
|---|---|---|
| 272 | SA | *Staphylococcus aureus* |
| 287 | SA | *Staphylococcus aureus* |
| 354 | SA | *Staphylococcus aureus* |
| 382 | SA | *Staphylococcus aureus* |
| 1112 | SA | *Staphylococcus aureus* |
| 1687 | SA | *Staphylococcus aureus* |
| 1848 | SA | *Staphylococcus aureus* |
| 2031 | SA | *Staphylococcus aureus* |
| 2159 | SA | *Staphylococcus aureus* |
| 2645 | SA | *Staphylococcus aureus* |
| 3256 | SA | *Staphylococcus aureus* |
| 3276 | SA | *Staphylococcus aureus* |
| 4044 | SA | *Staphylococcus aureus* |
| 4214 | SA | *Staphylococcus aureus* |
| 4217 | SA | *Staphylococcus aureus* |
| 4220 | SA | *Staphylococcus aureus* |
| 4231 | SA | *Staphylococcus aureus* |
| 4240 | SA | *Staphylococcus aureus* |
| 4262 | SA | *Staphylococcus aureus* |
| 4370 | SA | *Staphylococcus aureus* |
| 4665 | SA | *Staphylococcus aureus* |
| 4666 | SA | *Staphylococcus aureus* |
| 4667 | SA | *Staphylococcus aureus* |
| 5026 | SA | *Staphylococcus aureus* |
| 5666 | SA | *Staphylococcus aureus* |
| 6792 | SA | *Staphylococcus aureus* |
| 7023 | SA | *Staphylococcus aureus* |
| 7461 | SA | *Staphylococcus aureus* |
| 7899 | SA | *Staphylococcus aureus* |
| 7901 | SA | *Staphylococcus aureus* |
| 8714 | SA | *Staphylococcus aureus* |
| 9374 | SA | *Staphylococcus aureus* |
| 9437 | SA | *Staphylococcus aureus* |
| 10056 | SA | *Staphylococcus aureus* |
| 10110 | SA | *Staphylococcus aureus* |
| 11379 | SA | *Staphylococcus aureus* |
| 11629 | SA | *Staphylococcus aureus* |
| 11659 | SA | *Staphylococcus aureus* |
| 12788 | SA | *Staphylococcus aureus* |
| 12789 | SA | *Staphylococcus aureus* |
| 13043 | SA | *Staphylococcus aureus* |
| 13086 | SA | *Staphylococcus aureus* |
| 13721 | SA | *Staphylococcus aureus* |
| 13742 | SA | *Staphylococcus aureus* |
| 13932 | SA | *Staphylococcus aureus* |
| 14210 | SA | *Staphylococcus aureus* |
| 14384 | SA | *Staphylococcus aureus* |
| 15428 | SA | *Staphylococcus aureus* |
| 15430 | SA | *Staphylococcus aureus* |
| 17721 | SA | *Staphylococcus aureus* |
| 18688 | SA | *Staphylococcus aureus* |
| 19095 | SA | *Staphylococcus aureus* |
| 20195 | SA | *Staphylococcus aureus* |
| 22141 | SA | *Staphylococcus aureus* |
| 22689 | SA | *Staphylococcus aureus* |
| 27398 | SA | *Staphylococcus aureus* |
| 29048 | SA | *Staphylococcus aureus* |
| 29051 | SA | *Staphylococcus aureus* |
| 30491 | SA | *Staphylococcus aureus* |
| 30538 | SA | *Staphylococcus aureus* |
| 25 | SEPI | *Staphylococcus epidermidis* |
| 53 | SEPI | *Staphylococcus epidermidis* |
| 385 | SEPI | *Staphylococcus epidermidis* |
| 398 | SEPI | *Staphylococcus epidermidis* |
| 701 | SEPI | *Staphylococcus epidermidis* |
| 713 | SEPI | *Staphylococcus epidermidis* |
| 1381 | SEPI | *Staphylococcus epidermidis* |
| 2174 | SEPI | *Staphylococcus epidermidis* |
| 2286 | SEPI | *Staphylococcus epidermidis* |
| 2969 | SEPI | *Staphylococcus epidermidis* |
| 3417 | SEPI | *Staphylococcus epidermidis* |
| 3447 | SEPI | *Staphylococcus epidermidis* |
| 4753 | SEPI | *Staphylococcus epidermidis* |
| 7241 | SEPI | *Staphylococcus epidermidis* |
| 9366 | SEPI | *Staphylococcus epidermidis* |
| 10665 | SEPI | *Staphylococcus epidermidis* |
| 11792 | SEPI | *Staphylococcus epidermidis* |
| 12311 | SEPI | *Staphylococcus epidermidis* |
| 13036 | SEPI | *Staphylococcus epidermidis* |
| 13227 | SEPI | *Staphylococcus epidermidis* |
| 13243 | SEPI | *Staphylococcus epidermidis* |
| 13621 | SEPI | *Staphylococcus epidermidis* |
| 13638 | SEPI | *Staphylococcus epidermidis* |
| 13800 | SEPI | *Staphylococcus epidermidis* |
| 14078 | SEPI | *Staphylococcus epidermidis* |
| 14392 | SEPI | *Staphylococcus epidermidis* |
| 15007 | SEPI | *Staphylococcus epidermidis* |
| 16733 | SEPI | *Staphylococcus epidermidis* |
| 18871 | SEPI | *Staphylococcus epidermidis* |
| 23285 | SEPI | *Staphylococcus epidermidis* |
| 27805 | SEPI | *Staphylococcus epidermidis* |
| 29679 | SEPI | *Staphylococcus epidermidis* |
| 29985 | SEPI | *Staphylococcus epidermidis* |
| 30259 | SEPI | *Staphylococcus epidermidis* |
| 31444 | SEPI | *Staphylococcus epidermidis* |
| 268 | SPN | *Streptococcus pneumoniae* |
| 1264 | SPN | *Streptococcus pneumoniae* |
| 2482 | SPN | *Streptococcus pneumoniae* |
| 2653 | SPN | *Streptococcus pneumoniae* |
| 2994 | SPN | *Streptococcus pneumoniae* |
| 3123 | SPN | *Streptococcus pneumoniae* |
| 3124 | SPN | *Streptococcus pneumoniae* |
| 4336 | SPN | *Streptococcus pneumoniae* |
| 4858 | SPN | *Streptococcus pneumoniae* |
| 5606 | SPN | *Streptococcus pneumoniae* |
| 5881 | SPN | *Streptococcus pneumoniae* |
| 5897 | SPN | *Streptococcus pneumoniae* |
| 5900 | SPN | *Streptococcus pneumoniae* |
| 6051 | SPN | *Streptococcus pneumoniae* |
| 6216 | SPN | *Streptococcus pneumoniae* |
| 6556 | SPN | *Streptococcus pneumoniae* |
| 7270 | SPN | *Streptococcus pneumoniae* |
| 7584 | SPN | *Streptococcus pneumoniae* |
| 8479 | SPN | *Streptococcus pneumoniae* |
| 8501 | SPN | *Streptococcus pneumoniae* |
| 9256 | SPN | *Streptococcus pneumoniae* |
| 9257 | SPN | *Streptococcus pneumoniae* |
| 10246 | SPN | *Streptococcus pneumoniae* |
| 10467 | SPN | *Streptococcus pneumoniae* |
| 10886 | SPN | *Streptococcus pneumoniae* |
| 11217 | SPN | *Streptococcus pneumoniae* |
| 11228 | SPN | *Streptococcus pneumoniae* |
| 11238 | SPN | *Streptococcus pneumoniae* |
| 11757 | SPN | *Streptococcus pneumoniae* |
| 11768 | SPN | *Streptococcus pneumoniae* |
| 12121 | SPN | *Streptococcus pneumoniae* |
| 12124 | SPN | *Streptococcus pneumoniae* |
| 12149 | SPN | *Streptococcus pneumoniae* |
| 12767 | SPN | *Streptococcus pneumoniae* |
| 12988 | SPN | *Streptococcus pneumoniae* |
| 13321 | SPN | *Streptococcus pneumoniae* |
| 13393 | SPN | *Streptococcus pneumoniae* |
| 13521 | SPN | *Streptococcus pneumoniae* |
| 13544 | SPN | *Streptococcus pneumoniae* |
| 13700 | SPN | *Streptococcus pneumoniae* |
| 13704 | SPN | *Streptococcus pneumoniae* |
| 13822 | SPN | *Streptococcus pneumoniae* |
| 13838 | SPN | *Streptococcus pneumoniae* |
| 14131 | SPN | *Streptococcus pneumoniae* |
| 14413 | SPN | *Streptococcus pneumoniae* |
| 14744 | SPN | *Streptococcus pneumoniae* |
| 14808 | SPN | *Streptococcus pneumoniae* |
| 14827 | SPN | *Streptococcus pneumoniae* |
| 14835 | SPN | *Streptococcus pneumoniae* |
| 14836 | SPN | *Streptococcus pneumoniae* |
| 15832 | SPN | *Streptococcus pneumoniae* |
| 17336 | SPN | *Streptococcus pneumoniae* |
| 17343 | SPN | *Streptococcus pneumoniae* |

TABLE 5-continued

Panels of Gram Positive and Gram Negative Organism Used to GenerateMIC90 Data

| JMI Isolate # | JMI Organism Code | Organism |
|---|---|---|
| 17349 | SPN | Streptococcus pneumoniae |
| 17735 | SPN | Streptococcus pneumoniae |
| 18060 | SPN | Streptococcus pneumoniae |
| 18567 | SPN | Streptococcus pneumoniae |
| 18595 | SPN | Streptococcus pneumoniae |
| 19082 | SPN | Streptococcus pneumoniae |
| 19826 | SPN | Streptococcus pneumoniae |
| 22174 | SPN | Streptococcus pneumoniae |
| 22175 | SPN | Streptococcus pneumoniae |
| 27003 | SPN | Streptococcus pneumoniae |
| 28310 | SPN | Streptococcus pneumoniae |
| 28312 | SPN | Streptococcus pneumoniae |
| 29890 | SPN | Streptococcus pneumoniae |
| 29910 | SPN | Streptococcus pneumoniae |

Example 32

Mouse *S. Aureus* Kidney Infection Model

Animals: female CD-1 mice (8-10 weeks of age; 6/group), were obtained from Charles River Laboratories and were housed and maintained in accordance with the Guide to the Care and Use of Experimental Animals.

Bacterial Strain and Stocks

Methicillin-sensitive *S. aureus* (MSSA) strain ATCC 29213 was obtained from the American Type Culture Collection. To prepare stocks for animal studies *S. aureus* was plated on Mueller Hinton Agar plates and incubated at 37° C. overnight. 3-4 colonies from the plate were used to inoculate 5 mL Mueller Hinton Broth (MHB) that was incubated for 8 hours at 37° C. with shaking at 300 RPM. The 5 mL 8-hour culture was diluted 20-fold into 100 mL and incubated overnight (12-14 hours). The bacteria were pelleted for 20 minutes at 3000× and washed twice with Phosphate-Buffered Saline (PBS) containing 0.5% Bovine Serum Albumin (BSA). Aliquots (1 mL) containing ~$1 \times 10^{10}$ cfu in PBS/20% Glycerol were frozen and stored at −80° C. until the day of use. Stock titers were confirmed by serial dilution and plating on Mueller Hinton agar plates.

Mouse *S. Aureus* Kidney Infection Model

Prior to inoculation, bacterial stocks were thawed and washed once with PBS/BSA. The stocks were then diluted with PBS/BSA to a final concentration of $1 \times 10^9$ cfu/mL to give an inoculum of approximately $1-2 \times 10^8$ cfu per mouse in a volume of 100 uL. This inoculum was found to be optimal in preliminary experiments that utilized challenge doses of $10^6$-$10^9$ *S. aureus* organisms/mouse to establish a ~$10^6$ cfu/kidneys burden at 26 hours post infection without mortality (data not shown). In these preliminary studies challenge with *S. aureus* at less than $10^7$ cfu/mouse induced inconsistent or no chronic infections, whereas a dose of $10^9$ cfu/mouse resulted in rapid illness and mortality in a high percentage of the mice. Injections were given intravenously via the tail vein using a sterile 30 gauge needle. Upon completion of the mouse infections, the bacterial stocks used to challenge the mice were plated and counted to verify the concentration of the inocula.

To assess the bacterial burden at the indicated times post infection (most commonly 2 to 26 hours), mice were euthanized and the kidneys were aseptically harvested, and placed into sterile PBS/BSA (5 mL/pair kidneys). Kidneys were homogenized under sterile conditions, using a hand held homogenizer (Powergen 125; Fisher Scientific). During collection and homogenization all of the samples were kept on ice and the homogenizer was washed thoroughly and sterilized between each sample. Homogenates were serially diluted in sterile PBS/BSA and plated on MH agar to determine bacterial counts per pair of kidneys.

TABLE 6

Compound 23A Reduces *S. aureus* Burdens in the Mouse *S. aureus* Kidney Infection Model

| | Time of Treatment | | | | | |
|---|---|---|---|---|---|---|
| | 30 Minutes | | 6 Hours | | 24 Hours | |
| | Median Kidney Burden (Log cfu/kidneys) | Log Difference vs. Vehicle Control | Median Kidney Burden (Log cfu/kidneys) | Log Difference vs. Vehicle Control | Median Kidney Burden (Log cfu/kidneys) | Log Difference vs. Vehicle Control |
| Vehicle | 4.97 | | 5.21 | | 6.35 | |
| 10 mg/kg Compound 23A | 4.84 | −0.14 | 4.84 | −0.37 | 4.48 | −1.87 |
| 30 mg/kg Compound 23A | 4.97 | 0.00 | 4.62 | −0.59 | 3.44 | −2.90 |
| 100 mg/kg Compound 23A | 4.89 | −0.08 | 4.55 | −0.66 | 3.49 | −2.86 |

CD-1 mice (6/group) were challenged IV with *S. aureus* (ATCC 29213) at $2 \times 10^8$ cfu/mouse. Two hours post challenge mice were treated via oral gavage with Vehicle (10% VitE TPGS) at 10 ml/kg or Compound 23A at 10, 30, 100 mg/kg. The 30-minute and 6-hour treatment groups were treated once, while the 24-hour group received a second treatment 10 hours after the first dose. After increasing amounts of time post treatment (30 minutes, 6 hours or 24 hours), the mice were euthanized and the kidneys harvested, homogenized and plated to quantitate *S. aureus* burdens. Burdens from pairs of kidneys for each mouse and the median for each group of mice werecalculated.

Results: Orally administered Compound 23A exhibited in vivo efficacy against experimentally induced kidney MSSA (SA 29213) infection. At 30 minutes after the initial treatment there was no difference in kidney burden between compound- and vehicle-treated mice. The 30 minute vehicle-treated group served as early control for comparison of compound effects at later time points. At 6 hours after the first dose, all compound treatments reduced bacterial burdens in the kidneys by 0.4-0.6 logs versus time-matched vehicle control. Additionally, Compound 23A administered at 30 and 100 mg/kg provided 0.3-0.4 log reduction versus the 30 minute early control.

After a treatment period of 24 hours (that included a second dose of treatment administered at 10 hours), a decrease in bacterial density compared to time-matched vehicle control was observed for all treatment groups. Compound 23A administered at 30 and 100 mg/kg BID provided 2.8-2.9 log reduction, whereas 10 mg/kg Compound 23A BID was more variable and provided a 1.8 log reduction versus the 24-hour vehicle-treated control. In addition, Compound 23A administered at 30 and 100 mg/kg showed approximately 1.5 log reductions versus the 30-minute vehicle-treated control, indicative of bactericidal activity.

In summary and as shown above in Table 6, BID dosing of 30 and 100 mg/kg Compound 23A diminished bacterial growth of methicillin-sensitive S. aureus (MSSA) strain ATCC 29213 as compared to the 30 minute control group at both the 6 hours and 24 hour assessment times while treatment with 10 mg/kg Compound 23A limited bacterial growth at 6 hours but was less effective than other treatment groups at 24 hours.

TABLE 7

A Single Dose of Compound 23A Reduces S. aureus Burdens in the Mouse S. aureus Kidney Infection Model

| Treatment Group | Median Kidney Burden (Log cfu/kidneys) | Log Reduction vs. Early Control | Log Reduction vs. Late Control |
|---|---|---|---|
| Early Control | 4.73 | | |
| Late Control | 6.63 | 1.90 | |
| 10 mg/kg Compound 23A | 4.73 | 0.00 | −1.90 |
| 30 mg/kg Compound 23A | 4.32 | −0.40 | −2.31 |
| 60 mg/kg Compound 23A | 3.52 | −1.21 | −3.11 |
| 100 mg/kg Compound 23A | 3.31 | −1.42 | −3.32 |

CD-1 mice (6/group) were challenged IV with S. aureus (ATCC 29213) at $2\times10^8$ cfu/mouse. After 2 hours a single group of mice (Early Control (EC)) was euthanized and the kidneys harvested, homogenized and plated to quantitate S. aureus burdens. The additional groups of infected mice were treated via oral gavage with Vehicle at 10 ml/kg (10% VitE TPGS; Late Control, LC), Compound 23A at 10, 30, 60, 100 mg/kg. After 24 hours the groups of treated mice were euthanized and the kidneys harvested, homogenized and plated to quantitate S. aureus burdens. Burdens from pairs of kidneys for each mouse and the median for each group of mice were summarized.

Results: In summary and as shown above in Table 7, a single oral dose of Compound 23A exhibited in vivo efficacy against an experimentally induced kidney MSSA (SA 29213) infection. After 24 hours all treatments showed decreases in bacterial density compared to time-matched vehicle control. Compound 23A demonstrated dose-dependent reductions of 1.9, 2.3, 3.1 and 3.3 log reductions versus vehicle control when administered at 10, 30, 60 or 100 mg/kg. In addition, doses of 60 and 100 mg/kg Compound 23A reduced bacterial burdens versus the early control by 1.2-1.4 logs suggesting Compound 23A has bactericidal activity.

TABLE 7A

A Single Dose of Compound W Reduces Bacterial Burdens in the Mouse MSSA Kidney Infection Model

| Treatment Group (Compound W Single Dose Equivalent) | Median Kidney Burden ($Log_{10}$ CFU/kidneys) | $Log_{10}$ Difference vs. Early Control | $Log_{10}$ Difference vs. Late Control |
|---|---|---|---|
| Early Control | 4.40 | | |
| Late Control | 5.94 | 1.54 | |
| 16 (10) mg/kg Compound W | 3.69 | −0.71 | −2.25 |
| 49 (30) mg/kg Compound W | 3.22 | −1.18 | −2.72 |
| 99 (60) mg/kg Compound W | 3.32 | −1.08 | −2.62 |
| 166 (100) mg/kg Compound W | 2.94 | −1.46 | −3.00 |

CD-1 mice (8/group) were challenged IV with S. aureus (ATCC 29213) at $2\times10^8$ cfu/mouse. After 2 hours a single group of mice (Early Control (EC)) was euthanized and the kidneys harvested, homogenized and plated to quantitate S. aureus burdens. The additional groups of infected mice were treated via oral gavage with Vehicle at 10 ml/kg (Water; Late Control, LC), Compound W was administered at 16, 49, 99 or 166 mg/kg nominal dose levels that were expected to deliver 10, 30, 60 or 100 mg/kg of Compound 23A, the active moiety dose equivalents upon complete conversion at 10, 30, 60, 100 mg/kg. After 24 hours the groups of treated mice were euthanized and the kidneys harvested, homogenized and plated to quantitate S. aureus burdens. Burdens from pairs of kidneys for each mouse and the median for each group of mice were summarized.

Results: In summary and as shown above in Table 8, a single oral dose of Compound W exhibited in vivo efficacy against an experimentally induced kidney MSSA (SA 29213) infection. After 24 hours all treatments showed decreases in bacterial density compared to time-matched vehicle control. Compound W demonstrated dose-dependent reductions of 1.9, 2.3, 2.7, 2.6 and 3.0 log reductions versus vehicle control when administered at 16, 49, 99 and 166 mg/kg that provided equivalent exposures of 10, 30, 60 or 100 mg/kg compound 24. In addition, doses of 16, 49, 99 and 166 mg/kg Compound W reduced bacterial burdens versus the early control by 0.7-1.5 logs suggesting Compound 23A has bactericidal activity.

Example 33

NeutropenicRat Thigh Infection Model

Animals: Specific-pathogen-free, male Sprague Dawley rats weighing between 76 to 100 grams were obtained from Charles River Laboratories, Inc. (Wilmington, Mass.) and utilized in this experiment. Animals were allowed to acclimate for a minimum of seven (7) days before study commencement.

Bacteria: The methicillin-sensitive Staphylococcus aureus (MSSA) ATCC strain 29213 was utilized for in vivo experimentation. The test isolate was subcultured twice onto standard microbiological agar media (trypticase soy agar with 5% sheep blood). The second transfer was made less than 24 hours before use in the preparation of the thigh infection model inoculum.

Neutropenic Rat Thigh Infection Model: To induce neutropenia, rats were treated with the immunosuppressant cyclophosphamide at 150 mg/kg, administered in 1 ml by intraperitoneal (IP) injection, three day prior to infection. Rats were infected by an intramuscular (IM) 0.2 ml injection into both rear thighs with a $10^7$ cfu/ml methicillin-sensitive *Staphylococcus aureus* 29213 suspension in normal saline. After increasing amounts of time (2-26 hours) the two rear thighs of each animal were harvested, rinsed with sterile saline, weighed, then placed in 50 ml sterile normal saline and placed on wet ice until homogenization. Approximately one-half of the total homogenized sample volume was passed through a large pore filter (to remove cartilage and large clumped pieces of tissue), diluted in saline and cultured onto agar media plates (trypticase soy agar with 5% sheep blood). All culture plates were incubated at approximately 37° C. for 18-24 hours. Colony-forming units were enumerated (in cfu/ml of homogenate) and the median for each treatment and control group was calculated. Typically each group had an n=6; each thigh was considered a discrete number. The median cfu/ml per group was compared to the initial bacterial density at 2 hours (Early Control) or that of the time-matched vehicle control group (Late Control; LC) group harvested simultaneously.

(20% Cavitron/1% HPMCAS-MG; Late Control, LC) or Compound 23A at 10, 30, 60 mg/kg. The 8-hour treatment groups received a single treatment (QD) and were euthanized and thighs collected for cfu determination 8 hours post treatment (QD), while the 24-hour treatment groups received 2 doses 12 hours apart (q12 h) and were euthanized and thighs collected 24 hours post treatment. Burdens from each individual thigh were determined and the cfu/ml and the median from the group of 3 rats was summarized.

Results: As shown above in Table 8, orally administered Compound 23A exhibited in vivo efficacy against the MSSA (SA 29213). At 8 hours after the first dose all of the groups had reductions in burdens compared to time-matched control, ~1.3 log reduction for Compound 23A at 10 mg/kg and ~2 log reduction for Compound 23A at 30 and 60 mg/kg. Compared to early control, Compound 23A at 10 mg/kg held the bacterial growth of SA 29213 to at least the point of stasis, whereas Compound 23A at 60 and 100 mg/kg slightly decreased the bacterial burden by ~0.5-0.6 logs.

TABLE 8

Compound 23A Demonstrates Dose-Related and Time-Dependent Reductions in S. aureus Thigh Burdens in Neutropenic Rats

| | Treatment Time | | | | | |
|---|---|---|---|---|---|---|
| | 8 Hours | | | 24 Hours | | |
| Treatment Group | Median Thigh Burden (Log cfu/mL) | Log Difference vs. Early Control | Log Reduction vs. Late Control (8-hour) | Median Thigh Burden (Log cfu/mL) | Log Difference vs. Early Control | Log Difference vs. Late Control (24-hour) |
| Early Control | 5.37 | | | 5.37 | | |
| Late Control | 6.77 | 1.41 | | 6.99 | 1.62 | |
| 10 mg/kg Compound 23A | 5.42 | 0.05 | −1.36 | 4.59 | −0.78 | −2.40 |
| 30 mg/kg Compound 23A | 4.75 | −0.62 | −2.02 | 4.31 | −1.06 | −2.68 |
| 60 mg/kg Compound 23A | 4.80 | −0.57 | −1.97 | 4.19 | −1.18 | −2.80 |

Neutropenic rats (3/group) were infected by intramuscular (IM) challenge with *S. aureus* (ATCC 29213) at ~2×10$^6$ cfu/thigh. After 2 hours a single group of rats (Early Control (EC) was euthanized and the thighs harvested, homogenized and plated to quantitate *S. aureus* burdens. The additional infected rats were treated by oral gavage with Vehicle at 10 ml/kg After 24 hours and a second dose of treatment administered at 12 hours, a decrease in bacterial density compared to late control of ~2.4-2.8 logs was observed for all treatment groups. Compared to early control an approximately 0.8 log reduction was observed for Compound 23A at 10 mg/kg, while Compound 23A at 30 and 60 mg/kg provided ~1.1-1.2 log reductions.

TABLE 9

Compound 13 Demonstrates Dose-Related and Time-Dependent Reductions in S. aureus Thigh Burdens in Neutropenic Rats

| | Treatment Time | | | | | |
|---|---|---|---|---|---|---|
| | 8 Hours | | | 24 Hours | | |
| Treatment Group | Median Thigh Burden (Log cfu/mL) | Log Difference vs. Early Control | Log Difference vs. Late Control (8-hour) | Median Thigh Burden (Log cfu/mL) | Log Difference vs. Early Control | Log Difference vs. Late Control (24-hour) |
| Early Control | 5.30 | | | 5.30 | | |
| Late Control | 6.64 | 1.34 | | 7.16 | 1.86 | |

TABLE 9-continued

Compound 13 Demonstrates Dose-Related and Time-Dependent Reductions in
S. aureus Thigh Burdens in Neutropenic Rats

| | Treatment Time | | | | | |
|---|---|---|---|---|---|---|
| | 8 Hours | | | 24 Hours | | |
| Treatment Group | Median Thigh Burden (Log cfu/mL) | Log Difference vs. Early Control | Log Difference vs. Late Control (8-hour) | Median Thigh Burden (Log cfu/mL) | Log Difference vs. Early Control | Log Difference vs. Late Control (24-hour) |
| 10 mg/kg Compound 13 | 5.15 | −0.15 | −1.49 | 6.02 | 0.72 | −1.14 |
| 60 mg/kg Compound 13 | 4.95 | −0.35 | −1.69 | 4.31 | −0.99 | −2.85 |
| 100 mg/kg Compound 13 | 4.82 | −0.48 | −1.82 | 4.17 | −1.13 | −2.99 |

Neutropenic rats (3/group) were infected by intramuscular (IM) challenge with S. aureus (ATCC 29213) at ~2×10$^6$ cfu/thigh. After 2 hours a single group of rats (Early Control (EC)) was euthanized and the thighs harvested, homogenized and plated to quantitate S. aureus burdens. The additional infected rats were treated by oral gavage with Vehicle at 10 ml/kg (10% Vitamin E/TPGS; Late Control, LC) or Compound 13 at 30, 60, 100 mg/kg. The 8-hour treatment groups received a single treatment (QD) and were euthanized and thighs collected for cfu determination 8 hours post treatment (QD), while the 24 hour treatment groups received 2 doses 12 hours apart (q12 h) and were euthanized and thighs collected 24 hours post treatment. Burdens from each individual thigh were determined and the cfu/individual thigh and the median from the group of 3 rats was summarized for each group.

Results: As shown above in Table 9, orally administered Compound 13 exhibited in vivo efficacy against the MSSA (SA 29213). Differences in the extent of antibacterial activity were seen between the three treatment groups. At 8 hours after the first dose all of the groups had reductions in burdens compared to time-matched control, ~1.5 log reduction for Compound 13 at 10 mg/kg and ~1.7 and 1.8 log reduction for Compound 13 at 60 and 100 mg/kg. At 8 hours after the first dose, Compound 13 at 10 mg/kg held the bacterial growth of SA 29213 to at least the point of stasis, whereas Compound 13 at 60 and 100 mg/kg slightly decreased the bacterial burden versus early control by ~0.4 and ~0.5 logs respectively. After 24 hours and the second dose of treatment administered at 12 hours, a decrease in bacterial density compared to early control of approximately 1 log was exhibited by Compound 13 at 60 and 100 mg/kg. In contrast, Compound 13 administered at 30 mg/kg did not appear effective with variable cfu levels averaging 0.3 logs greater than the early control. However, all dose levels decreased bacterial density compared to late control. A reduction of ~1.1 log was observed for the 10 mg/kg treatment group, whereas a reduction of 2.85 and ~3 logs was observed for the 60 and 100 mg/kg dose levels.

In summary, the q12 h doses of 60 and 100 mg/kg Compound 13 diminished bacterial growth of SA 29213 as compared to the initial control group at both the 8 hours and 24 hours assessment times while treatment with 30 mg/kg limited bacterial growth at 8 hours but was less effective than other treatment groups at 24 hours.

Example 34

Seven-Day Oral (Gavage) Toxicity and Toxicokinetics Study in Rats

The objectives of this study were: 1) to evaluate the potential toxicity of Compound 13 and Compound 23A when administered orally by gavage to male rats for 7 consecutive days and 2) to assess the toxicokinetics of Compound 13, and Compound 23A after the first and seventh doses.

Animals

Species, Source, Histo and Justification

Crl:CD(SD) rats were obtained from Charles River Laboratories of Stone Ridge, N.Y. The animals were laboratory bred and experimentally naïve. Rats were chosen because they are a species that is commonly used for nonclinical toxicity evaluations.

Number, Sex, Age, and BodyWeightRange

Forty rats (20 noncannulated males and 20 males with jugular vein cannulas) were ordered. From these animals, 15 noncannulated males and 15 cannulated males were used. Animals were as uniform in age as possible. The rats were prepubertal to young adult, approximately 9 weeks of age at initiation of dosing. Their supplier-calculated birth date was retained in the study records. The weight range for the animals at the time of allocation to groups was 218.5-306.3 g.

Study Design

The rats were assigned as shown in the Table 10 below. Animals received the test article or vehicle by oral gavage for 7 consecutive days and were terminated the day following completion of dosing. The first day of dosing was designated as Day 1 of the study. The animals were evaluated for changes in clinical signs, body weight, and other parameters as described below.

TABLE 10

Group Assignment and Dose Levels

| Dose Group | No. Animals (M) Main Study | No. Animals (M) Toxicokinetics | Test Article | Dose Level (mg/kg/day) | Doses per Day | Dose Concentration (mg/mL) | Dose Volume (mL/kg) | Animals for Necropsy (Day 8) |
|---|---|---|---|---|---|---|---|---|
| A | 3 | 0 | Vehicle | 0 | 1 | 0 | 10 | 3 |
| B | 3 | 3 | Compound 13 | 100 | 1 | 10 | 10 | 6 |
| C | 3 | 3 | Compound 13 | 200 | 1 | 20 | 10 | 6 |
| D | 3 | 3 | Compound 23A | 100 | 1 | 10 | 10 | 6 |
| E | 3 | 3 | Compound 23A | 300 | 2 | 30 | 10 | 6 |
| F | 0 | 3 | Vehicle | 0 | 2 | 0 | 10 | 3 |

Route/Dose

The vehicle and test article were administered by oral gavage once daily for 7 consecutive days at a dose volume of 10 mL/kg body weight for Group A and Groups B-D, respectively. The test article and vehicle were administered by oral gavage twice daily, approximately 8 hours apart, for 7 consecutive days at a dose volume of 10 mL/kg body weight for Group E and Group F, respectively. The actual volume administered to each animal was calculated and adjusted based on the most recent body weight of each animal.

In-Life Observations and Measurements

Observations

Animals were observed for viability at least once in the morning and once in the afternoon, at least 4 hours apart, throughout the study. During the treatment period, daily cageside observations were made and recorded predose and postdose (following the first dose only). The postdosing observations made during treatment occurred at the following times based on $C_{max}/T_{max}$ for the two compounds from previous studies:

1 hour postdose for Groups A-F.

One cageside observation was made on the day of necropsy.

Unscheduled Observations

Any findings observed at times other than scheduled observation times were to be recorded on an unscheduled observation or in Provantis; however, no abnormalities were observed throughout the study. Provantis is an electronic data collection, management and reporting system that is commonly used in the art.

Body Weights

Prior to start of dosing, body weights were measured for randomization on Day 1. During the treatment, body weights were measured on Day 1 and Day 7. In addition, fasted body weights were measured prior to necropsy for calculation of organ/body weight ratios.

Food Consumption

Throughout the study, food consumption was measured daily starting 3 days prior to start of dosing.

Clinical Pathology Evaluation

Blood samples for evaluation of hematology, coagulation, and serum chemistry parameters were collected from all animals from the retro-orbital plexus (under $CO_2/O_2$ anesthesia, for the main study animals) or jugular vein cannula (for the toxicokinetic animals) prior to necropsy. Due to residual heparin used to keep the cannulas patent for the toxicokinetic animals, coagulation samples from these rats, were not able to be analyzed. The animals were fasted overnight prior to blood collection. On the day of blood collection for clinical pathology analyses, the animals were not necropsied until after the blood was collected and the samples judged to be acceptable by the clinical pathology group.

Hematology

An appropriate amount of blood was collected in EDTA-containing tubes. The whole blood samples were analyzed for the parameters indicated below in Table 11.

TABLE 11

Whole Blood Parameters

| | |
|---|---|
| Red blood cells (RBC) (count and morphology) | Mean corpuscular volume (MCV) |
| White blood cells (WBC) (total and differential) | Mean corpuscular hemoglobin (MCH) |
| Hemoglobin concentration (HGB) | Mean corpuscular hemoglobin concentration (MCHC) |
| Hematocrit (HCT) | Platelet count |
| Reticulocyte count (ABSRET) | (PLAT) Mean platelet volume (MPV) |

Coagulation

An appropriate amount of blood was collected in tubes containing sodium citrate and then centrifuged to obtain plasma for the determination of prothrombin time (PT) and activated partial thromboplastin time (APTT).

Serum Chemistry

An appropriate amount of blood was collected in tubes without anticoagulant. The sample was allowed to clot and then was centrifuged to obtain serum. The serum was analyzed for the parameters indicated below in Table 12.

TABLE 12

Serum Parameters

| | |
|---|---|
| Sodium (NA) | Calcium (CA) |
| Potassium (K) | Inorganic phosphorus (PHOS) |
| Chloride (CL) | Glucose (GLU) |
| Total bilirubin (TBILI) | Urea nitrogen (BUN) |
| Alkaline phosphatase (ALKP) | Total protein (TPRO) |
| Lactate dehydrogenase (LDH) | Albumin (ALB) |
| Aspartate aminotransferase (AST) | Globulin (GLOB) |
| Alanine aminotransferase (ALT) | Albumin/globulin ratio (A/G) |
| Gamma-glutamyltransferase (GGT) | Cholesterol (CHOL) |
| Creatine phosphokinase (CK) | Triglycerides (TRIG) |
| Creatinine (CREA) | |

Toxicokinetics

On the $1^{st}$ and $7^{th}$ day a of dosing, blood samples (approximately 0.5 mL/sample) were collected from the jugular vein cannula for all toxicokinetic animals at the timepoints listed below into $K_3$EDTA-containing tubes. Toxicokinetic animals from the control group (Group F) only had a single blood collection sampling from each collection day at the 1-hour timepoint (following the first dose administration of the day). Prior to each collection, a small sample of blood (with heparin blocking solution) was removed from the cannula and discarded. A new syringe was placed on the cannula, and the protocol-required sample was taken. The syringe with the blood sample was removed, and a new syringe with saline attached to the cannula. Blood volume was replaced with an equal volume of saline and then blocking solution placed in the cannula. Each animal was returned to its cage until the next collection timepoint.

All samples collected during this study were placed in labeled containers. Each label contained the following information: 1) Study number, 2) Animal number, 3) collection interval, 4) Group and Sex, and 5) Date of collection.

The blood samples were mixed immediately by inverting, then placed on wet ice and centrifuged cold (~1500 g, ~10 minutes, ~5° C.) to obtain plasma. The plasma was split into 96-well 1.4-mL polypropylene tubes with pierceable TPE capcluster certified RNase, DNase free caps as 2 aliquots and stored frozen ($\leq -70°$ C.).

TABLE 13

Sample Collection Timepoints

| Timepoint | Window[1] |
|---|---|
| Predose | Predose |
| 1 h | ±4 min |
| 2 h[2] | ±5 min |
| 4 h | ±5 min |
| 8 h[3] | ±5 min |
| 12 h | ±10 min |
| 24 h | ±20 min |
| 48 h[4] | ±40 min |

[1]All samples were collected within the collection window.
[2]Following Day 1 dosing only.
[3]Obtained from Groups E and F prior to PM dose administration.
[4]Following Day 7 dosing only.

Termination

No animal was deemed moribund during the study. All study animals were euthanized and subjected to a necropsy following the protocol-prescribed number of days of treatment. All animals were terminated by exsanguination (severing the abdominal aorta while under deep $CO_2/O_2$ anesthesia).

Necropsy

A necropsy with tissue collection was conducted on all animals terminated during the study. The necropsy included examination of:
carcass and muscular/skeletal system; all external surfaces and orifices;
cranial cavity and external surface of the brain;
neck with associated organs and tissues; and
thoracic, abdominal, and pelvic cavities with their associated organs and tissues.

All abnormalities were described and recorded.

Organ Weights

For all animals euthanized at scheduled necropsies, the kidneys, liver, and prostate gland were weighed. Following weighing, an approximate 1 gram sample of liver and kidney was weighed, transferred to Precellys 7 mL CK28 Tissue Homogenizing tubes (Cat. No. 0904-01), snap-frozen, and analyzed.

Organ/body ratios were calculated using the terminal fasted body weight obtained prior to necropsy.

Tissue Preservation and Bone Marrow Collection

The tissues and organs indicated below in Table 14 were collected from all animals and were preserved in 10% neutral-buffered formalin with the exception of the testes, epididymides, and eyes. Testes, epididymides, and eyes with optic nerve attached were fixed in Modified Davidson's Solution for ~24-48 hours, rinsed with water, and then transferred to 10% neutral-buffered formalin for storage.

TABLE 14

Tissue Collection

| Tissue | Submitted at Necropsy | Organ Weight | Histopathology |
|---|---|---|---|
| Animal ID | X | | |
| Adrenal gland (2) | X | | |
| Aorta | X | | |
| Artery, mesenteric | X | | |
| Bone (femur) | X | | |
| Bone marrow (sternum) | X | | |
| Brain | X | | |
| Epididymides (2) | X | | |
| Esophagus | X | | |
| Eyes (2) | X | | |
| Gross lesions | X | | |
| Heart | X | | |
| Intestine, cecum | X | | |
| Intestine, colon | X | | |
| Intestine, duodenum | X | | |
| Intestine, jejunum | X | | |
| Intestine, ileum | X | | |
| Intestine, rectum | X | | |
| Kidneys (2) | X | X | X |
| Liver | X | X | X |
| Lungs | X | | |
| Lymph node, mandibular | X | | |
| Lymph node, mesenteric | X | | |
| Mammary gland | X | | |
| Nerve, optic | X | | |
| Nerve, sciatic | X | | |
| Parathyroid gland (2)[a] | X | | |
| Pancreas | X | | |
| Pituitary | X | | |
| Prostate | X | X | X |
| Seminal vesicles | X | | |
| Skeletal muscle (biceps femoris) | X | | |
| Skin (abdominal) | X | | |
| Spinal cord, cervical | X | | |
| Spinal cord, thoracic | X | | |
| Spinal cord, lumbar | X | | |
| Spleen | X | | |
| Stomach | X | | |
| Testes (2) | X | | |
| Thymus | X | | |
| Thyroid gland (2)[a] | X | | |
| Tongue | X | | |
| Trachea | X | | |
| Urinary bladder | X | | |

[a]Thyroid weighed with parathyroids attached.

Histopathology

For all animals scheduled for the terminal necropsy, the kidneys, liver, and prostate were embedded in paraffin, sectioned and stained with hematoxylin and eosin for further examination by light microscopy. For Groups A, D, E, and F only, the remaining tissues listed above were embedded in paraffin, sectioned and stained with hematoxylin and eosin for further examination by light microscopy.

Statistical Analysis

Where appropriate, numeric animal data were evaluated statistically.

For comparative statistics, Group A (control group) was compared to Groups B and C (treated groups, dosed QD) and Group F (control group, dosed BID) was compared to Group E (treated group, dosed BID). Data were evaluated using the Levene Test for homogeneity of variances and the Shapiro-Wilks Test for normality of distributions, with significance at p≤0.05. Data determined to be homogeneous and of normal distribution were evaluated by analysis of variance (ANOVA). If the ANOVA verified significance at p≤0.05, pairwise comparisons of each treated group with the respective control group were made using a parametric test (Dunnett Test) to identify statistical differences (p≤0.05). Data determined to be nonhomogeneous or of normormal distribution were evaluated using a Kruskal-Wallis Test for group factor significance. If significance (p≤0.05) existed between groups, a nonparametric test (Wilcoxonwith Bonferroni-Holm), was used to compare treatment groups to the control group. Food consumption data from animals where spillage occurred was excluded from the applicable time period. Comparative statistics of food consumption data were limited to the Dunnett Test (parametric). Statistics were not performed on pretest food consumption (Day 4 to Day 1).

Results

The exposures for different dosage levels of Compound 23A and Compound 13 were dose related. No adverse observations or effects on mean body weight were observed in animals treated with either Compound 13 or Compound 23A. Mean food consumption was reduced during different intervals of the study for animals treated once daily with Compound 13 (100 or 200 mg/kg) and twice daily with Compound 23A (300 mg/kg). However, as the decreased food consumption was not correlated with body weight changes in the Compound 13 and Compound 23A groups, these effects were not considered to be adverse or biologically significant. The mean calcium ion concentration (CA) was statistically lower, while the mean ALT and the AST for the group of rats administered 300 mg/kg Compound 23A twice a day were statistically higher when compared to the controls treated twice a day. No test article-related histopathological findings were noted for animals receiving either Compound 13 or Compound 23A at any dose regimen.

Within the scope of this study and based on the absence of changes in body weight, clinical pathology, and histopathology, the NOEL (No-Observable-Effect-Level) for Compound 13 administered to male rats once a day for 7 days orally via gavage was 200 mg/kg (844 µg*hr/ml Day 7 AUC), while the NOEL for Compound 23A administered once a day was 100 mg/kg (82 µg*hr/ml AUC). The NOAEL (No-Observable-Adverse-Effect-Level) for Compound 23A administered to male rats twice a day for 7 days orally via gavage was 300 mg/kg (291 µg*hr/ml AUC).

Therefore, Compounds 13 and 23A did not demonstrate adverse toxicity within the scope of the study at dose levels up to 200 mg/kg/day and 600 mg/kg/day, respectively.

Example 35

An Oral Range Finding Toxicity and Toxicokinetic Study in Male Cynomolgus Monkeys The objectives of this study were 1) to evaluate the potential toxicity of Compound 23 when administered orally by gavage to male Cynomolgus monkeys for 7 consecutive days; and 2) to assess the toxicokinetics of Compound 23 after the first and seventh doses.

Animals

Species, Source, History, and Justification

Cynomolgus monkeys (*Macaca Fascicularis*) were obtained from Primus Bio-Resources Inc. of PinCourt, Quebec, Canada. Cynomolgus monkeys were chosen because they are a non-rodent species that is commonly used for nonclinical toxicity evaluations.

Number, Sex, Age, and Body Weight Range

Eight (2 naive and 6 non-naïve) males were used in the study. The animals were young adults and weighed between 2 to 4 kg at the onset of dosing.

Study Design

The animals were assigned as shown in Table 15 below. Animals received Compound 23 or vehicle by oral gavage once per day for 7 consecutive days and were terminated the day following completion of dosing. The first day of dosing was designated as Day 1 of the study. The actual volume administered to each animal was calculated and adjusted based on the most recent body weight of each animal.

TABLE 15

Group Assignment and Dose Levels

| Group | Dose Level (mg/kg) | Dose Concentration (mg/mL) | Dose Volume (mL/kg) | Number of animals |
|---|---|---|---|---|
| 1 | Control* | 0 | 5 | 2 |
| 2 | 50 | 10 | 5 | 2 |
| 3 | 100 | 20 | 5 | 2 |
| 4 | 200 | 40 | 5 | 2 |

*The Control animals received the control/vehicle (20% captisol/1% HPMCAS/1% PVP in 0.01M KCl/HCL buffer) alone In-Life Observations and Measurements Observations Cage-side clinical signs (ill health, behavioral changes etc.) were recorded at least once daily during the study.

Body Weights

Body weights were recorded for all animals prior to group assignment and on Days 1 (prior to dosing), 3 and 7 as well as terminally prior to necropsy (fasted).

Electrocardiography (ECG)

Electrocardiograms (bipolar limb leads I, II and III, and augmented unipolar leads aVR, aVL and aVF) were obtained for all monkeys once during the pre-treatment period and again on Day 7 (post-dosing).

The tracings were assessed for gross changes indicative of cardiac electrical dysfunction. The potential presence of abnormalities involving heart rate (lead II), sinus and atrio-ventricular rhythm or conductivity were determined. Heart rate, PR interval, QRS duration, QT and QTc intervals values were measured.

Toxicokinetics

A series of 7 blood samples (approximately 0.5 mL each) were collected from each monkey on Days 1 and 7 at the following time points: predose, 30 minutes and 2, 3, 6, 12 and 24 hours post-dose. For this purpose, each monkey was bled by venipuncture and the samples were collected into tubes containing the anticoagulant, K2EDTA. Tubes were placed on wet ice until ready for processing.

Clinical Pathology

Laboratory investigations (hematology, coagulation, clinical chemistry and urinalysis) were performed on all animals prior to start of treatment and prior to termination on Day 8.

Blood samples were collected by venipuncture following an overnight period of food deprivation consisting of at least 12 hours but no more than 20 hours. Urine was collected from animals deprived of food and water, overnight (at least 12 hours but no more than 20 hours).

Hematology

The following parameters were measured on blood samples collected into EDTA anticoagulant: red blood cell count, mean corpuscular hemoglobin (calculated), hematocrit (calculated), mean corpuscular volume, hemoglobin, morphology of cells, white blood cell count, platelet count, white blood cell differential (absolute), reticulocyte (absolute and percentage) and mean corpuscular hemoglobin concentration (calculated).

Coagulation

Activated partial thromboplastin time and prothrombin time were measured on blood samples collected into citrate anticoagulant.

Clinical Chemistry

The following parameters were measured on blood samples collected into tubes containing dotting activator: a/g ratio (calculated), creatinine, alanine aminotransferase, globulin (calculated), albumin, glucose, alkaline phosphatase, phosphorus (inorganic), aspartate aminotransferase, potassium, bilirubin (total), sodium, calcium, total protein, chloride, triglycerides, cholesterol (total), urea, gamma glutamyltransferase and sorbitol dehydrogenase.

Urinalysis

The following parameters were measured on urine samples: bilirubin, protein, blood, sediment microscopy, color and appearance, specific gravity, glucose, urobilinogen, ketones, volume and pH.

Termination

All animals were euthanized upon completion of the treatment period on Day 8 following an overnight period without food. The monkeys were pre-anesthetized with Ketamine and then euthanized by an intravenous overdose of sodium pentobarbital followed by exsanguination by transsection of major blood vessels.

Necropsy

A necropsy with tissue collection was conducted on all animals terminated during the study. The necropsy included examination of:

carcass and muscular/skeletal system;
all external surfaces and orifices;
cranial cavity and external surface of the brain;
neck with associated organs and tissues; and
thoracic, abdominal, and pelvic cavities with their associated organs and tissues.

All abnormalities were described and recorded.

Tissue Preservation

On completion of the gross examination and selected organ weighing, the tissues and organs were retained as noted below in Table 16. Neutral buffered 10% formalin was used for fixation and preservation unless otherwise indicated.

TABLE 16

Tissue and Organ Retention

| ORGANS/TISSUES | Retain (•) | Weigh (✓) | Examine (€) | ORGANS/TISSUES | Retain (•) | Weigh (✓) | Examine (€) |
|---|---|---|---|---|---|---|---|
| Adrenals | • | ✓ | € | Pituitary | • | ✓ | € |
| Animal identification | • | | | Prostate | • | ✓ | € |
| Aorta (thoracic) | • | | € | Rectum | • | | € |
| Blood | | | | Salivary Gland, mandibular | • | | € |
| Bone marrow smears (3) | • | | | Sciatic nerve | • | | € |
| Brain | • | ✓ | € | Seminal vesicles | • | | € |
| Cecum | • | | € | Skeletal muscle | • | | € |
| Colon | • | | € | Skin & subcutis (thoracic) | • | | € |
| Epididymides | •d | | € | Duodenum | • | | € |
| Esophagus | • | | € | Jejunum | • | | € |
| Eyes | •a | | € | Ileum | • | | € |
| Femur & marrow | • | | € | Spinal Cord, cervical | • | | € |
| Gallbladder | • | | € | Spleen | • | ✓ | € |
| Heart | • | ✓ | € | Sternum & marrow | • | | € |
| Kidneys | • | ✓ | € | Stomach | • | | € |
| Liver (2 lobes) | • | ✓ | € | Testes | •d | ✓ | € |
| Lungs (2 lobes) | •b | ✓c | € | Thymus | • | ✓ | € |
| Lymph Node, mandibular | • | | € | Thyroid gland/parathyroids | • | ✓ | € |
| Lymph Node, mesenteric | • | | € | Tongue | • | | € |
| Mammary gland (thoracic) | • | | € | Trachea | •c | | |
| Optic nerves | •a | | € | Urinary bladder | • | | € |
| Pancreas | • | | € | Abnormal findings | • | | | a Davidson's fluid used for fixation and preservation
b Lungs were infused with 10% neutral buffered formalin used for fixation and preservation
c Lungs were weighed with trachea
d Bouin's fluid used for fixation and preservation
€ Examined microscopically Histopathology For all animals, all tissues indicated above were embedded in paraffin, sectioned and stained with hematoxylin and eosin and examined by light microscopy.

Results

The exposures for different dosage levels of Compound 23 were dose related.

There were no clinical signs, or changes in body weights, electrocardiography parameters, clinical pathology parameters, or organ weights that could be attributed to the administration of Compound 23 at doses up to 200 mg/kg/day. Similarly, there were no macroscopic or microscopic findings that could clearly be attributed to the administration of Compound 23 at doses up to 200 mg/kg/day. The no observed effect level (NOEL) for Compound 23 in male Cynomolgus monkeys was determined to be 200 mg/kg/day.

Example 36

Pharmacokinetic Studies

The pharmacokinetic parameters of selected compounds of this invention were determined in the experiments described below. General analytic procedures and specific experimental protocols were employed as follows:

General Analytic Procedures

The following general analytic procedures were employed in the pharmacokinetic experiments described below:

Sample Analysis. Concentrations of Compound 23 and Compound W in plasma were determined using a high performance liquid chromatography/tandem mass spectrometry (HPLC/MS/MS) method. Before extraction, plasma samples were diluted using blank plasma 2-, 4-, 5-, or 10-fold, as necessary, depending on the dose level or formulation. Compound 23 and Compound W along with the internal standard (1S) were extracted from (diluted) plasma, 100 µL each, by direct protein precipitation with acetonitrile (1:4 ratio of plasma/acetonitrile). After centrifugation, the supernatant extract (10 µL) was injected onto the LC/MS/MS system. The HPLC system included a Waters Xterra MS C18 column, 5 micron, 2.1 mm diameter×50 mm long eluted with a gradient mobile phase consisting of 0.1% formic acid in water or in acetonitrile.

The analytes were detected by MS/MS with Atmospheric Pressure Chemical Ionization (APCI) in the mode of multiple reaction monitoring (MRM). The lower limit of quantitation (LLOQ) was 1, 2, 4, 5, 10, or 20 ng/mL, depending on the sample dilution factor. The linear range of the assay was from 1 to 5000 ng/mL. The intra-day and inter-day assay accuracy was within 2% of the nominal values. The intra- and inter-day assay variability was <10%.

Samples of the dose suspension formulation of Compound W were assayed with an HPLC/UV method after 10-fold to 500- or 1000-fold of dilution with DMSO:acetonitrile:water (33:33:33) depending on the dose level or formulation. Samples of the dose solution formulation of Compound W were assayed with an HPLC/UV method after 10-, 50-, 100 or 500-fold of dilution with DMSO:water (50:50) depending on the dose level or formulation.

Pharmacokinetic Data Analysis. Plasma concentration-time profiles of Compound 23 and Compound W were analyzed by noncompartmental pharmacokinetic methods using WinNonlin® Professional Edition software, Version 5.1.1 (Pharsight Corporation, Mountain View, Calif.).

Key pharmacokinetic parameters including $AUC_{all}$, $AUC_{extrap}$, $C_{max}$, $t_{max}$, Cl_obs, Vss_obs and $t_{1/2}$ were determined.

Statistical Data Analysis. Descriptive statistical data of plasma concentrations and pharmacokinetic parameter estimates were calculated, including the mean, standard deviation (SD), and coefficient of variation (% CV) using WinNonlin software, Version 5.1.1 or Microsoft Excel 2000.

Monkey Oral Study

Malecynomolgus monkeys (n=3 per dose group) were administered single nominal PO doses of 3, 30 and 300 mg/kg of Compound W by gavage. Compound W was formulated in 0.5% MC (microcrystalline cellulose). Animals had free access to food and water before and after dosing.

Blood samples (approximately 0.25 mL each) were collected via a carotid artery catheter prior to dosing and at 0 (predose), 0.25, 0.5, 1, 2, 3, 4, 6, 8, 12, 24, 48 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma concentration vs. time data was subjected to noncompartmental pharmacokinetic (PK) analysis. The results of this analysis are provided in Table 17.

TABLE 17

Pharmacokinetic Data from Monkey Oral Study

| Dose (mg/kg) | Route | Formulation | Analyte | Cmax (ug/ml) | AUC (ug * hr/ml) | AUCextrap (ug * hr/ml) | Tmax (hr) | t½ (hr) |
|---|---|---|---|---|---|---|---|---|
| 30 | PO | 0.5% MC | Compound 23 | 14.4 | 24.7 | 24.8 | 1.7 | 13.9 |
| 100 | PO | 0.5% MC | Compound 23 | 20.9 | 76.7 | 76.9 | 2.3 | 8.3 |
| 300 | PO | 0.5% MC | Compound 23 | 23.8 | 155.1 | 155 | 1.2 | 5.6 |
| 30 | PO | 0.5% MC | Compound W | 0.0264 | 0.0453 | 0.206 | 0.83 | — |
| 100 | PO | 0.5% MC | Compound W | 0.322 | 0.432 | 0.437 | 0.67 | 5.31 |
| 300 | PO | 0.5% MC | Compound W | 4 | 3.69 | 3.76 | 0.58 | 13.15 |

Monkey IV Study

Male cynomolgus monkeys (n=3 per dose group) were administered a single nominal IV bolus dose of 1 mg/kg of Compound W via a jugular vein cannula. Compound W was formulated in D5W (5% dextrose in water solution). Animals had free access to food and water before and after dosing.

Blood samples (approximately 0.25 mL each) were collected via a carotid artery catheter prior to dosing and at 0 (predose), 5 min, 10 min, 0.25, 0.5, 1, 2, 3, 4, 6, 8, 12, 24, 48 hours postdose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W, with a lower limit of quantitation (LLOQ) of 1 to 20 ng/mL, depending on the sample dilution factor. Plasma concentration vs. time data were subjected to noncompartmental pharmacokinetic (PK) analysis. The results of this analysis are provided in Table 18.

TABLE 18

Pharmacokinetic Data from Monkey IV Study

| Dose (mg/kg) | Route | Formulation | Analyte | C0 (ug/ml) | AUC (ug * hr/ml) | AUCextrap (ug * hr/ml) | Cl (ml/min/kg) | t½ (hr) | Vss (L/kg) |
|---|---|---|---|---|---|---|---|---|---|
| 5 | IV | D5W | Compound 23 | 10.9 | 3.78 | 3.81 | 23.4 | 6.17 | 2.09 |
| 5 | IV | D5W | Compound W | 62.4 | 5.79 | 5.83 | 18.2 | 5.35 | 1.88 |

Rat Oral Study

Groups of maleSprague Dawley rats (n=3 per dose group) were administered single nominal oral doses of 3, 10, 30, 300 mg/kg of Compound W by gavage. Compound W was formulated in either 0.5% MC (microcrystalline cellulose) or 20% Captisol, 1% HPMC-AS (hydroxypropyl methylcellulose acetyl succinate), 1% PVP (polyvinylpyrrolidone). Animals had free access to food and water before and after dosing. Blood samples (approximately 0.25 mL each) were collected via a carotid artery catheter prior to dosing and at 0 (predose), 0.25, 0.5, 1, 1.5, 2, 4, 6, 8, 12, 24 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma concentration vs. time data was subjected to noncompartmental pharmacokinetic (PK) analysis. The results of this analysis are provided in Table 19.

TABLE 19

Pharmacokinetic Data from Rat Oral Study

| Dose (mg/kg) | Formulation | Analyte | Cmax/C0 (ug/ml) | AUC (ug * hr/ml) | AUCextrap (ug * hr/ml) | Tmax (hr) | t½ (hr) |
|---|---|---|---|---|---|---|---|
| 3 | 0.5% MC | Compound 23 | 0.117 | 0.311 | 0.314 | 0.58 | 4.06 |
| 30 | 0.5% MC | Compound 23 | 2.9 | 22.5 | 22.6 | 1.7 | 2.6 |
| 100 | 0.5% MC | Compound 23 | 6.6 | 77.1 | 77.4 | 2.5 | 2.7 |
| 300 | 0.5% MC | Compound 23 | 11.7 | 222.8 | 307.6 | — | 17.9 |
| 300 | 20% CAPT, 1% HPMC-AS, 1% PVP | Compound 23 | 16.2 | 294.6 | — | 5 | — |
| 3 | 0.5% MC | Compound W | — | — | — | — | — |
| 30 | 0.5% MC | Compound W | 0.022 | 0.178 | 0.058 | 3.3 | 3.1 |
| 100 | 0.5% MC | Compound W | 0.021 | 0.061 | 0.066 | 0.8 | 7.2 |
| 300 | 0.5% MC | Compound W | 2.33 | 0.324 | 0.464 | 1.2 | 11.3 |
| 300 | 20% CAPT, 1% HPMC-AS, 1% PVP | Compound W | 0.6 | 2.37 | 4.27 | 1.8 | — |

Rat IV Study

Groups of male Sprague Dawley rats (n=3 per dose group) were administered single nominal IV bolus doses of 1 and 5 mg/kg of Compound W via a jugular vein cannula. Compound W was formulated in D5W. Animals had free access to food and water before and after dosing. Blood samples (approximately 0.25 mL each) were collected via a carotid artery catheter prior to dosing and at 0 (predose), 5 min, 10 min, 0.25, 0.5, 1, 1.5, 2, 4, 6, 8, 12, 24 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma concentration vs. time data were subjected to noncompartmental pharmacokinetic (PK) analysis. The results of this analysis are provided in Table 20.

TABLE 20

Pharmacokinetic Data from Rat IV Study

| Dose (mg/kg) | Formulation | Analyte | Cmax/C0 (ug/ml) | AUC (ur*hr/ml) | AUCextrap (ug*hr/ml) | $t^{1/2}$ (hr) | Cl_obs (ml/min/kg) | Vss_obs (L/kg) |
|---|---|---|---|---|---|---|---|---|
| 1 | D5W | Compound 23 | 0.247 | 0.306 | 0.31 | 1.8 | 54.9 | 3.8 |
| 5 | D5W | Compound 23 | 1.2 | 3.04 | 3.06 | 3.6 | 27.3 | 4.08 |
| 1 | D5W | Compound W | 4.8 | 0.416 | 0.419 | 0.9 | 46.7 | 0.38 |
| 5 | D5W | Compound W | 9.03 | 1.11 | 1.12 | 7.2 | 84.6 | 5.8 |

Mouse Oral Study

Groups of female CD-1 mice (n=3 per dose group) were administered single nominal oral doses of 10, 30, 100 mg/kg of Compound W by gavage. Compound W was formulated in 0.5% MC. Animals had free access to food and water before and after dosing. Blood samples (approximately 0.025 mL each) were collected from the sub-mandibular vein prior to dosing and at 0 (predose), 0.25, 0.5, 1, 1.5, 2, 4, 6, 8, 12, 24 hours postdose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method with a lower limit of quantitation (LLOQ) of 1 to 20 ng/mL, depending on the sample dilution factor. Plasma concentration vs. time data was subjected to noncompartmental pharmacokinetic (PK) analysis. The results of this analysis are provided in Table 21.

TABLE 21

Pharmacokinetic Data from Mouse Oral Study

| Dose (mg/kg) | Formulation | AUC (0-t) (μg*hr/mL) | Cmax (μg*hr/ml) | Tmax (hr) |
|---|---|---|---|---|
| 10 | 0.5% MC | 1.7 | 1.2 | 0.3 |
| 30 | 0.5% MC | 4.1 | 2.1 | 0.3 |
| 100 | 0.5% MC | 26.6 | 9.1 | 0.4 |

The studies described above, demonstrate that Compound W is converted in vivo into Compound 23 in at least rats, dogs and monkeys.

Example 37

Enzymology Studies

The enzyme inhibition activities of selected compounds of this invention were determined in the experiments described below:

DNA Gyrase ATPase Assay

The ATP hydrolysis activity of S. aureus DNA gyrase was measured by coupling the production of ADP through pyruvate kinase/lactate dehydrogenase to the oxidation of NADH. This method has been described previously (Tamura and Gellert, 1990, J. Biol. Chem., 265, 21342).

ATPase assays were carried out at 30° C. in buffered solutions containing 100 mM TRIS pH 7.6, 1.5 mM $MgCl_2$, 150 mM KCl. The coupling system contains final concentrations of 2.5 mM phosphoenol pyruvate, 200 μM nicotinamide adenine dinucleotide (NADH), 1 mM DTT, 30 ug/ml pyruvate kinase, and 10 ug/ml lactate dehydrogenase. The enzyme (90 nM final concentration) and a DMSO solution (3% final concentration) of the selected compound were added. The reaction mixture was allowed to incubate for 10 minutes at 30° C. The reaction was initiated by the addition of ATP to a final concentration of 0.9 mM, and the rate of NADH disappearance was monitored at 340 nanometers over the course of 10 minutes. The $K_i$ and $IC_{50}$ values were determined from rate versus concentration profiles.

Selected compounds of the present invention were found to inhibit S. aureus DNA gyrase. Table 22 shows the inhibitory activity of these compounds in the S. aureus DNA gyrase inhibition assay.

TABLE 22

Inhibition of S. aureus DNA Gyrase

| Selected Compound | $K_i$ (nM) | $IC_{50}$ (nM) |
|---|---|---|
| Compound 23 | 9 | |
| Compound W | <9 | 54 |

DNA Topo IV ATPase Assay

The conversion of ATP to ADP by S. aureus TopoIV enzyme was coupled to the conversion of NADH to NAD+, and the progress of the reaction was measured by the change in absorbance at 340 nm. TopoIV (64 nM) was incubated with the selected compound (3% DMSO final) in buffer for 10 minutes at 30° C. The buffer consisted of 100 mM Tris 7.5, 1.5 mM $MgCl_2$, 200 mM K. Glutamate, 2.5 mM phosphoenol pyruvate, 0.2 mM NADH, 1 mM DTT, 5 μg/mL linearized DNA, 50 μg/mL BSA, 30 μg/mL pyruvate kinase, and 10 μg/mL lactate dehyrodgenase (LDH). The reaction was initiated with ATP, and rates were monitored continuously for 20 minutes at 30° C. on a Molecular Devices SpectraMAX plate reader. The inhibition constant, Ki, and the $IC_{50}$ were determined from plots of rate vs. concentration of selected compound fit to the Morrison Equation for tight binding inhibitors.

Selected compounds of the present invention were found to inhibit S. aureus DNA Topo IV. Table 23 shows the inhibitory activity of these compounds in the S. aureus DNA gyrase inhibition assay.

TABLE 23

Inhibition of S. aureus DNA Topo IV

| Selected Compound | $K_i$ (nM) | $IC_{50}$ (nM) |
|---|---|---|
| Compound 23 | 12 | |
| Compound W | 30 | 150 |

Example 38

Aqueous Solubility Study

The aqueous solubilities of compound 23 and compound W were determined according to the following procedure.

Preparation of Samples. Aqueous samples of each compound were prepared as follows. Compounds were weighed (20-30 mg compound) in 4 ml clear vials prior to adding water (0.5 mL) and stirring by magnetic stirrer. 1.0N HCl was added to the suspension to adjust the pH to the desired range. After stirring for 96 hours at room temperature, the suspension was filtered through a 0.22 micron filter (Millipore, Ultrafree centrifugal filters, Durapore PVDF 0.22 µm, Cat#UFC30GVNB). The filtrate was collected and the pH measured with a pH meter. The filtrate containing compound W was diluted 10-fold to provide an appropriate concentration for HPLC analysis. The filtrate containing compound 23 did not require dilution.

Preparation of Standard Solutions. Standard solutions of each compound were prepared according to the following procedure. 1 to 2 mg of each compound was accurately weighed into a 10 mL volumetric flask and either water (for compound W) or 1:1 methanol:0.1N HCl (for compound 23) was added to completely dissolve the compounds. Sonication was performed for compound 23 to assist with the dissolution in 1:1 methanol:0.1N HCl. When all solids dissolved, additional solvent was added to adjust the volume of each solution to 10 ml. The resulting solutions were thoroughly mixed to give the standard solutions of each compound. Each standard solution was then diluted with solvent by 2-fold, 10-fold, and 100-fold.

Solubility Analysis. Aliquots of each sample and each standard solution were analyzed by HPLC analysis (Agilent 1100, injection volume 10 µL, wavelength 271 nm, column XTerra® Phenyl 5 µm, 4.6×50 mm, Part No. 186001144, mobile phase: A: 0.1% TFA in water 0.1% TFA in AcN). Each standard solution was injected three times, and each of the samples was injected twice. Standard curves were obtained by plotting the average of the peak area from the HPLC versus the concentrations of the standard solutions (with appropriate corrections of the weights of the standards based on total water content of the solid as determined by elemental analysis). The concentration of each sample was calculated from the peak area of the aqueous sample from the HPLC results and the slope and intercept of the standard curves. The solubility values listed in Table 24 below were derived from the product of the concentration of the sample and the dilution factor of the sample.

TABLE 24

Aqueous Solubility of Compounds 23 and W

| Compound | Solid form | pH | Solubility (mg/mL) |
|---|---|---|---|
| Compound 23 | crystalline | >3.0 | <0.001 |
| Compound W | crystalline | 4.39 | 0.25 |

Example 39

In Vivo Metabolism Study in Hepatic and Liver S9 Cells

The conversion of Compound W to Compound 23 was studied in liver and intestinal S9 fractions from rats, dogs, monkeys and humans. Compound W was incubated at 0.1, 0.3, 1, 3, 10, 20, 40, 100, 200, 300 µM in liver S9 fractions and at 1, 3, 10, 20, 100, 300, 500, 1000 µM in intestinal S9 fractions. The incubations were done for 0, 5, 10, 15, 30, 45 or 60 minutes. The formation of Compound 23 was quantified by LC/MS-MS and data were fitted to the Michaelis Menten equation. The data in Table 25 below indicates that Compound W rapidly converts to Compound 23 in these hepatic and intestinal S9 fractions.

TABLE 25

Velocity of formation ($V_{MAX}$) of Compound 23 from Compound W in Liver and Intestinal S9

| | $V_{MAX}$ (liver) (pmoles/min/mg) | $V_{MAX}$ (intestine) (pmoles/min/mg) |
|---|---|---|
| Dog | 19.3 | 1162 |
| Monkey | 25.2 | 1974 |
| Rat | 45.5 | 958 |
| Human | 45.8 | ND* |

*ND: Parameters not determined, rate of formation did not saturate

What is claimed is:

1. A compound of formula

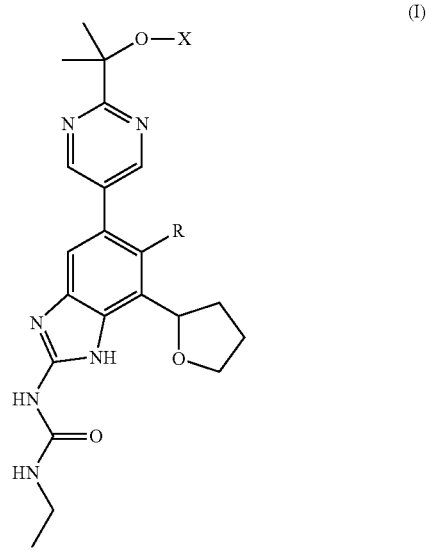

(I)

wherein R is hydrogen or fluorine; X is hydrogen, —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation.

2. The compound according to claim 1 having the formula

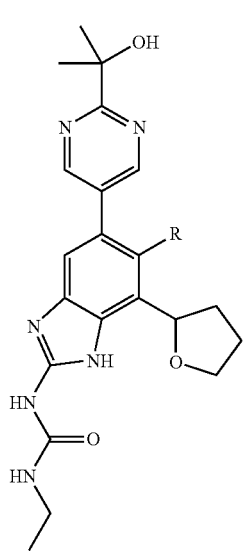
(IA)

wherein R is hydrogen or fluorine.

3. The compound according to claim 1 having the formula

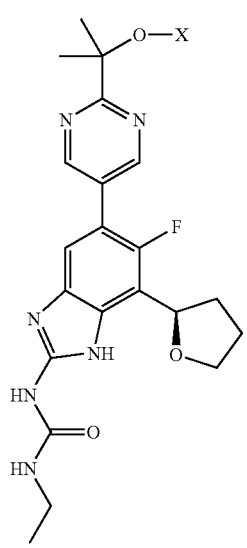
(IB)

wherein X is —PO(OH)$_2$, —PO(OH)O$^-$M$^+$, —PO(O$^-$)$_2$.D$^{2+}$; M$^+$, or —PO(O$^-$)$_2$.D$^{2+}$; M$^+$ is a pharmaceutically acceptable monovalent cation; and D$^{2+}$ is a pharmaceutically acceptable divalent cation.

4. The compound according to claim 1 having the formula

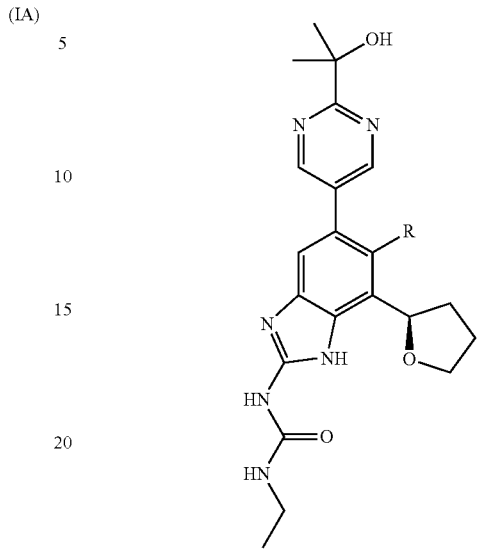
(IC)

wherein R is hydrogen or fluorine.

5. The compound according to claim 4, wherein the compound is (R)-1-ethyl-3-(5-(2-(2-hydroxypropan-2-yl)pyrimidin-5-yl)-7-(tetrahydrofuran-2-yl)-1H-benzo[d]imidazol-2-yl)urea.

6. The compound according to claim 4, wherein the compound is (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea.

7. The compound according to claim 1, wherein the compound is (R)-2-(5-(2-(3-ethylureido)-6-fluoro-7-(tetrahydrofuran-2-yl)-1H-benzo[d]imidazol-5-yl)pyrimidin-2-yl)propan-2-yl dihydrogen phosphate.

8. A pharmaceutical composition comprising a compound according to claim 1 and a pharmaceutically acceptable carrier, adjuvant, or vehicle.

9. A pharmaceutical composition comprising a compound according to claim 2 and a pharmaceutically acceptable carrier, adjuvant, or vehicle.

10. A pharmaceutical composition comprising a compound according to claim 3 and a pharmaceutically acceptable carrier, adjuvant, or vehicle.

11. A method of decreasing or inhibiting *Mycobacterium tuberculosis, Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci bacterial quantity in a biological sample comprising contacting said biological sample with a compound according to claim 1.

12. A method of treating a bacterial infection in a patient, wherein the bacterial infection is characterized by the presence of one or more of *Mycobacterium tuberculosis, Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium abscessus, Mycobacterium kansasii, Mycobacterium* ulcerans, Chlamydophila pneumoniae, Chlamydia trachomatis, Haemophilus influenzae, Streptococcus pyogenes or β-haemolytic streptococci, comprising administering to said patient a compound according to claim 1.

13. The method according to claim 12, wherein the bacterial infection is selected from one or more of the following: upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial pneumoniae (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

14. The method according to claim 13, wherein the bacterial infection is selected from one or more of the following: community-acquired bacterial pneumoniae (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

15. A pharmaceutical composition comprising a compound according to claim 5 and a pharmaceutically acceptable carrier, adjuvant, or vehicle.

16. A method of treating a bacterial infection in a patient, wherein the bacterial infection is characterized by the presence of one or more of *Mycobacterium tuberculosis, Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci, comprising administering to said patient a compound according to claim 5.

17. The method according to claim 16, wherein the bacterial infection is selected from one or more of the following: community-acquired bacterial pneumoniae (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

18. A pharmaceutical composition comprising a compound according to claim 6 and a pharmaceutically acceptable carrier, adjuvant, or vehicle.

19. A method of treating a bacterial infection in a patient, wherein the bacterial infection is characterized by the presence of one or more of *Mycobacterium tuberculosis, Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci, comprising administering to said patient a compound according to claim 6.

20. The method according to claim 19, wherein the bacterial infection is selected from one or more of the following: community-acquired bacterial pneumoniae (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

21. A pharmaceutical composition comprising a compound according to claim 7 and a pharmaceutically acceptable carrier, adjuvant, or vehicle.

22. A method of treating a bacterial infection in a patient, wherein the bacterial infection is characterized by the presence of one or more of *Mycobacterium tuberculosis, Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci, comprising administering to said patient a compound according to claim 7.

23. The method according to claim 22, wherein the bacterial infection is selected from one or more of the following: community-acquired bacterial pneumoniae (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

24. A method of treating a bacterial infection in a patient, wherein the bacterial infection is characterized by the presence of one or more of *Mycobacterium tuberculosis, Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci, comprising administering to said patient a compound according to claim 3.

25. The method according to claim 24, wherein the bacterial infection is selected from one or more of the following: community-acquired bacterial pneumoniae (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

\* \* \* \* \*